US008153373B2

(12) United States Patent
De Laat et al.

(10) Patent No.: US 8,153,373 B2
(45) Date of Patent: *Apr. 10, 2012

(54) CAPTURE AND CHARACTERIZED CO-LOCALIZED CHROMATIN (4C) TECHNOLOGY

(75) Inventors: Wouter De Laat, Utrecht (NL); Frank Grosveld, Rotterdam (NL)

(73) Assignee: Erasmus University Medical Center (NL)

( * ) Notice: Subject to any disclaimer, the term of this patent is extended or adjusted under 35 U.S.C. 154(b) by 441 days.

This patent is subject to a terminal disclaimer.

(21) Appl. No.: 12/006,747

(22) Filed: Jan. 4, 2008

(65) Prior Publication Data

US 2010/0075861 A1    Mar. 25, 2010

Related U.S. Application Data

(63) Continuation of application No. PCT/IB2006/002268, filed on Jul. 3, 2006.

(30) Foreign Application Priority Data

Jul. 4, 2005  (GB) .................................. 0513676.7
Mar. 17, 2006  (GB) .................................. 0605449.8

(51) Int. Cl.
*C12Q 1/68*    (2006.01)
*C12P 19/34*    (2006.01)
(52) U.S. Cl. ...................................... 435/6.12; 435/91.2
(58) Field of Classification Search ........................ None
See application file for complete search history.

(56) References Cited

U.S. PATENT DOCUMENTS

2005/0130161 A1* 6/2005 Fraser et al. ...................... 435/6
2010/0062947 A1* 3/2010 De Laat et al. ................... 506/8

OTHER PUBLICATIONS

Dekker J. et. al: Capturing chromosome conformation:, Science, American Assoc. for the Advancement of Science, U.S., vol. 295, No. 5558, Feb. 15, 2002, pp. 1306-1311.
Tolhuis B, et al.: "Looping and interaction between hypersensitive sites in the active beta-globin locus", Molecular Cell, Cell Press, Cambridge, MA U.S., vol. 10, No. 6, Dec. 2002, pp. 1453-1465.
Splinter Erik, et al.: "3C technology: analyzing the spatial organiation of genomic loci in vivo", Methods in Enzymology 2004, vol. 375, 2004, pp. 493-507.
Rippe K: Making contacts on a nucleic acid polymer: Trends in biochemical Scinences, Elsevier Haywards, GB, vol. 26, No. 12, Dec. 1, 2001, pp. 733-740.
Hacia J. G.: "Resquencing and Mutational Analysis Using Oligonucleotide Microarrays" nature Genetics, New York, NY, U.S. vol. 21, No. Suppl, Jan. 1999, pp. 42-47.
Albert T., et al.: High-throughput prokaryotic and viral mapping and resequencing using ustom high-density arrays: Abstracts of the General Meetingo f the American Society for Microbiology, No. 154th, Apr. 2, 2004, p. 70.
Ling Jian Qun et al., "CTCF mediates interchromosomal colocalization between Igf2.H19 and Wsb1/Nfl.", Science, Apr. 14, 2006, pp. 269-272.
Ling J.Q., et al; CTCF Mediates Interchromosomal colocalization between Igf2/H19 and Wsb1/Nf1 Science, Supporting Online Materials, Apr. 14, 2006.
Zhao Zhihu et al.: "Circular chromosome conformation capture (4C) uncovers extensive networks of epigenetically regulated intra- and interchromosomal interactions>" nature Genetics, Nov. 2005, vol. 38, No. 11, Nov. 2006, pp. 1341-1347.
Simonis Marieke et al., "Nuclear organization of active and inactive chromatin domains uncovered by chromosome confomration capture-on-chip (4C." Nature Genetics Nov 290006, vol. 38, No. 11 Nov. 2006, pp. 1348-1354.
International Search Report from parent application No. PCT/IB2006/002268.
Palstra et al., Nature Genetics, 35(2): 190-194, (2003).
Patrinos et al., Genes & Development, 18:1495-1509, (2004).
Drissen et al., Genes & Development, 18: 2485-2490, (2004).
Vakoc et al., Molecular Cell, 17: 453-462, (2005).
Spilianakis et al., Nature Immunology, 5(10): 1017-1027, (2004).
Blanton et al., Genes & Development, 664-675, (2003).
Murrell et al., Nature Genetics, 36(8): 869-893, (2004).
Horike et al., Nature Genetics, 37(1):31-40, (2005).
Ochman et al., Genetics, 120: 621-623, (1988).
Solomon et al., Biochemistry,82: 6470-6474, (1985).
Lomvardas et al., "Interchromosomal Interactions and Olfactory Receptor Choice," Cell (2006); 126:403-413.
Cardarelli-Leite, Paola et al., "Rapid Identification of Campylobacter Species by Restriction Fragment Length Polymorphism Analysis of a PCR-Amplified Fragment of the Gene Coding for 16S rRNA", Journal of Clinical Microbiology, Jan. 1996, p. 62-67.

* cited by examiner

*Primary Examiner* — Kenneth R. Horlick
*Assistant Examiner* — David Thomas
(74) *Attorney, Agent, or Firm* — McKee, Voorhees & Sease, P.L.C.

(57) ABSTRACT

The present invention relates in one aspect to a method for analyzing the frequency of interaction of a target nucleotide sequence with one or more nucleotide sequences of interest (e.g., one or more genomic loci) comprising the steps of: (a) providing a sample of cross-linked DNA; (b) digesting the cross-linked DNA with a primary restriction enzyme; (c) ligating the cross-linked nucleotide sequences; (d) reversing the cross linking; (e) digesting the nucleotide sequences with a secondary restriction enzyme; (f) ligating one or more DNA sequences of known nucleotide composition to the available secondary restriction enzyme digestion site(s) that flank the one or more nucleotide sequences of interest; (g) amplifying the one or more nucleotide sequences of interest using at least two oligonucleotide primers, wherein each primer hybridises to the DNA sequences that flank the nucleotide sequence of interest; (h) hybridising the amplified sequence(s) to an array; and (i) determining the frequency of interaction between the DNA sequences.

30 Claims, 21 Drawing Sheets
(1 of 21 Drawing Sheet(s) Filed in Color)

1.
formaldehyde fixation of cells
—genomic sites close in nuclear
space are crosse-linked—

2.
Restriction enzyme digestion
—digestion of cross-linked chromatin in nucleus—

3.
Intramolecular ligation
—ligation of cross-linked DNA fragments—

4.
Reverse cross-links/
purify DNA

5.
Quantify ligation products by PCR

*FIG. 1*

CAPTURE AND CHARACTERIZED CO-LOCALIZED CHROMATIN (4C) TECHNOLOGY

RELATED APPLICATIONS

This is a continuation patent application that claims priority to PCT patent application number PCT/IB2006/002268, filed on Jul. 3, 2006, which claims priority to GB patent application number 0605449.8 filed on Mar. 17, 2006, which claims priority to GB patent application 0513676.1 filed on Jul. 4, 2005, the entirety of which are herein incorporated by reference.

FILED OF INVENTION

The present invention relates to the analysis of the frequency of interaction of two or more nucleotide sequences in the nuclear space.

BACKGROUND TO THE INVENTION

Studies on mammalian nuclear architecture aim to understand how 2 meters of DNA is folded into a nucleus of 10 μm across, while allowing accurate expression of the genes that specify the cell-type, and how this is faithfully propagated during each cell cycle. Progress to in this field has largely come from microscopy studies, which revealed that genomes are non-randomly arranged in the nuclear space. For example, densely packed heterochromatin is separated from more open euchromatin and chromosomes occupy distincy territories in the nuclear space. An intricate relationship exists between nuclear positioning and transcriptional activity. Although transcription occurs through the nuclear interior, active genes that cluster on chromosomes preferentially locate at the edge or outside of their chromosome territory. Individual genes may migrate upon changes in their transcription status, as measured against relatively large nuclear landmarks such as chromosome territories, centromeres or the nuclear periphery. Moreover, actively transcribed genes tens of megabases apart on the chromosome can come together in the nucleus, as demonstrated recently by fluorescence in situ hybridization (FISH) for the β-globin locus and a few, selected, other genes. Besides transcription, genomic organization is associated with the coordination of replication, recombination and the probability of loci to translocate (which can lead to malignancies) and the setting and resetting of epigenetic programs. Based on these observations it is thought that the architectural organization of DNA in the cell nucleus is a key contributor of genomic function.

Different assays have been developed to allow an insight into the spatial organization of genomic loci in vivo. One assay, called RNA-TRAP has been developed (Carter et al. (2002) Nat. Genet. 32, 623) which involves targeting of horseradish peroxidase (HRP) to nascent RNA transcripts, followed by quantitation of HRP-catalysed biotin deposition on chromatin nearby.

Another assay that has been developed is called chromosome conformation capture (3C) technology, which provides a tool to study the structural organisation of a genomic region. 3C technology involves quantitative PCR-analysis of cross-linking frequencies between two given DNA restriction fragments, which gives a measure of their proximity in the nuclear space (see FIG. 1). Originally developed to analyse the conformation of chromosomes in yeast (Dekker et al., 2002), this technology has been adapted to investigate the relationship between gene expression and chromatin folding at intricate mammalian gene clusters (see, for example, Tolhuis et al., 2002; Palstra et al., 2003; and Drissen et al., 2004). Briefly, 3C technology involves in vivo formaldehyde cross-linking of cells and nuclear digestion of chromatin with a restriction enzyme, followed by ligation of DNA fragments that were cross-linked into one complex. Ligation products are then quantified by PCR. The PCR amplification step requires the knowledge of the sequence information for each of the DNA fragments that are to be amplified. Thus, 3C technology provides a measure of interaction frequencies between selected DNA fragments.

There is an important need for high-throughput technology that can systematically screen the whole genome in an unbiased manner for DNA loci that contact each other in the nuclear space.

The present invention seeks to provide improvements in 3C technology.

SUMMARY OF THE INVENTION 3C technology as currently applied only allows analysis of a limited number of selected DNA-DNA interactions owing to the limitations of the PCR amplification step, which requires knowledge of specific sequence information for each fragment to be analysed. Moreover, selecting restriction fragments as candidates for long-range DNA interactions requires a substantial amount of prior knowledge (e.g. the location of hypersensitive sites) of the locus of interest, which is usually not available. Given the functional relevance of many long-range DNA-DNA interactions described so far, the ability to randomly screen for DNA elements that loop to a sequence of interest—such as a gene promoter, enhancer, insulator, silencer, origin of replication or MAR/SAR—or a genomic region of interest—such as a gene-dense or gene-poor region or repetitive element—can greatly facilitate the mapping of sequences involved in a regulatory network.

The present invention relates to 4C technology (i.e. capture and characterise co-localised chromatin), which provides for the high-throughput analysis of the frequency of interaction of two or more nucleotide sequences in the nuclear space.

4C (capture and characterize co-localized chromatin) technology is a modified version of 3C technology that allows an unbiased genome-wide search for DNA fragments that interact with a locus of choice. Briefly, 3C analysis is performed as usual, but omitting the PCR step. The 3C template contains a bait (e.g. a restriction fragment of choice that encompasses a gene of interest) ligated to many different nucleotide sequences of interest (representing this gene's genomic environment). The template is cleaved by another, secondary, restriction enzyme, and ligated. Advantageously, the one or more nucleotide sequences of interest that are ligated to the target nucleotide sequence are amplified using at least one (preferably, at least two) oligonucleotide primer, wherein the at least one primer hybridises to a DNA sequence that flanks the nucleotide sequences of interest. Typically, this yields a pattern of PCR fragments that is highly reproducible between independent amplification reactions and specific for a given tissue. In one embodiment, HindIII and DpnII are used as primary and secondary restriction enzyme. Next, the amplified fragments may be labeled and optionally hybridised to an array, typically against a control sample containing genomic DNA digested with the same combination of restriction enzymes.

In one preferred embodiment of the present invention, the ligated fragments that are cleaved by a secondary restriction enzyme are subsequently religated to form small DNA circles.

3C technology has therefore been modified such that all nucleotide sequences of interest that interact with a target nucleotide sequence are amplified. Practically this means that instead of performing an amplification reaction with primers that are specific for the fragments that one wishes to analyse, an amplification is performed using oligonucleotide primer(s) which hybridise to a DNA sequence that flanks the nucleotide sequences of interest. Advantageously, 4C is not biased towards the design of PCR primers that are included in the PCR amplification step and can therefore be used to search the complete genome for interacting DNA elements.

SUMMARY ASPECTS OF THE PRESENT INVENTION

Aspects of the present invention are presented in the accompanying claims.

In a first aspect, there is provided a method for analysing the frequency of interaction of a target nucleotide sequence with one or more nucleotide sequences of interest (e.g. one or more genomic loci) comprising the steps of: (a) providing a sample of cross-linked DNA; (b) digesting the cross-linked DNA with a primary restriction enzyme; (c) ligating the cross-linked nucleotide sequences; (d) reversing the cross linking; (e) digesting the nucleotide sequences with a secondary restriction enzyme; (f) ligating one or more DNA sequences of known nucleotide composition to the available secondary restriction enzyme digestion site(s) that flank the one or more nucleotide sequences of interest; (g) amplifying the one or more nucleotide sequences of interest using at least two oligonucleotide primers, wherein each primer hybridises to the DNA sequences that flank the nucleotide sequences of interest; (h) hybridising the amplified sequence(s) to an array; and (i) determining the frequency of interaction between the DNA sequences.

In a second aspect, there is provided a method for analysing the frequency of interaction of a target nucleotide sequence with one or more nucleotide sequences (e.g. one or more genomic loci) comprising the steps of (a) providing a sample of cross-linked DNA; (b) digesting the cross-linked DNA with a primary restriction enzyme; (c) ligating the cross-linked nucleotide sequences; (d) reversing the cross linking; (e) digesting the nucleotide sequences with a secondary restriction enzyme; (f) circularising the nucleotide sequences; (g) amplifying the one or more nucleotide sequences that are ligated to the target nucleotide sequence; (h) optionally hybridising the amplified sequences to an array; and (i) determining the frequency of interaction between the DNA sequences.

In a third aspect there is provided a circularised nucleotide sequence comprising a first and a second nucleotide sequence, wherein each end of the first and a second nucleotide sequences are separated by different restriction enzyme recognition sites, and wherein said first nucleotide sequence is a target nucleotide sequence and said second nucleotide sequence is obtainable by cross-linking genomic DNA.

In a fourth aspect there is provided a method for preparing a circularised nucleotide sequence comprising the steps of (a) providing a sample of cross-linked DNA; (b) digesting the cross-linked DNA with a primary restriction enzyme; (c) ligating the cross-linked nucleotide sequences; (d) reversing the cross linking; (e) digesting the nucleotide sequences with a secondary restriction enzyme; and (f) circularising the nucleotide sequences.

In a fifth aspect there is provided a method for analysing the frequency of interaction of a target nucleotide sequence with one or more nucleotide sequences (e.g. one or more genomic loci) comprising the use of the circularised nucleotide sequence.

In a sixth aspect there is provided an array of probes immobilised on a support comprising one or more probes that hybridise or are capable of hybridising to the circularised nucleotide sequence.

In a seventh aspect there is provided a set of probes complementary in sequence to the nucleic acid sequence adjacent to each one of the primary restriction enzyme recognition sites of a primary restriction enzyme in genomic DNA.

In an eighth aspect there is provided a process for preparing a set of probes comprising the steps of: (a) identifying each one of the primary restriction enzyme recognition sites for a primary restriction enzyme in genomic DNA; (b) designing probes that are capable of hybridising to the sequence adjacent each one of the primary restriction enzyme recognition sites in the genomic DNA; (c) synthesising the probes; and (d) combining the probes together to form a set of probes or substantially a set of probes.

In a ninth aspect there is provided a set of probes or substantially a set of probes obtained or obtainable by the process described herein.

In a tenth aspect there is provided an array comprising the array of probes or substantially the set of probes described herein In an eleventh aspect there is provided an array comprising the set of probes according described herein.

In a twelfth aspect there is provided a process for preparing an array comprising the step of immobilising on a solid support substantially the array of probes or substantially the set of probes described herein.

In an thirteenth aspect there is provided a process for preparing an array comprising the step of immobilising on a solid support the array of probes or the set of probes described herein.

In an fourteenth aspect there is provided an array obtained or obtainable by the method described herein.

In a fifteenth aspect there is provided a method for identifying one or more DNA-DNA interactions that are indicative of a particular disease state comprising the step of performing steps (a)-(i) of the first and second aspects of the present invention, wherein in step (a) a sample of cross-linked DNA is provided from a diseased and a non-diseased cell, and wherein a difference between the frequency of interaction between the DNA sequences from the diseased and non-diseased cells indicates that the DNA-DNA interaction is indicative of a particular disease state.

In an sixteenth aspect there is provided a method of diagnosis or prognosis of a disease or syndrome caused by or associated with a change in a DNA-DNA interaction comprising the step of performing steps (a)-(i) of the first and second aspects of the present invention, wherein step (a) comprises providing a sample of cross-linked DNA from a subject; and wherein step (i) comprises comparing the frequency of interaction between the DNA sequences with that of an unaffected control; wherein a difference between the value obtained from the control and the value obtained from the subject is indicative that the subject is suffering from the disease or syndrome or is indicative that the subject will suffer from the disease or syndrome.

In a seventeenth aspect there is provided a method of diagnosis or prognosis of a disease or syndrome caused by or associated with a change in a DNA-DNA interaction comprising the step of: performing steps (a)-(i) of the first and second aspects of the present invention, wherein step (a) comprises providing a sample of cross-linked DNA from a subject; and wherein said method comprises the additional step of: (j) identifying one or more loci that have undergone a genomic rearrangement that is associated with a disease.

In an eighteenth aspect there is provided an assay method for identifying one or more agents that modulate a DNA-DNA interaction comprising the steps of (a) contacting a sample with one or more agents; and (b) performing steps (a) to (i) of the first and second aspects of the present invention, wherein step (a) comprises providing cross-linked DNA from the sample;
wherein a difference between (i) the frequency of interaction between the DNA sequences in the presence of the agent and (ii) the frequency of interaction between the DNA sequences in the absence of the agent is indicative of an agent that modulates the DNA-DNA interaction.

In a nineteenth aspect there is provided a method for detecting the location of balanced and/or unbalanced breakpoint (e.g. a translocation) comprising the step of (a) performing steps (a) to (i) of the first and second aspects of the present invention; and (b) comparing the frequency of interaction between the DNA sequences with that of a control; wherein a transition from low to high DNA-DNA interaction frequency in the sample as compared to the control is indicative of the location of a breakpoint.

In a twentieth aspect there is provided a method for detecting the location of a balanced and/or unbalanced inversion comprising the steps of: (a) performing steps (a) to (i) of the first and second aspects of the present invention; and (b) comparing the frequency of interaction between the DNA sequences with that of a control; wherein an inversed pattern of DNA-DNA interaction frequencies for the sample as compared to the control is indicative of an inversion.

In a twenty-first aspect there is provided a method for detecting the location of a deletion comprising the steps of (a) performing steps (a) to (i) of the first and second aspects of the present invention; (b) comparing the frequency of interaction between the DNA sequences with that of a control; wherein a reduction in the DNA-DNA interaction frequency for the sample as compared to the control is indicative of deletion.

In a twenty-second aspect there is provided a method for detecting the location of a duplication comprising the steps of (a) performing steps (a) to (i) of the first and second aspects of the present invention; and (b) comparing the frequency of interaction between the DNA sequences with that of a control; wherein an increase or a decrease in DNA-DNA interaction frequency for the subject sample as compared to the control is indicative of a duplication or insertion.

In a twenty-third aspect there is provided an agent obtained or obtainable by the assay method described herein.

In a twenty-fourth aspect there is provided the use of the circularised nucleotide sequence for identifying one or more DNA-DNA interactions in a sample.

In a twenty-fifth aspect there is provided the use of the circularised nucleotide sequence for the diagnosis or prognosis of a disease or syndrome caused by or associated with a change in a DNA-DNA interaction.

In a twenty-sixth aspect there is provided the use of the array of probes or the set of probes described herein for identifying one or more DNA-DNA interactions in a sample.

In a twenty-seventh aspect there is provided the use of the array of probes or the set of probes described herein for the diagnosis or prognosis of a disease or syndrome caused by or associated with a change in a DNA-DNA interaction.

In a twenty-eighth aspect there is provided the use of the array described herein for identifying one or more DNA-DNA interactions in a sample.

In a twenty-ninth aspect there is provided the use of the array described herein for the diagnosis or prognosis of a disease or syndrome caused by or associated with a change in a DNA-DNA interaction.

In a thirtieth aspect there is provided a method, an array of probes, a set of probes, a process, an array, an assay method, an agent, or a use substantially as described herein and with reference to any of the Examples or Figures.

PREFERRED EMBODIMENTS

Preferably, the ligation reaction in step (f) results in the formation of DNA circles.

Preferably, the target nucleotide sequence is selected from the group consisting of a genomic rearrangement, promoter, an enhancer, a silencer, an insulator, a matrix attachment region, a locus control region, a transcription unit, an origin of replication, a recombination hotspot, a translocation breakpoint, a centromere, a telomere, a gene-dense region, a gene-poor region, a repetitive element and a (viral) integration site.

Preferably, the target nucleotide sequence is a nucleotide sequence that is associated with or causes a disease, or is located up to or greater than 15 Mb on a linear DNA template from a locus that is associated with or causes a disease.

Preferably, the target nucleotide sequence is selected from the group consisting of AML1, MLL, MYC, BCL, BCR, ABL1, IGH, LYL1, TAL1, TAL2, LMO2, TCRα/δ, TCRβ and HOX or other loci associated with disease as described in "Catalogue of Unbalanced Chromosome Aberrations in Man" 2nd edition. Albert Schinzel. Berlin: Walter de Gruyter, 2001. ISBN 3-11-011607-3.

Preferably, the primary restriction enzyme is a restriction enzyme that recognises a 6-8 bp recognition site.

Preferably, the primary restriction enzyme is selected from the group consisting of BglII, HindIII, EcoRI, BamHI, SpeI, PstI and NdeI.

Preferably, the secondary restriction enzyme is a restriction enzyme that recognises a 4 or 5 bp nucleotide sequence recognition site.

Preferably, the secondary restriction enzyme recognition site is located at greater than about 350 bp from the primary restriction site in the target nucleotide sequence.

Preferably, the nucleotide sequence is labelled.

Preferably, the probes are complementary in sequence to the nucleic acid sequence adjacent each side of each one of the primary restriction enzyme recognition sites of a primary restriction enzyme in genomic DNA.

Preferably, the probes are complementary in sequence to the nucleic acid sequence that is less than 300 base pairs from each one of the primary restriction enzyme recognition sites of a primary restriction enzyme in genomic DNA.

Preferably, the probes are complementary to the sequence that is less then 300 bp from each one of the primary restriction enzyme recognition sites of a primary restriction enzyme in genomic DNA.

Preferably, the probes are complementary to the sequence that is between 200 and 300 bp from each one of the primary restriction enzyme recognition sites of a primary restriction enzyme in genomic DNA.

Preferably, the probes are complementary to the sequence that is between 100 and 200 bp or 0 to 100 bp from each one of the primary restriction enzyme recognition sites of a primary restriction enzyme in genomic DNA.

Preferably, two or more probes are capable of hybridising to the sequence adjacent each primary restriction enzyme recognition site of a primary restriction enzyme in the genomic DNA.

Preferably, the probes overlap or partially overlap.

Preferably, the overlap is less than 10 nucleotides.

Preferably, the probe sequence corresponds to all or part of the sequence between each one of the primary restriction enzyme recognition sites of a primary restriction enzyme and each one of the first neighbouring secondary restriction enzyme recognition sites of a secondary restriction enzyme.

Preferably, each probe is at least a 25 mer.

Preferably, each probes is a 25-60 mer.

Preferably, the probes are PCR amplification products.

Preferably, the array comprises about 300,000-400,000 probes.

Preferably, the array comprises about 385,000 or more probes, preferably, about 750,000 probes, more preferably, 6×750,000 probes.

Preferably, the array comprises or consists of a representation of the complete genome of a given species at lower resolution.

Preferably, one out of every 2, 3, 4, 5, 6, 7, 8, 9 or 10 probes as ordered on a linear chromosome template is contained in the array.

Preferably, a transition from low to high interaction frequencies is indicative of the location of a balanced and/or unbalanced breakpoint.

Preferably, an inversed pattern of DNA-DNA interaction frequencies for the subject sample as compared to the control is indicative of an balanced and/or unbalanced inversion.

Preferably, a reduction in the DNA-DNA interaction frequency for the subject sample as compared to the control, in combination with an increase in DNA-DNA interaction frequency for more distant regions, is indicative of a balanced and/or unbalanced deletion.

Preferably, an increase or a decrease in DNA-DNA interaction frequency for the subject sample as compared to the control is indicative of a balanced and/or unbalanced duplication or insertion.

Preferably, spectral karyotyping and/or FISH is used prior to performing said method.

Preferably, the disease is a genetic disease.

Preferably, the disease is cancer.

Preferably, the two or more amplified sequences are differentially labelled.

Preferably, the two or more amplified sequences are identically labelled when the sequences reside on different chromosomes.

Preferably, the two or more amplified sequences are identically labelled when the sequences reside on the same chromosome at a distance that is far enough for minimal overlap between DNA-DNA interaction signals.

Preferably, wherein the diagnosis or prognosis is prenatal diagnosis or prognosis.

ADVANTAGES

The present invention has a number of advantages. These advantages will be apparent in the following description.

By way of example, the present invention is advantageous since it provides inter alia commercially useful nucleotides sequences, processes, probes and arrays.

By way of further example, the present invention is advantageous since it provides for the high throughput analysis of the frequency of interaction of two or more nucleotide sequences in the nuclear space.

By way of further example, the present invention is advantageous since using conventional 3C technology, each single DNA-DNA interaction must be analysed by a unique PCR reaction containing a unique pair of primers. High-throughput analysis is therefore only possible if PCR is automated, but the costs of so many primers will be too high. Accordingly, high-throughput (genome-wide) analysis of DNA-DNA interactions is not viable with conventional 3C technology. In contrast, the present invention now allows the simultaneous screening of thousands of DNA-DNA interactions. High-throughput analysis of DNA-DNA interactions according to the present invention will greatly increase the scale and resolution of analysis.

By way of further example, the present invention is advantageous since using conventional 3C technology, the screen is biased towards those DNA sequences for which oligonucleotide primers were designed, ordered and included in the analysis. The choice of such oligonucleotide primers is typically based on knowledge concerning the position of, for example, (distant) enhancers and/or other regulatory elements/hypersensitive sites that it is believed will cross-link with the nucleotide sequence that is being investigated. Thus, conventional 3C is biased towards the design of PCR primers that are included in the PCR amplification step, whereas 4C is unbiased and can be used to search the complete genome for interacting DNA elements. This is because amplification of cross-linked sequences in 4C is not based on the predicted knowledge of sequences that cross-link with the nucleotide sequence being investigated. Rather, in one embodiment of 4C, sequences that cross link to the first (target) nucleotide sequence can be amplified using PCR primers that hybridise to that nucleotide sequence. Thus, the present invention allows an unbiased genome-wide screen for DNA-DNA interactions.

By way of further example, the present invention is advantageous because using conventional 3C technology only allows the selective amplification of a single DNA-DNA interaction. This is not informative when hybridised to an array. The technology has been improved such that all fragments that interact with a first (target) nucleotide sequence are now amplified e.g. selectively amplified.

By way of further example, the present invention is advantageous because 4C technology can be used to detect balanced or unbalanced genetic aberrations—such as all types of translocations, deletions, inversions, duplications and other genomic rearrangements—in nucleic acid, for example, chromosomes. 4C technology (which measures proximity of DNA fragments) can even determine a subject's predisposition to acquire certain translocations, deletions, inversions, duplications and other genomic rearrangements (e.g. balanced or unbalanced translocations, deletions, inversions, duplications and other genomic rearrangements). An advantage over current strategies is that it is not required to know the exact position of the change because the resolution of 4C technology is such that it can be used to detect rearrangements even when the '4C-bait' (as defined by the primary and secondary restriction enzyme recognition sites that are analysed) is located away (e.g. up to one megabase or even more) from the change. Another advantage is that 4C technology allows the accurate mapping of changes since it can be used to define the two (primary) restriction sites between which changes occurred. Another advantage is that cells need not to be cultured before fixation. Thus, for example solid tumours can also be analysed for genomic rearrangements.

By way of further example, the present invention is advantageous because the 4C technology can also detect changes (e.g. rearrangements) in a pre-malignant state, i.e. before all the cells contain these changes. Thus, the technology can be used not only in the diagnosis of disease but also in the prognosis of disease.

By way of further example, the array design according to the present invention is particularly advantageous as compared to existing genomic tiling arrays—such as Nimblegen genomic tiling arrays—since the design allows representation of a much larger part of the genome per single array. By way of example, for a restriction enzyme recognising a hexanucleotide sequence about 3 arrays with about 385,000 probes each will be sufficient to cover, for example, the complete human or mouse genome. For a restriction enzyme recognising more than 6 bp, a single array of about 385,000 probes can be used to cover, for example, the complete human or mouse genome. The advantages of the array design are that: (1) each probe is informative since each analyses an independent ligation event, greatly facilitating the interpretation of the results; and (2) a large representation of the genome can be spotted on a single array which is cost-effective.

4C technology can advantageously be used for the fine-mapping of poorly characterised rearrangements originally detected by cytogenetic approaches (light microscopy, FISH, SKY, etc).

4C technology can advantageously be used for the simultaneous screening on a single array for combinations of rearrangements that have occurred near multiple loci.

BRIEF DESCRIPTION OF THE FIGURES

The file of this patent contains a least one drawing executed in color. Copies of this patent with color drawings will be provided by the United States Patent and Trademark Office upon request and payment of the necessary fee.

FIG. 1

The principle of 3C technology

FIG. 2

Figure 2A:
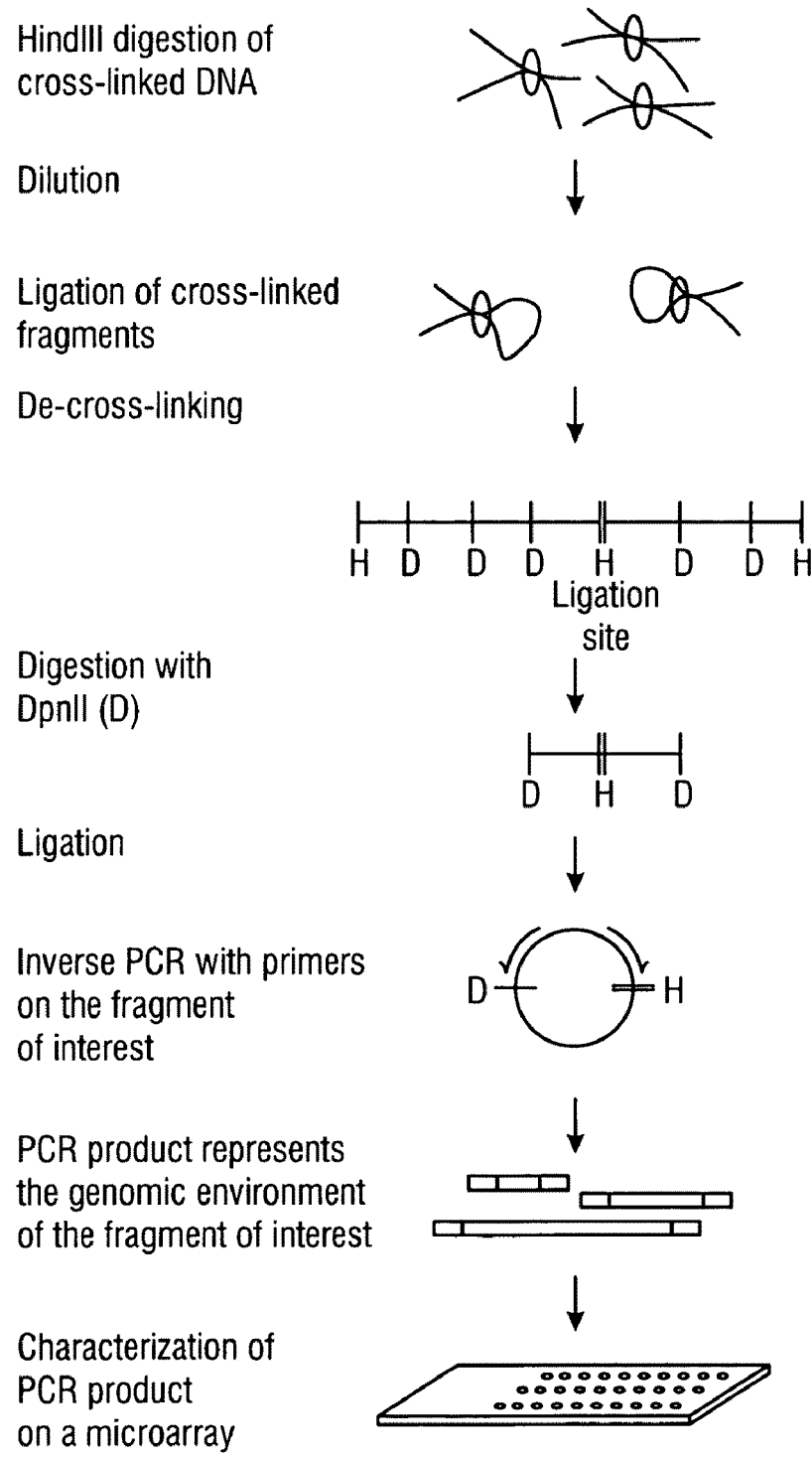

(a) The principle of one embodiment of 4C technology. 3C analysis is performed as usual, with e.g. HindIII (H) as restriction enzyme. After reversal of cross-links, DNA mix will contain a first (target) nucleotide sequence ligated to many different fragments. These fragments will be amplified and labelled by using amplification methods—such as inverse PCR—on e.g., DpnII Circles, using first (target) nucleotide sequence-specific primers. Labelled amplification products may be hybridised to the arrays as described herein. HindIII and DpnII are given as examples, but other combinations of restriction enzymes—such as 6 or 8- and 4 or 5-cutters—can also be used. (b) PCR results separated by gel electrophoresis from two independent fetal liver (L1, L2) and brain (B1, B2) samples. (c) Schematic representation of the location of the microarray probes. Probes were designed within 100 bp of HindIII sites. Thus, each probe analyzes one possible ligation partner.

FIG. 3

4C Technology detects the genomic environment of β-globin (chromosome 7). Shown are unprocessed ratios (4C signals for β-globin HS2 divided by signals obtained for control sample) for probes located in ~35 Mb genomic regions on mouse chromosome 10, 11, 12, 14, 15, 7 and 8 (top to bottom; regions shown are at identical distance from each corresponding centromere). Note the large cluster of strong signals around the (globin) bait on chromosome 7 (row 6), which demonstrates that 4C technology detects genomic fragments close on the linear chromosome template (in agreement with the fact that interaction frequencies are inversely proportional to the genomic site separation). Note that the region linked in cis around the bait that shows high signal intensities is large (>5 Mb), implying for example that translocations can be detected even with baits more than 1 MB away from the breakpoint.

FIG. 4

4C technology detects the genomic environment of Rad23A (chromosome 8). Shown are unprocessed ratios (4C signals for Rad23A divided by signal obtained for control sample) for probes located in ~15 Mb or more genomic regions on mouse chromosome 10, 11, 12, 14, 15, 7 and 8 (top to bottom; regions shown are at identical distance from each corresponding centromere). Note the large cluster of strong signals around the (Rad23A) bait on chromosome 8 (row 7), which demonstrates that 4C technology detects genomic fragments close on the linear chromosome template (in agreement with the fact that interaction frequencies are inversely proportional to the genomic site separation). Note that the region linked in cis around the bait that shows high signal intensities is large (>5 Mb), implying for example that translocations can be detected even with baits more than 1 MB away from the breakpoint.

FIG. 5

4C interactions of β-globin on chromosome 7 (~135 Mb) for a transcribing tissue (fetal liver) and a non-transcribing tissue (fetal brain) (analysed by a running mean approach). Note that long-range interactions with β-globin differ between tissues (likely dependent on the transcription status of the gene). Independent of the tissue strong 4C signals demarcate a large region (>5 Mb) around the bait.

FIG. 6

Uros and Eraf interact with β-globin in fetal liver cells. The 4C approach reveals that two genes, Eraf and Uros, interact over >30 Mb with the β-globin locus located ~30 Mb away. These two interactions were previously found by a different technology (Fluorescence In Situ Hybridisation) as described in Osborne et al., *Nature Genetics* 36, 1065 (2004). This example shows that long-range interactions detected by 4C technology can be verified by FISH and truly reflect nuclear proximity.

FIG. 7

4C technology accurately identifies transitions between unrelated genomic regions that are linked in cis. For these experiments transgenic mice were used that contain a human β-globin Locus Control Region (LCR) cassette (~20 kb) inserted (via homologous recombination) into the Rad23A locus on mouse chromosome 8. 4C technology was performed on E14.5 fetal livers of transgenic mice that were homozygous for this insertion. A HindIII fragment within the integration cassette (HS2) was used as '4C-bait'. The data show that 4C technology accurately defines both ends of the transgenic cassette (bottom row: only probes in the human LCR (~20 kb) give 4C-signals and not probes in the remainder of ~380 kb human β-globin sequence) and clearly reveals the position of integration on mouse chromosome 8 (upper panel: compare signals on chromosome 8 (for position of integration, see arrow) with signals on 6 other mouse chromosomes) (complete chromosomes are depicted). This example shows that 4C technology can be used to detect the genomic position of ectopically integrated DNA fragments (virus, transgene, etc.). It shows that transitions between unrelated genomic regions that are linked in cis can be identified accurately, which can be used to identify genomic breakpoints and translocation partners.

FIG. 8

4C technology produces reproducible data since the profile for HS2 and β-globin are very similar. Four biologically independent 4C experiments were performed on E14.5 fetal livers, using either the β-globin gene β-major (upper 2 rows)

or β-globin HS2 (bottom two rows) as the bait. These baits are ~40 kb apart on the linear chromosome template but were previously shown to be close in the nuclear space (Tolhuii et al, Molecular Cell 10, 1453 (2002)) Depicted is a ~5 Mb region on mouse chromosome 7 that is 20-20 Mb away from the β-globin locus. The data show high reproducibility between independent experiments and demonstrate that two fragments close in the nuclear space share interacting partners located elsewhere in the genome.

FIG. 9

4C technology is applied to measure DNA-DNA interaction frequencies with sequence X (on chromosome A) in cells from a healthy person (top) and a patient with translocation (A; B) (bottom). Signal intensities representing DNA-DNA interaction frequencies (Y-axis) are plotted for probes ordered on linear chromosome templates (X-axis). In normal cells, frequent DNA-DNA interactions are detected on chromosome A around sequence X. In patient cells, a 50% reduction in interaction frequencies is observed for probes on chromosome A located on the other side of the breakpoint (BP) (compare grey curve (patient) with black line (healthy person). Moreover, the translocation brings part of chromosome B in close physical proximity to sequence X, and frequent DNA-DNA interactions are now observed for this region on chromosome B. The abrupt transition from low to high interaction frequencies on this chromosome marks the location of its breakpoint.

FIG. 10

(Balanced) inversion(s) can be detected by 4C technology. Inversed patterns of DNA-DNA interaction frequencies (measured by 4C technology as hybridization signal intensities) are observed in diseased (solid curve) as compared to non-diseased (stippled curve) subject, which reveals the presence and size of the inversion.

FIG. 11

Heterozygous deletion(s) detection by 4C technology. Probes with reduced DNA-DNA interaction frequencies (measured by 4C technology as hybridization signal intensities) in diseased (grey curve) as compared to non-diseased (black curve) subjects, reveal the position and size of the deleted region. Residual hybridization signals in the deleted region of the diseased subject come from intact allele (heterozygous deletion). Deletion is typically accompanied by an increase in signal intensities for probes located directly beyond the deleted region (note that the grey curve is above the black curve at right hand of the deletion), since these regions come in closer physical proximity to the 4C sequence (bait).

FIG. 12

Duplication detected by 4C technology. Probes with increased hybridization signals in a patient (solid curve) as compared to a normal subject (stippled curve) indicate the position and size of duplication. Duplication as detected by 4C technology is typically accompanied by decreased hybridization signals in diseased versus non-diseased subjects for probes beyond the duplicated region (duplication increases their genomic site separation from the 4C sequence).

FIG. 13

Long-range interactions with β-globin revealed by 4C technology. a, Unprocessed ratios of 4C over control hybridization signals, revealing interactions of β-globin HS2 with chromosome 7 and two unrelated chromosomes (8 and 14). b-c, Unprocessed data for two independent fetal liver (top, in red) and fetal brain samples (bottom, in blue) plotted along two different 1-2 Mb regions on chromosome 7. Highly reproducible clusters of interactions are observed either in the two fetal liver samples (b) or the two brain samples (c). d-e, Running mean data for the same regions. False discovery rate was set at 5% (stippled line). f, Schematic representation of regions of interaction with active (fetal liver, top) and inactive (fetal brain, bottom) β-globin on chromosome 7.

FIG. 14

Active and inactive β-globin interact with active and inactive chromosomal regions, respectively. a, Comparison between β-globin long-range interactions in fetal liver (4C running mean, top), microarray expression analysis in fetal liver (log scale, middle) and the location of genes (bottom) plotted along a 4 Mb region that contains the gene Uros (30 Mb away from β-globin), showing that active β-globin preferentially interacts with other actively transcribed genes. b, The same comparison in fetal brain around a OR gene cluster located ~38 Mb away from globin, showing that inactive β-globin preferentially interacts with inactive regions. c, Characterization of regions interacting with β-globin in fetal liver (left) and brain (right) in terms of gene content and activity.

FIG. 15

Ubiquitously expressed Rad23A interacts with very similar, active, regions in fetal liver and brain. a, Schematic representation of regions on chromosome 8 interacting with active Rad23A in fetal liver (top, red) and brain (bottom, blue). b, Comparison between Rad23A long-range interactions (4C running mean) and microarray expression analysis (log scale) in fetal liver (top two panels), Rad23A long-range interactions (4C running mean) and microarray expression analysis (log scale) in fetal brain (panel 3 and 4) and the location of genes (bottom panel) plotted along a 3 Mb region of chromosome 8. c, Characterization of regions interacting with Rad23A in fetal liver (left) and brain (right) in terms of gene content and activity.

FIG. 16

Cryo-FISH confirms that 4C technology truly identifies interacting regions. a, example of part of a (200 nm) cryo-section showing more than 10 nuclei, some of which containing the β-globin locus (green) and/or Uros (red). Due to sectioning, many nuclei do not contain signals for these two loci. b-d, examples of completely (b) and partially (c) overlapping signals and contacting signals (d), which were all scored as positive for interaction. e-g, examples of nuclei containing non-contacting alleles (e-f) and a nucleus containing only β-globin (g), which were all scored as negative for interaction. h-i, Schematic representation of cryo-FISH results. Percentages of interaction with β-globin (h) and Rad23A (i) are indicated above the chromosomes for regions positively identified (red arrowhead) and negatively identified (blue arrowhead) by 4C technology. The same BACs were used for the two tissues. Interaction frequencies measured by cryo-FISH between two distant OR gene clusters in fetal liver and brain are indicated below the chromosomes.

FIG. 17

4C analysis of HS2 and β-major give highly similar results. (a) Unprocessed 4C data of four independent E14.5 liver samples show a very similar pattern of interaction with HS2 (top) and β-major (bottom). (b) A large overlap exists between probes scored positive for interaction in the HS-2 experiment and probes that scored positive for interaction in the β-major experiment.

FIG. 18

A comparison between interactions in cis and in trans. (a) Unprocessed 4C data from two independent experiments showing β-globin interactions with a region positively identified in cis (chromosome 7, top) and a region in trans containing the α-globin locus (chr. 11, bottom). (b) Unprocessed 4C data from two independent experiments showing Rad23A interactions with a region positively identified in cis (chromosome 8, top) and a region in trans that appeared on top when ranked according to highest running mean value. None of the regions in trans met the stringent conditions that allowed the identification of long-interacting regions in cis.

FIG. 19

Regions that interact with β-globin also frequently contact each other. Two regions (almost 60 Mb apart), containing actively transcribed genes and identified by 4C technology to interact with β-globin in fetal liver, showed co-localization frequencies by cryo-FISH of 5.5%, which was significantly more than background co-localization frequencies.

DETAILED DESCRIPTION OF THE INVENTION

3C Technology

The 3C method has been described in detail in Dekker et al. (2002), Tolhuis et al. (2002), Pasha et al. (2003), Splinter et al. (2004) and Drissen et al. (2004). Briefly, 3C is performed by digesting cross-linked DNA with a primary restriction enzyme followed by ligation at very low DNA concentrations. Under these conditions, ligation of cross-linked fragments, which is intramolecular, is strongly favoured over ligation of random fragments, which is intermolecular. Cross-linking is then reversed and individual ligation products are detected and quantified by the polymerase chain reaction (PCR) using locus-specific primers. The cross linking frequency (X) of two specific loci is determined by quantitative PCR reactions using control and cross-linked templates, and X is expressed as the ratio of the amount of the product obtained with the cross-linked template and with the control template.

In accordance with the present invention, a 3C template is prepared using the methods described by Splinter et al., (2004) *Methods Enzymol.* 375, 493-507. (i.e. formaldehyde fixation, (primary) restriction enzyme digestion, re-ligation of cross-linked DNA fragments and DNA purification). Briefly, a sample—such as cells, tissues or nuclei—is fixed using a cross-linking agent—such as formaldehyde. The primary restriction enzyme digestion is then performed such that the DNA is digested in the context of the cross-linked nucleus. Intramolecular ligation is then performed at low DNA concentrations (for example, about 3.7 ng/µl), which favours ligation between cross-linked DNA fragments (i.e. intramolecular ligation) over ligation between non-cross-linked DNA fragments (i.e. intermolecular or random ligation). Next, the cross links are reversed and the DNA can be purified. The 3C template that is yielded contains restriction fragments that are ligated because they were originally close in the nuclear space.

Since a primary restriction enzyme is used to digest the DNA prior to the intramolecular ligation step, an enzyme recognition site for the primary restriction enzyme will separate the first (target) nucleotide sequence and the nucleotide sequence that has been ligated. Accordingly, the primary recognition site is located between the first (target) nucleotide sequence and the ligated nucleotide sequence (i.e. the ligated second sequence).

Nucleotide Sequence

The present invention involves the use of nucleotide sequences (e.g. 3C templates, 4C templates, DNA templates, amplification templates, DNA fragments and genomic DNA), which may be available in databases.

The nucleotide sequence may be DNA or RNA of genomic, synthetic or recombinant origin e.g. cDNA. For example, recombinant nucleotide sequences may be prepared using a PCR cloning techniques. This will involve making a pair of primers flanking a region of the sequence which it is desired to clone, bringing the primers into contact with mRNA or cDNA obtained from, for example, a mammalian (e.g. animal or human cell) or non-mammalian cell, performing a polymerase chain reaction (PCR) under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

The nucleotide sequence may be double-stranded or single-stranded whether representing the sense or antisense strand or combinations thereof.

For some aspects, it is preferred that the nucleotide sequence is single-stranded DNA—such as single stranded primers and probes.

For some aspects, it is preferred that the nucleotide sequence is double-stranded DNA—such as double stranded 3C and 4C templates.

For some aspects, it is preferred that the nucleotide sequence is genomic DNA—such as one or more genomic loci.

For some aspects, it is preferred that the nucleotide sequence is chromosomal DNA.

The nucleotide sequence may comprise a first (target) nucleotide sequence and/or a second nucleotide sequence.

The primary and secondary restriction enzyme recognition sites will be different to each other and will typically occur only once in the nucleotide sequence.

In one aspect, there is provided a circularised nucleotide sequence comprising a first nucleotide sequence and (e.g. ligated to) a second nucleotide sequence separated (e.g. divided or parted) by a primary and a secondary restriction enzyme recognition site, wherein said first nucleotide sequence is a target nucleotide sequence and said second nucleotide sequence is obtainable by cross-linking genomic DNA (e.g. in vivo or in vitro). The primary and secondary restriction enzyme recognition sites will be different to each other and will typically occur only once in the nucleotide sequence.

In a further aspect, there is provided a circularised nucleotide sequence comprising a first nucleotide sequence and (e.g. ligated to) a second nucleotide sequence separated (e.g. divided or parted) by a primary and a secondary restriction enzyme recognition site, wherein said first nucleotide sequence is a target nucleotide sequence and wherein said first and second nucleotide sequences are obtainable by a process comprising the steps of: (a) cross-linking genomic DNA (e.g. in vivo or in vitro); (b) digesting the cross-linked DNA with a primary restriction enzyme; (c) ligating the cross-linked nucleotide sequences; (d) reversing the cross linking; and (e) digesting the nucleotide sequences with a secondary restriction enzyme to circularise the nucleotide sequences.

Preferably, the second nucleotide sequence intersects (e.g. bisects) the first (target) nucleotide sequence. Accordingly, the nucleotide sequence comprises the second nucleotide sequence, which separates the first (target) nucleotide sequence into two portions or fragments—such as approximately two equally sized portions or fragments. Typically, the portions or fragments will be at least about 16 nucleotides in length.

First Nucleotide Sequence

The first nucleotide sequence is a target nucleotide sequence.

As used herein, the term "target nucleotide sequence" refers to the sequence that is used as a bait sequence in order to identify the one or more sequences to which it cross-links (e.g. one or more nucleotide sequences of interest or one or more sequences of unknown nucleotide sequence composition).

The target nucleotide sequence is of known sequence.

Cross-linking is indicative that the target nucleotide sequence and sequence cross-linked thereto were originally close in the nuclear space. By determining the frequency by which sequences are close to each other, it is possible to understand, for example, the conformation of chromosomes and chromosomal regions in the spatial context of the nucleus (e.g. in vivo or in vitro). Moreover, it is possible to understand the intricate structural organisations within the genome, for example, when enhancers or other transcriptional regulatory elements communicate with distant promoters located in cis or even in trans. Furthermore, it is even possible to understand the positioning of a given genomic region relative to nucleotide sequences present on the same chromosome (in cis) as well as to nucleotide sequences on other chromosomes (in trans). Thus, it is possible to map nucleotide sequences on different chromosomes that frequently share sites in the nuclear space. Furthermore, it is even possible to detect balanced and/or unbalanced genetic aberrations—such as balanced and/or unbalanced translocations, deletions, inversions, duplications and other genomic rearrangements (e.g. deletions or translocations in one or more chromosomes). In this regard, genetic aberrations result in changes in the DNA-DNA interactions at the position that the change has occurred, which can be detected.

The first (target) nucleotide sequence in accordance with the present invention can be any sequence in which it is desired to determine the frequency of interaction in the nuclear space with one or more other sequences.

In one embodiment, the first (target) nucleotide sequence will be greater than about 350 bp in length since a secondary restriction enzyme is chosen that cuts the first (target) nucleotide sequence at about 350 bp or more from the primary restriction site.

This may minimise a bias in circle formation due to topological constraints (Rippe et al. (2001) *Trends in Biochem. Sciences* 26, 733-40).

Suitably, the first (target) nucleotide sequence following amplification comprises at least about 32 bp virtue of the fact that the minimum length of the at least two amplification primers used to amplify the second nucleotide sequence are about 16 bases each.

In a preferred embodiment, the first (target) nucleotide sequence may comprise completely or partially (e.g. a fragment), or be close to (e.g. in the proximity of), a promoter, an enhancer, a silencer, an insulator, a matrix attachment region, a locus control region, a transcription unit, an origin of replication, a recombination hotspot, a translocation breakpoint, a centromere, a telomere, a gene-dense region, a gene-poor region, a repetitive element, a (viral) integration site, a nucleotide sequence in which deletions and/or mutations are related to an effect (e.g. disease, physiological, functional or structural effect—such as an SNP (single nucleotide polymorphism), or nucleotide sequence(s) containing such deletions and/or mutations, or any sequence in which it is desired to determine the frequency of interaction in the nuclear space with other sequences.

As mentioned above, the first (target) nucleotide sequence may comprise completely or partially (e.g. a fragment), or be close to (e.g. in the proximity of) a nucleotide sequence in which genetic aberrations—such as deletions and/or mutations—are related to an effect (e.g. a disease). According to this embodiment of the invention the first (target nucleotide sequence) may therefore be a nucleotide sequence (e.g. a gene or a locus), adjacent to (on the physical DNA template), or in the genomic region in which changes have been associated with or correlated to a disease—such as a genetic or congenital disease. In other words, the first (target) nucleotide sequence may be or may be chosen based on its association with a clinical phenotype. In a preferred embodiment, the changes are changes in one or more chromosomes and the disease may be as a consequence of, for example, one or more deletions, one or more translocations, one or more duplications, and/or one or more inversions etc therein.

Non-limiting examples of such genes/loci are AML1, MLL, MYC, BCL, BCR, ABL1, immunoglobulin loci, LYL1, TAL1, TAL2, LMO2, TCRα/δ, TCRβ, HOX and other loci in various lymphoblastic leukemias.

Other examples are described in electronic databases—such as:
http://www.ncbi.nlm.nih.gov/entrez/query.fcgi?db=cancerchromosomes
http://cgap.nci.nih.gov/Chromosomes/Mitelman
http://www.progenetix.net/progenetix/P14603437/ideogram.html
http://www.changbioscience.com/cytogenetics/cytol.pl?query=47,xy
http://www.possum.net.au/
http://www.lmdatabases.com/
http://www.wiley.com/legacy/products/subject/life/borgaonkar/index.html
http://www.ncbi.nlm.nih.gov/entrez/query.fcgi?db=OMIM
http://www.sanger.ac.uk/PostGenomics/decipher/
http://agserver01.azn.nl:8080/ecaruca/ecaruca.jsp Other examples are described in "Catalogue of Unbalanced Chromosome Aberrations in Man" 2nd edition. Albert Schinzel. Berlin: Walter de Gruyter, 2001. ISBN 3-11-011607-3.

In one embodiment, the term "adjacent" means "directly adjacent" such that there are no intervening nucleotides between two adjacent sequences.

In another embodiment, the term "adjacent" in the context of the nucleic acid sequence and the primary restriction enzyme recognition site means "directly adjacent" such that there are no intervening nucleotides between the nucleic acid sequence and the primary restriction enzyme recognition site.

Second Nucleotide Sequence

The second nucleotide sequence is obtainable, obtained, identified, or identifiable by cross-linking genomic DNA (e.g. in vivo or in vitro).

The second nucleotide sequence (e.g. nucleotide sequence of interest) becomes ligated to the first (target) nucleotide sequence after treating a sample with a cross-linking agent and digesting/ligating the cross-linked DNA fragments. Such sequences are cross-linked to the first (target) nucleotide sequence because they were originally close in the nuclear space and ligated to the first (target) nucleotide sequence because ligation conditions favour ligation between cross-linked DNA fragments (intramolecular) over random ligation events.

Diseases based on alterations—such as translocations, deletions, inversions, duplications and other genomic rearrangements—are generally caused by aberrant DNA-DNA interactions. 4C technology measures DNA-DNA interaction frequencies, which primarily are a function of the genomic site separation, i.e. DNA-DNA interaction frequencies are inversely proportional to the linear distance (in kilobases) between two DNA loci present on the same physical DNA template (Dekker et al., 2002). Thus, alteration(s) which create new and/or physically different DNA templates, is accompanied by altered DNA-DNA interactions and this can be measured by 4C technology.

Suitably, the second nucleotide sequence is at least 40 base pairs.

Cross-linking agents—such as formaldehyde—can be used to cross link proteins to other neighbouring proteins and nucleic acid. Thus, two or more nucleotide sequences can be cross-linked only via proteins bound to (one of) these nucleotide sequences. Cross-linking agents other than formaldehyde can also be used in accordance with the present invention, including those cross-linking agents that directly cross link nucleotide sequences. Examples of agents that cross-link DNA include, but are not limited to, UV light, mitomycin C, nitrogen mustard, melphalan, 1,3-butadiene diepoxide, cis diaminedichloroplatinum(II) and cyclophosphamide.

Suitably, the cross-linking agent will form cross-links that bridge relatively short distances—such as about 2 Å—thereby selecting intimate interactions that can be reversed.

Cross-linking may be performed by, for example, incubating the cells in 2% formaldehyde at room temperature—such as by incubating $1 \times 10^7$ cells in 10 ml of DMEM-10% FCS supplemented with 2% formaldehyde for 10 min at room temperature.

Primary Restriction Enzyme

As used herein, the term "primary restriction enzyme" refers to a first restriction enzyme that is used to digest the cross-linked DNA.

The primary restriction enzyme will be chosen depending on the type of target sequence (e.g. locus) to be analysed. It is desirable that preliminary experiments are performed to optimise the digestion conditions.

The primary restriction enzyme may be selected from restriction enzymes recognising at least 6 bp sequences or more of DNA.

Restriction enzymes that recognise 6 bp sequences of DNA include, but are not limited to, AclI, HindIII, SspI, BspLU11I, AgeI, MluI, SpeI, BglII, Eco47III, StuI, ScaI, ClaI, AvaIII, VspI, MfeI, PmaCI, PvuII, NdeI, NcoI, SmaI, SadI, AvrII, PvuI, XmaIII, SplI, XhoI, PstI, AflII, EcoRI, AatII, Sad, EcoRV, SphI, Nad, BsePI, NheI, BamHI, NarI, ApaI, KpnI, SnaI, SalI, ApaLI, HpaI, SnaBI, BspHI, BspMII, NruI, XbaI, BclI, MstI, BalI, Bsp1407I, PsiI, AsuII and AhaIII.

Restriction enzymes that recognise more than a 6 bp sequence of DNA include, but are not limited to BbvC I, AscI, AsiS I, Fse I, Not I, Pac I, Pme I, Sbf I, SgrA I, Swa I, Sap I, Cci NI, FspA I, Mss I, se I, Smi I, Srf I and Sse8387 I.

For some aspects of the present invention, in the case of restriction enzymes recognizing 6 bp sequences, BglII, HindIII or EcoRI are preferred.

The term "primary restriction enzyme recognition site" refers to the site in a nucleotide sequence that is recognised and cleaved by the primary restriction enzyme.

Secondary Restriction Enzyme

As used herein, the term "secondary restriction enzyme" refers to a second restriction enzyme that is used after primary restriction enzyme digestion, ligation of cross-linked DNA, de-cross-linking and (optional) DNA purification. In one embodiment, the secondary restriction enzyme is used to provide defined DNA ends to the nucleotide sequences of interest, which allows for the ligation of sequences of known nucleotide composition to the secondary restriction enzyme recognition sites that flank the nucleotide sequences of interest.

In one embodiment, ligation of sequences of known nucleotide composition to the secondary restriction enzyme recognition sites that flank (e.g. are at each side or end of) the nucleotide sequences of interest involves ligation under diluted conditions to favour the intra-molecular ligation between the secondary restriction enzyme recognition sites that flank target nucleotide sequences and the linked nucleotide sequences of interest. This effectively results in the formation of DNA circles in which known target nucleotide sequences flank unknown sequences of interest.

In another embodiment, ligation of sequences of known nucleotide composition to the secondary restriction enzyme recognition sites that flank (e.g. are at each side or end of) the nucleotide sequences of interest involves the addition of unique DNA sequences of known nucleotide composition, followed by ligation under conditions that favour inter-molecular ligation between the secondary restriction enzyme recognition sites that flank the nucleotide sequences of interest and introduced unique DNA sequences of known nucleotide composition.

In one embodiment, the secondary restriction enzyme is chosen such that no secondary restriction enzyme sites are within about 350 bp (e.g. 350-400 bp) of the primary restriction site.

In another embodiment, the secondary restriction enzyme is chosen such that the same secondary restriction enzyme site is likely to be located in the ligated nucleotide sequence (i.e. the ligated cross-linked sequence). Since the ends of the first (target) nucleotide sequence and the ligated nucleotide sequence may be compatible cohesive (or blunt) ends, the sequences may even be ligated in order to circularise the DNA. Accordingly, the digestion step is followed by ligation under diluted conditions that favour intra-molecular interactions and optional circularisation of the DNA via the compatible ends.

Preferably, the secondary restriction enzyme recognition site is a 4 or 5 bp nucleotide sequence recognition site. Enzymes that recognise 4 or 5 bp sequences of DNA include, but are not limited to, TspEI, MaeII, AluI, NlaIII, HpaII, FnuDII, MaeI, DpnI, MboI, HhaI, HaeIII, RsaI, TaqI, CviRI, MseI, Sth132I, AciI, DpnII, Sau3AI and MnlI.

In a preferred embodiment, the secondary restriction enzyme is NlaIII and/or DpnII.

The term "secondary restriction enzyme recognition site" refers to the site in the nucleotide sequence that is recognised and cleaved by the secondary restriction enzyme.

Following the digestion with the secondary restriction enzyme, a further ligation reaction is performed. In one embodiment, this ligation reaction links DNA sequences of known nucleotide sequence composition to the secondary restriction enzyme digestion site of the one or more sequences that are ligated to the target nucleotide sequence.

Tertiary Restriction Enzyme

As used herein, the term "tertiary restriction enzyme" refers to a third restriction enzyme that can be optionally used after the secondary restriction enzyme step in order to linearise circularised DNA prior to amplification.

Preferably, the tertiary restriction enzyme is an enzyme that recognises a 6 bp or more nucleotide recognition site.

Preferably, the tertiary restriction enzyme digests the first (target) nucleotide sequence between the primary and secondary restriction enzyme recognition sites. As will be understood by a skilled person, it is desirable that the tertiary restriction enzyme does not digest the first (target) nucleotide sequence too close to the primary and secondary restriction enzyme recognition sites such that the amplification primers can no longer hybridise. Accordingly, it is preferred that the tertiary restriction enzyme recognition site is located at least the same distance away from the primary and secondary restriction enzyme recognition sites as the length of the primer to be used such that the amplification primer(s) can still hybridise.

In a preferred embodiment, the tertiary restriction enzyme is one that recognises a 6-bp sequence of DNA.

The term "tertiary restriction enzyme recognition site" refers to the site in the nucleotide sequence that is recognised and cleaved by the tertiary restriction enzyme.

Recognition Site

Restriction endonucleases are enzymes that cleave the sugar-phosphate backbone of DNA. In most practical settings, a given restriction enzyme cuts both strands of duplex DNA within a stretch of just a few bases. The substrates for restriction enzymes are sequences of double-stranded DNA called recognition sites/sequences.

The length of restriction recognition sites varies, depending on the restriction enzyme that is used The length of the recognition sequence dictates how frequently the enzyme will cut in a sequence of DNA.

By way of example, a number of restriction enzymes recognise a 4 bp sequence of DNA. The sequences and the enzyme that recognise the 4 bp sequence of DNA include, but are not limited to, AATT (TspEI), ACGT (MaeII), AGCT (AluI), CATG (NlaIII), CCGG (HpaII); CGCG (FnuDII), CTAG (MaeI), GATC (DpnI, DpnII, Sau3AI & MboI), GCGC (HhaI), GGCC (HaeIII), GTAC (RsaI), TCGA (TaqI), TGCA (CviRI), TTAA (MseI), CCCG (Sth132I), CCGC (AciI) and CCTC (MnlI)

By way of further example, a number of restriction enzymes recognise a 6 bp sequence of DNA. The sequences and the enzyme that recognise the 6 base-pair by sequence of DNA include, but are not limited to, AACGTT (AcU), AAGCTT (HindIII), AATATT (SspI), ACATGT (BspLU11I), ACCGGT (AgeI), ACGCGT (MluI), ACTAGT (SpeI), AGATCT (BglII), AGCGCT (Eco47III), AGGCCT (StuI), AGTACT (ScaI), ATCGAT (ClaI), ATGCAT (AvaIII), ATTAAT (VspI), CAATTG (MfeI), CACGTG (PmaCI), CAGCTG (PvuII), CATATG (NdeI), CCATGG (NcoI), CCCGGG (SmaI), CCGCGG (SacII), CCTAGG (AvrII), CGATCG (PvuI), CGGCCG (XmaIII), CGTACG (SplI), CTCGAG (XhoI), CTGCAG (PstI), CTTAAG (AflII), GAATTC (EcoRI), GACGTC (AatII), GAGCTC (SacI), GATATC (EcoRV), GCATGC (SphI), GCCGGC (NaeI), GCGCGC (BsePI), GCTAGC (NheI), GGATCC (BamHI), GGCGCC (NarI), GGGCCC (ApaI), GGTACC (KpnI), GTATAC (SnaI), GTCGAC (SalI), GTGCAC (ApaLI), GTTAAC (HpaI), TACGTA (SnaBI), TCATGA (BspHI), TCCGGA (BspMII), TCGCGA (NruI), TCTAGA (XbaI), TGATCA (BclI), TGCGCA (MstI), TGGCCA (BalI), TGTACA (Bsp1407I), TTATAA (PsiI), TTCGAA (AsuII) and TITAAA (AhaIII).

By way of further example, a number of restriction enzymes recognise a 7 bp sequence of DNA. The sequences and the enzyme that recognise the 7 bp sequence of DNA include, but are not limited to CCTNAGG (SauI), GCINAGC (EspI), GGTNACC BstEII and TCCNGGA PfoI.

By way of further example, a number of restriction enzymes recognise an 8 bp sequence of DNA. The sequences and the enzyme that recognise the 8 bp sequence of DNA include, but are not limited to ATTTAAAT (SwaI), CCTGCAGG (Sse8387I), CGCCGGCG (Sse232I), CGTCGACG (SgrDI), GCCCGGGC (SrfI), GCGATCGC (SgfI), GCGGCCGC (NotI), GGCCGGCC (FseI), GGCGCGCC (AscI), GTTTAAAC (PmeI) and TTAATTAA (PacI).

A number of these enzymes contain the sequence CG that may be methylated in vivo. A number of restriction enzymes are sensitive to this methylation and will not cleave the methylated sequence, e.g. HpaII will not cleave the sequence CC$^m$GG whereas its isoschizomer MspI is insensitive to this modification and will cleave the methylated sequence. Accordingly, in some instances the eukaryotic methylation sensitive enzymes are not used.

In one embodiment, a recognition site is a digestion site.

In one embodiment, a restriction enzyme recognition site is a restriction enzyme digestion site.

Circularising

In accordance with one embodiment of the present invention, the material for 4C is prepared by creating DNA circles by digesting the 3C template with a secondary restriction enzyme, followed by ligation.

Preferably, a secondary restriction enzyme is chosen that cuts the first (target) nucleotide sequence at greater than about 350 bp (e.g. 350-400 bp) from the primary restriction site. Advantageously, this minimises a bias in circle formation due to topological constraints (Rippe et al. (2001) *Trends in Biochem. Sciences* 26, 733-40).

Preferably, the secondary restriction enzyme is a frequent cutter recognising a 4 or a 5 bp restriction enzyme recognition site. Thus it is possible to obtain the smallest restriction fragments for equal amplification efficiencies of all ligated fragments during amplification.

Prior to the secondary restriction enzyme digest and ligation, the DNA template will comprise one secondary enzyme recognition site in the first (target) nucleotide sequence located at greater than about 350-400 bp from the primary restriction site and another secondary enzyme recognition site located in the nucleotide sequence that has been ligated (ie in the second nucleotide sequence).

Preferably, the secondary restriction enzyme digestion step is performed for more than 1 hour to overnight and followed by heat-inactivation of the enzyme.

Preferably, the DNA in this reaction mixture is purified using conventional methods/kits that are known in the art.

Following the secondary restriction enzyme digestion step, a secondary restriction enzyme site will be located at greater than 350-400 bp from the primary restriction site in the first (target) nucleotide sequence and another secondary restriction enzyme site will be located in the ligated nucleotide sequence (i.e. the second nucleotide sequence). Since the ends of the first (target) nucleotide sequence and the ligated nucleotide sequence have compatible ends, the sequences can be ligated in order to circularise the DNA.

The digestion step is then followed by ligation under diluted conditions that favour intra-molecular interactions and circularisation of the DNA via the compatible ends.

Preferably, the ligation reaction is performed at a DNA concentration of about 1-5 ng/µl.

Preferably, the ligation reaction is performed for more than 1 hr (e.g. 2, 3, 4 or more hrs) at about 16-25° C.

Accordingly, following the ligation reaction, circularised DNA may be prepared. The circularised DNA will comprise the recognition sites for at least the secondary restriction enzyme or the primary and the secondary restriction enzymes. In circularised DNA containing the first (target) nucleotide sequence, the primary restriction enzyme recognition site and the secondary restriction enzyme recognition sites will define the ends of the first (target) nucleotide sequence and the ligated nucleotide sequence (i.e. the second nucleotide sequence). Accordingly the first (target) nucleotide sequence and the ligated nucleotide sequence are separated (e.g. divided) by the primary restriction enzyme recognition site and the secondary restriction enzyme recognition site.

Amplification

One or more amplification reactions may be performed in order to amplify the 4C DNA templates.

DNA amplification may be performed using a number of different methods that are known in the art. For example, DNA can be amplified using the polymerase chain reaction (Salki et al., 1988); ligation mediated PCR, Qb replicase amplification (Cahill, Foster and Mahan, 1991; Chetverin and Spirin, 1995; Katanaev, Kurnasov and Spirin, 1995); the ligase chain reaction (LCR) (Landegren et al., 1988; Barany, 1991); the self-sustained sequence replication system (Fahy, Kwoh and Gingeras, 1991) and strand displacement amplification (Walker et al., 1992).

Preferably, DNA is amplified using PCR. "PCR" refers to the method of K. B. Mullis U.S. Pat. Nos. 4,683,195, 4,683,202, and 4,965,188 that describe a method for increasing the concentration of a segment of a nucleotide sequence in a mixture of genomic DNA without cloning or purification.

In one embodiment, inverse PCR is used. Inverse PCR (IPCR) (described by Ochman et al (1988) *Genetics* 120(3), 621-3) is a method for the rapid in vitro amplification of DNA sequences that flank a region of known sequence. The method uses the polymerase chain reaction (PCR), but it has the primers oriented in the reverse direction of the usual orientation. The template for the reverse primers is a restriction fragment that has been ligated upon itself to form a circle. Inverse PCR has many applications in molecular genetics, for example, the amplification and identification of sequences flanking transposable elements. To increase the efficiency and reproducibility of the amplification it is preferred that the DNA circles are linearised before amplification using a tertiary restriction enzyme. Preferably, a tertiary restriction enzyme that is a 6 bp or more cutter is used. Preferably, the tertiary restriction enzyme cuts the first (target) nucleotide sequence between the primary and secondary restriction enzyme sites.

Digestion of the 3C template with the secondary restriction enzyme, optional circularisation, ligation (e.g. ligation under diluted conditions) and optional linearisation of first (target) nucleotide sequence-containing circles yields a DNA template for amplification ("4C DNA template").

For the amplification step, at least two oligonucleotide primers are used in which each primer hybridises to a DNA sequence that flanks the nucleotide sequences of interest. In a preferred embodiment, at least two oligonucleotide primers are used in which each primer hybridises to the target sequence flanking the nucleotide sequences of interest.

In one embodiment, the term "flank" in the context of primer hybridisation means that at least one primer hybridises to a DNA sequence adjacent one end (e.g. the 5' end) of the nucleotide sequence of interest and at least one primer hybridises to a DNA sequence at the other end (e.g. the 3' end) of the nucleotide sequence of interest. Preferably, at least one forward primer hybridises to a DNA sequence adjacent one end (e.g. the 5' end) of the nucleotide sequence of interest and at least one reverse primer hybridises to a DNA sequence at the other end. (e.g. the 3' end) of the nucleotide sequence of interest.

In a preferred embodiment, the term "flank" in the context of primer hybridisation means that at least one primer hybridises to a target sequence adjacent one end (e.g. the 5' end) of the nucleotide sequence of interest and at least one primer hybridises to a target sequence at the other end (e.g. the 3' end) of the nucleotide sequence of interest. Preferably, at least one forward primer hybridises to a target sequence adjacent one end (e.g. the 5' end) of the nucleotide sequence of interest and at least one reverse primer hybridises to a target sequence at the other end (e.g. the 3' end) of the nucleotide sequence of interest.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

Suitably, the primers will be at least 15, preferably at least 20, for example at least 25, 30 or 40 nucleotides in length. Preferably, the amplification primers are from 16 to 30 nucleotides in length.

Preferably, the primers are designed to be as close as possible to the primary and secondary restriction enzyme recognition sites that separate the first (target) nucleotide sequence and the second nucleotide sequence. The primers may be designed such that they are within about 100 nucleotides—such as about 90, 80, 70, 60, 50, 40, 30, 20, 10, 9, 8, 7, 6, 5, 4, 3, 2 or 1 nucleotide(s) away from the primary and secondary restriction enzyme recognition sites.

Suitably, the amplification primers are designed such that their 3' ends face outwards towards the primary and secondary restriction enzyme recognition sites so that extension proceeds immediately across the restriction sites into the second nucleotide sequence.

If the amplification method that is used is inverse PCR, then it is preferred that the amplification reactions are carried out on about 100-400 ng of DNA of 4C template (per about 50 µl PCR reaction mix) or other amounts of DNA for which replicate PCR reactions give reproducible results (see FIG. 1) and include a maximum number of ligation events per PCR reaction.

Preferably, the inverse PCR amplification reaction is performed using the Expand Long Template PCR System (Roche), using Buffer 1 according to the manufacturer's instructions.

Sample

The term "sample" as used herein, has its natural meaning. A sample may be any physical entity comprising DNA that is or is capable of being cross-linked. The sample may be or may be derived from biological material.

The sample may be or may be derived from one of more entities—such as one or more cells, one or more nuclei, or one or more tissue samples. The entities may be or may be derivable from any entities in which DNA—such as chromatin—is present. The sample may be or may be derived from one or more isolated cells or one or more isolated tissue samples, or one or more isolated nuclei.

The sample may be or may be derived from living cells and/or dead cells and/or nuclear lysates and/or isolated chromatin.

The sample may be or may be derived from diseased and/or non-diseased subjects.

The sample may be or may be derived from a subject that is suspected to be suffering from a disease.

The sample may be or may be derived from a subject that is to be tested for the likelihood that they will suffer from a disease in the future.

The sample may be or may be derived from viable or non-viable patient material.

The fixation of cells and tissues for use in preparing the 3C template is described in detail in Splinter et al., (2004) *Methods Enzymol.* 375, 493-507.

Label

Preferably, the nucleotide sequences (e.g. amplified 4C DNA templates, primers or probes etc.) are labelled in order to assist in their downstream applications—such as array hybridisation. By way of example, the 4C DNA templates may be labelled using random priming or nick translation.

A wide variety of labels (e.g. reporters) may be used to label the nucleotide sequences described herein, particularly during the amplification step. Suitable labels include radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241.

Additional labels include but are not limited to β-galactosidase, invertase, green fluorescent protein, luciferase, chloramphenicol, acetyltransferase, β-glucuronidase, exoglucanase and glucoamylase. Fluorescent labels may also be used, as well as fluorescent reagents specifically synthesised with particular chemical properties. A wide variety of ways to measure fluorescence are available. For example, some fluorescent labels exhibit a change in excitation or emission spectra, some exhibit resonance energy transfer where one fluorescent reporter looses fluorescence, while a second gains in fluorescence, some exhibit a loss (quenching) or appearance of fluorescence, while some report rotational movements.

In order to obtain sufficient material for labelling, multiple amplifications may be pooled, instead of increasing the number of amplification cycles per reaction. Alternatively, labelled nucleotides can be incorporated in to the last cycles of the amplification reaction (e.g. 30 cycles of PCR (no label)+10 cycles of PCR (plus label)).

Array

In a particularly advantageous embodiment, the 4C DNA templates that are prepared in accordance with the methods described herein can be hybridised to an array. Accordingly, array (e.g. micro-array) technology can be used to identify nucleotide sequences—such as genomic fragments—that frequently share a nuclear site with a first (target) nucleotide sequence.

Existing arrays—such as expression and genomic arrays—can be used in accordance with the present invention. However, the present invention also seeks to provide novel arrays (e.g. DNA arrays) as described herein.

An "array" is an intentionally created collection of nucleic acids which can be prepared either synthetically or biosynthetically and screened for biological activity in a variety of different formats (e.g., libraries of soluble molecules; and libraries of oligos tethered to resin beads, silica chips, or other solid supports). Additionally, the term "array" includes those libraries of nucleic acids which can be prepared by spotting nucleic acids of essentially any length (e.g., from 1 to about 1000 nucleotide monomers in length) onto a substrate.

Array technology and the various techniques and applications associated with it is described generally in numerous textbooks and documents. These include Lemieux et al., 1998, *Molecular Breeding* 4, 277-289, Schena and Davis. *Parallel Analysis with Biological Chips*. in *PCR Methods Manual* (eds. M. Innis, D. Gelfand, J. Sninsky), Schena and Davis, 1999, *Genes, Genomes and Chips*. In *DNA Microarrays: A Practical Approach* (ed. M. Schena), Oxford University Press, Oxford, UK, 1999), *The Chipping Forecast* (Nature Genetics special issue; January 1999 Supplement), Mark Schena (Ed.), *Microarray Biochip Technology*, (Eaton Publishing Company), Cortes, 2000, *The Scientist* 14[17]:25, Gwynn and Page, *Microarray analysis: the next revolution in molecular biology, Science*, 1999 Aug. 6; and Eakins and Chu, 1999, *Trends in Biotechnology*, 17, 217-218.

Array technology overcomes the disadvantages with traditional methods in molecular biology, which generally work on a "one gene in one experiment" basis, resulting in low throughput and the inability to appreciate the "whole picture" of gene function. Currently, the major applications for array technology include the identification of sequence (gene/gene mutation) and the determination of expression level (abundance) of genes. Gene expression profiling may make use of array technology, optionally in combination with proteomics techniques (Cells et al, 2000, *FEBS Lett,* 480(1):2-16; Lockhart and Winzeler, 2000, Nature 405(6788):827-836; Khan et al., 1999, 20(2):223-9). Other applications of array technology are also known in the art; for example, gene discovery, cancer research (Marx, 2000, Science 289: 1670-1672; Scherf, et al, 2000, Nat Genet; 24(3):236-44; Ross et al, 2000, Nat Genet. 2000 March; 24(3):227-35), SNP analysis (Wang et al, 1998, Science, 280(5366):1077-82), drug discovery, pharmacogenomics, disease diagnosis (for example, utilising microfluidics devices: Chemical & Engineering News, Feb. 22, 1999, 77(8):27-36), toxicology (Rockett and Dix (2000), *Xenobiotica*, 30(2):155-77; Afshari et al., 1999, Cancer Res1; 59(19):4759-60) and toxicogenomics (a hybrid of functional genomics and molecular toxicology).

In general, any library may be arranged in an orderly manner into an array, by spatially separating the members of the library. Examples of suitable libraries for arraying include nucleic acid libraries (including DNA, cDNA, oligonucleotide, etc libraries), peptide, polypeptide and protein libraries, as well as libraries comprising any molecules, such as ligand libraries, among others.

The samples (e.g., members of a library) are generally fixed or immobilised onto a solid phase, preferably a solid substrate, to limit diffusion and admixing of the samples. In a preferred embodiment, libraries of DNA binding ligands may be prepared. In particular, the libraries may be immobilised to a substantially planar solid phase, including membranes and non-porous substrates such as plastic and glass. Furthermore, the samples are preferably arranged in such a way that indexing (i.e., reference or access to a particular sample) is facilitated. Typically the samples are applied as spots in a grid formation. Common assay systems may be adapted for this purpose. For example, an array may be immobilised on the surface of a microplate, either with multiple samples in a well, or with a single sample in each well. Furthermore, the solid substrate may be a membrane, such as a nitrocellulose or nylon membrane (for example, membranes used in blotting experiments). Alternative substrates include glass, or silica based substrates. Thus, the samples are immobilised by any suitable method known in the art, for example, by charge interactions, or by chemical coupling to the walls or bottom of the wells, or the surface of the membrane. Other means of arranging and fixing may be used, for example, pipetting, drop-touch, piezoelectric means, ink-jet and bubblejet technology, electrostatic application, etc. In the case of silicon-based chips, photolithography may be utilised to arrange and fix the samples on the chip.

The samples may be arranged by being "spotted" onto the solid substrate; this may be done by hand or by making use of robotics to deposit the sample. In general, arrays may be described as macroarrays or microarrays, the difference being the size of the sample spots. Macroarrays typically contain sample spot sizes of about 300 microns or larger and may be easily imaged by existing gel and blot scanners. The sample spot sizes in microarrays are typically less than 200 microns in diameter and these arrays usually contain thousands of spots. Thus, microarrays may require specialized robotics and imaging equipment, which may need to be custom made Instrumentation is described generally in a review by Cortese, 2000, *The Scientist* 14[11]:26.

Techniques for producing immobilised libraries of DNA molecules have been described in the art. Generally, most prior art methods described how to synthesise single-stranded nucleic acid molecule libraries, using for example masking techniques to build up various permutations of sequences at the various discrete positions on the solid substrate. U.S. Pat. No. 5,837,832 describes an improved method for producing DNA arrays immobilised to silicon substrates based on very large scale integration technology. In particular, U.S. Pat. No. 5,837,832 describes a strategy called "tiling" to synthesise specific sets of probes at spatially-defined locations on a substrate which may be used to produced the immobilised DNA libraries of the present invention. U.S. Pat. No. 5,837,832 also provides references for earlier techniques that may also be used.

Arrays may also be built using photo deposition chemistry.

Arrays of peptides (or peptidomimetics) may also be synthesised on a surface in a manner that places each distinct library member (e.g., unique peptide sequence) at a discrete, predefined location in the array. The identity of each library member is determined by its spatial location in the array. The locations in the array where binding interactions between a predetermined molecule (e.g., a target or probe) and reactive library members occur is determined, thereby identifying the sequences of the reactive library members on the basis of spatial location. These methods are described in U.S. Pat. No. 5,143,854; WO90/15070 and WO92/10092; Fodor et al. (1991) *Science*, 251: 767; Dower and Fodor (1991) *Ann. Rep. Med. Chem.*, 26: 271.

To aid detection, labels are typically used (as discussed above)—such as any readily detectable reporter, for example, a fluorescent, bioluminescent, phosphorescent, radioactive, etc reporter. Such reporters, their detection, coupling to targets/probes, etc are discussed elsewhere in this document. Labelling of probes and targets is also disclosed in Shalon et al., 1996, *Genome Res* 6(7):639-45.

Specific examples of DNA arrays are as follow:

Format I: probe cDNA (500~5,000 bases long) is immobilized to a solid surface such as glass using robot spotting and exposed to a set of targets either separately or in a mixture. This method is widely considered as having been developed at Stanford University (Ekins and Chu, 1999, *Trends in Biotechnology*, 1999, 17, 217-218).

Format II: an array of oligonucleotides (20-25-mer oligos, preferably, 40-60 mer oligos) or peptide nucleic acid (PNA) probes are synthesised either in situ (on-chip) or by conventional synthesis followed by on-chip immobilization. The array is exposed to labelled sample DNA, hybridised, and the identity/abundance of complementary sequences are determined. Such a DNA chip is sold by Affymetrix, Inc., under the GeneChip® trademark. Agilent and Nimblegen also provide suitable arrays (e.g. genomic tiling arrays).

Examples of some commercially available microarray formats are set out in Table 1 below (see also Marshall and Hodgson, 1998, *Nature Biotechnology*, 16(1), 27-31).

TABLE 1

Examples of currently available hybridization microarray formats

| Company | Product name | Arraying method | Hybridization step | Readout |
|---|---|---|---|---|
| Affymetrix, Inc., Santa Clara, California | GeneChip ® | In situ (on-chip) photolithographic synthesis of ~20-25-mer oligos onto silicon wafers, which are diced into 1.25 cm² or 5.25 cm² chips | 10,000-260,000 oligo features probed with labeled 30-40 nucleotide fragments of sample cDNA or antisense RNA | Fluorescence |
| Brax, Cambridge, UK | | Short synthetic oligo, synthesized off-chip | 1000 oligos on a "universal chip" probed with tagged nucleic acid | Mass spectrometry |
| Gene Logic, Inc., Columbia, Maryland | READS ™ | | | |
| Genometrix Inc., The Woodlands, Texas | Universal Arrays ™ | | | |
| GENSET, Paris, France | | | | |
| Hyseq Inc., Sunnyvale, California | HyChip ™ | 500-2000 nt DNA samples printed onto 0.6 cm² (HyGnostics) or ~18 cm² (Gene Discovery) membranes | 64 sample cDNA spots probed with 8,000 7-mer oligos (HyGnostics) or <=55,000 sample cDNA spots probed with 300 7-mer oligo (Gene Discovery) | Radioisotope |
| | | Fabricated 5-mer oligos printed as 1.15 cm² arrays onto glass (HyChip) | Universal 1024 oligo spots probed 10 kb sample cDNAs, labeled 5-mer oligo, and ligase | Fluorescence |

TABLE 1-continued

Examples of currently available hybridization microarray formats

| Company | Product name | Arraying method | Hybridization step | Readout |
|---|---|---|---|---|
| Incyte Pharmaceuticals, Inc., Palo Alto, California | GEM | Piezoelectric printing for spotting PCR fragments and on-chip synthesis of oligos | <=1000 (eventually 10,000) oligo/PCR fragment spots probed with labeled RNA | Fluorescence and radioisotope |
| Molecular Dynamics, Inc., Sunnyvale, California | Storm ® FluorImager ® | 500-5000 nt cDNAs printed by pen onto ~10 cm² on glass slide | ~10,000 cDNA spots probed with 200-400 nt labeled sample cDNAs | Fluorescence |
| Nanogen, San Diego, California | Semiconductor Microchip | Prefabricated ~20-mer oligos, captured onto electroactive spots on silicon wafers, which are diced into <=1 cm² chips | 25, 64, 400 (and eventually 10,000) oligo spots polarized to enhance hybridization to 200-400 nt labeled sample cDNAs | Fluorescence |
| Protogene Laboratories, Palo Alto, California | | On-chip synthesis of 40-50-mer oligos onto 9 cm² glass chip via printing to a surface-tension array | <=8,000 oligo spots probed with 200-400 nt labeled sample nucleic acids | Fluorescence |
| Sequenom, Hamburg, Germany, and San Diego, California | MassArray SpectroChip | Off-set printing of array; around 20-25-mer oligos | 250 locations per SpectroChip interrogated by laser desorbtion and mass spectrometry | Mass spectrometry |
| Synteni, Inc., Fremont, California | UniGEM ™ | 500-5,000 nt cDNAs printed by tip onto ~4 cm² glass chip | <=10,000 cDNA spots probed with 200-400 nt labeled sample cDNAs | Fluorescence |
| Nimblegen Systems Inc., Madison | *Homo sapiens* Whole-Genome 60mer Microarray | 38,000 transcripts with 5 probes per gene 17.4 mm × 13 mm | | 5-micron scanning platform |
| The German Cancer Institute, Heidelberg, Germany | | Prototypic PNA macrochip with on-chip synthesis of probes using f-moc or t-moc chemistry | Around 1,000 spots on a 8 × 12 cm chip | Fluorescence/mass spectrometry |

In order to generate data from array-based assays a signal is detected that signifies the presence of or absence of hybridisation between a probe and a nucleotide sequence. The present invention further contemplates direct and indirect labelling techniques. For example, direct labelling incorporates fluorescent dyes directly into the nucleotide sequences that hybridise to the array associated probes (e.g., dyes are incorporated into nucleotide sequence by enzymatic synthesis in the presence of labelled nucleotides or PCR primers). Direct labelling schemes yield strong hybridisation signals, typically using families of fluorescent dyes with similar chemical structures and characteristics, and are simple to implement. In preferred embodiments comprising direct labelling of nucleic acids, cyanine or alexa analogs are utilised in multiple-fluor comparative array analyses. In other embodiments, indirect labelling schemes can be utilised to incorporate epitopes into the nucleic acids either prior to or after hybridisation to the microarray probes. One or more staining procedures and reagents are used to label the hybridised complex (e.g., a fluorescent molecule that binds to the epitopes, thereby providing a fluorescent signal by virtue of the conjugation of dye molecule to the epitope of the hybridised species).

Data analysis is also an important part of an experiment involving arrays. The raw data from an array experiment typically are images, which need to be transformed into matrices—tables where rows represent for example genes, columns represent for example various samples such as tissues or experimental conditions, and numbers in each cell for example characterise the expression of a particular sequence (preferably, a second sequence that has ligated to the first (target) nucleotide sequence) in the particular sample. These matrices have to be analysed further, if any knowledge about the underlying biological processes is to be extracted. Methods of data analysis (including supervised and unsupervised data analysis as well as bioinformatics approaches) are disclosed in Brazma and Vilo J (2000) FEBS Lett 480(1):17-24.

As described herein the one or more nucleotide sequences (e.g. the DNA template) that are labelled and subsequently hybridised to an array comprises a nucleotide sequence that is enriched for small stretches of sequences with a distinct signature i.e. spanning the nucleotide sequence between the primary restriction enzyme recognition site that was ligated during the 3C procedure to the first (target) nucleotide sequence, and their respective neighbouring secondary restriction enzyme recognition sites.

A single array may comprise multiple (e.g. two or more) bait sequences.

Probes

As used herein, the term "probe" refers to a molecule (e.g., an oligonucleotide, whether occurring naturally as in a purified restriction digest or produced synthetically, recombinantly or by PCR amplification), that is capable of hybridising to another molecule of interest (e.g., another oligonucleotide). When probes are oligonucleotides they may be single-stranded or double-stranded. Probes are useful in the detection, identification and isolation of particular targets (e.g., gene sequences). As described herein, it is contemplated that probes used in the present invention may be labelled with a label so that is detectable in any detection system, including, but not limited to enzyme (e.g., ELISA, as well as enzyme-based histochemical assays), fluorescent, radioactive, and luminescent systems.

With respect to arrays and microarrays, the term "probe" is used to refer to any hybridisable material that is affixed to the array for the purpose of detecting a nucleotide sequence that has hybridised to said probe. Preferably, these probes are 25-60 mers or longer.

Strategies for probe design are described in WO95/11995, EP 717,113 and WO97/29212.

Since 4C allows an unbiased genome-wide search for interactions, it is advantageous to prepare an array with probes interrogating every possible (e.g. unique/non-repetitive) primary restriction enzyme recognition site in the genome. Thus, array design only depends on the choice of primary restriction enzyme and not on the actual first or secondary nucleotide sequences.

Whilst existing arrays can be used in accordance with the present invention, it is preferred to use alternative configurations.

In one configuration, one or more probes on the array are designed such that they can hybridise close to the sites that are digested by the primary restriction enzyme. More preferably, the probe(s) are within about 20 bp of the primary restriction enzyme recognition site. More preferably, the probe(s) are within about 50 bp of the primary restriction enzyme recognition site.

Suitably, the probe(s) are within about 100 bp (e.g. about 0-100 bp, about 20-100 bp) of the primary restriction enzyme recognition site.

In a preferred configuration, a single, unique, probe is designed within 100 bp at each side of the sites that are digested by the primary restriction enzyme.

In another preferred configuration, the positions of sites digested by the secondary restriction enzyme relative to the positions of sites digested by the primary restriction sites are taken into account. In this configuration, a single, unique, probe is designed only at each side of the sites digested by the primary restriction enzyme that have the nearest secondary restriction enzyme recognition site at a distance large enough for a probe of a given length to be designed in between the primary and secondary restriction enzyme recognition site. In this configuration, for example, no probe is designed at the side of a particular primary restriction enzyme recognition site that has a secondary restriction enzyme recognition site within 10 bp at that same side.

In another configuration, the probes on the array are designed such that they can hybridise at either side of the sites that are digested by the primary restriction enzyme. Suitably, a single probe at each side of the primary restriction enzyme recognition site can be used.

In yet another configuration, two or more probes (e.g. 3, 4, 5, 6, 7 or 8 or more) can be designed at each side of the primary restriction enzyme recognition site, which can then be used to investigate the same ligation event. For the number and position of probes relative to each primary restriction enzyme recognition site, the exact genomic location of its neighbouring secondary restriction enzyme recognition site can be taken into account.

In yet another configuration, two or more probes (e.g. 3, 4, 5, 6, 7 or 8 or more) can be designed near each primary restriction enzyme recognition site irrespective of the nearest secondary restriction enzyme recognition site. In this configuration, all probes should still be close to the primary restriction enzyme recognition sites (preferably within 300 bp of the restriction site).

Advantageously, the latter design and also the design that uses 1 probe per (side of a) primary restriction enzyme recognition site, allows the use of different secondary restriction enzymes in combination with a given primary restriction enzyme.

Advantageously, the use of multiple (e.g. 2, 3, 4, 5, 6, 7 or 8 or more) probes per primary restriction enzyme recognition site can minimise the problem of obtaining false negative results due to poor performance of individual probes. Moreover, it can also increase the reliability of data obtained with a single chip experiment and reduce the number of arrays required to draw statistically sound conclusions.

The probes for use in the array may be greater than 40 nucleotides in length and may be iso-thermal.

Preferably, probes containing repetitive DNA sequences are excluded.

Probes diagnostic for the restriction sites that directly flank or are near to the first nucleotide sequence are expected to give very strong hybridisation signals and may also be excluded from the probe design.

The array may cover any genome including mammalian (e.g. human, mouse (e.g. chromosome 7)), vertebrate (e.g. zebrafish)), or non-vertebrate (e.g. bacterial, yeast, fungal or insect (e.g. *Drosophila*)) genomes.

In a further preferred embodiment, the array contains 2-6 probes around every unique primary restriction site and as close as possible to the site of restriction enzyme digestion.

Preferably, the maximum distance from the site of restriction enzyme digestion is about 300 bp.

In a further preferred embodiment of the present invention, arrays for restriction enzymes—such as HindIII, EcoRI, BclI and NotI—that cover the mammalian or non-mammalian genomes are provided. Advantageously, the design of the arrays described herein circumvent the need to re-design arrays for every target sequence, provided analysis is performed in the same species.

Sets of Probes

As used herein, the term "set of probes" refers to a suite or a collection of probes that hybridise to each one of the primary restriction enzyme recognition sites for a primary restriction enzyme in a genome.

Accordingly, there is provided in a further aspect, a set of probes complementary in sequence to the nucleic acid sequence adjacent to each one of the primary restriction enzyme recognition sites for a primary restriction enzyme in genomic DNA.

Suitably, the set of probes are complementary in sequence to the first 25-60 (e.g. 35-60, 45-60, or 50-60) or more nucleotides that are adjacent to each one of the primary restriction enzyme recognition sites in genomic DNA. The set of probes may be complementary in sequence to one (e.g. either) side or both sides of the primary restriction enzyme recognition site. Accordingly, the probes may be complementary in sequence to the nucleic acid sequence adjacent each side of each one of the primary restriction enzyme recognition sites in the genomic DNA.

It is also possible to define a window (e.g. 300 bp or less—such as 250 bp, 200 bp, 150 bp or 100 bp—from the primary restriction enzyme recognition site) in which one or more probes for the set can be designed. Such factors that are important in defining the window within which to design the probes are, for example, GC-content, absence of palindromic sequences that can form hairpin structures, maximum size to stretches of a single type of nucleotide. Accordingly, the set of probes can be complementary in sequence to the nucleic acid sequence that is less than 300 bp from each one of the primary restriction enzyme recognition sites in genomic DNA.

It is also possible to define a window of about 100 bp from the primary restriction enzyme recognition site in order to identify optimal probes near each restriction site.

In further embodiments of the present invention, the set of probes are complementary to the sequence that is less then 300 bp from each one of the primary restriction enzyme recognition sites in genomic DNA, complementary to the sequence that is between 200 and 300 bp from each one of the primary restriction enzyme recognition sites in genomic DNA and/or complementary to the sequence that is between 100 and 200 bp from each one of the primary restriction enzyme recognition sites in genomic DNA.

In further embodiments of the present invention, the set of probes are complementary to the sequence that is from 0 to 300 bp from each one of the primary restriction enzyme recognition sites in genomic DNA, complementary to the sequence that is between 0 to 200 bp from each one of the primary restriction enzyme recognition sites in genomic DNA and/or complementary to the sequence that is between 0 to 100 bp from each one of the primary restriction enzyme recognition sites in genomic DNA (e.g. about 10, 20, 30, 40, 50, 60, 70, 80 or 90 bp from each one of the primary restriction enzyme recognition sites in genomic DNA).

Two or more probes may even be designed that are capable of hybridising to the sequence adjacent each primary restriction enzyme recognition site in the genomic DNA.

The probes may overlap or partially overlap. If the probes overlap then the overlap is preferably, less than 10 nucleotides.

PCR fragments representing the first 1-300 nucleotides (e.g. 1-20, 1-40, 1-60, 1-80, 1-100, 1-120, 1-140, 1-160, 1-180, 1-200, 1-220, 1-240, 1-260 or 1-280 nucleotides) that flank each primary restriction enzyme recognition site can also be used.

PCR fragments may also be used as probes that exactly correspond to each genomic site that is flanked by the primary restriction enzyme recognition site and the first neighboring second restriction enzyme recognition site. Accordingly, the probe sequence may correspond to all or part of the sequence between each one of the primary restriction enzyme recognition sites and each one of the first neighbouring secondary restriction enzyme recognition sites.

Typically, the probes, array of probes or set of probes will be immobilised on a support. Supports (e.g. solid supports) can be made of a variety of materials—such as glass, silica, plastic, nylon or nitrocellulose. Supports are preferably rigid and have a planar surface. Supports typically have from about 1-10,000,000 discrete spatially addressable regions, or cells. Supports having about 10-1,000,000 or about 100-100,000 or about 1000-100,000 cells are common. The density of cells is typically at least about 1000, 10,000, 100,000 or 1,000,000 cells within a square centimeter. In some supports, all cells are occupied by pooled mixtures of probes or a set of probes. In other supports, some cells are occupied by pooled mixtures of probes or a set of probes, and other cells are occupied, at least to the degree of purity obtainable by synthesis methods, by a single type of oligonucleotide.

Preferably, the array described herein comprises more than one probe per primary restriction enzyme recognition site, which in the case of a 6 bp cutting restriction enzyme occurs, for example, approximately 750,000 times per human or mouse genome.

For a restriction enzyme recognising a >6 bp recognition sequence, a single array of about 2×750,000 probes can be used to cover, for example, the complete human or mouse genome, with 1 probe at each side of each restriction site.

In a preferred array design, the total number of probe molecules of a given nucleotide sequence present on the array is in large excess to homologous fragments present in the 4C sample to be hybridized to such array. Given the nature of 4C technology, fragments representing genomic regions close to the analyzed nucleotide sequence on the linear chromatin template will be in large excess in the 4C hybridization sample (as described in FIG. 2). To obtain quantitative information about hybridization efficiencies of such abundant fragments, it may be necessary to reduce the amount of sample to be hybridized and/or increase the number of molecules of a given oligonucleotide sequence probe on the array.

Thus, for the detection of regulatory DNA elements that frequently contact, for example, a gene promoter element it may be necessary to use an array with probes that represent only the selected genomic region (e.g. about 0.5-10 Mb), but with each unique probe present at multiple (e.g. about 100, 200, 1000) positions on the array. Such designs may also be preferred for diagnostic purposes to detect local (e.g. within about 10 Mb) genomic rearrangements—such as deletions, inversions, duplications, etc.—around a site (e.g. gene of interest).

The array may comprise about 3×750,000 probes, 4×750,000 probes, 5×750,000 probes, or preferably, 6×750,000 probes. More preferably, the array comprises 6×750,000 probes with 2, 3, 4, 5, 6, 7 or 8 or more probes at each side of each restriction site. Most preferably, the array comprises 6×750,000 probes with 3 probes at each side of each restriction site.

Arrays of probes or sets of probes may be synthesised in a step-by-step manner on a support or can be attached in presynthesized form. One method of synthesis is VLSIPS™ (as described in U.S. Pat. No. 5,143,854 and EP 476,014), which entails the use of light to direct the synthesis of oligonucleotide probes in high-density, miniaturised arrays. Algorithms for design of masks to reduce the number of synthesis cycles are described in U.S. Pat. No. 5,571,639 and U.S. Pat. No. 5,593,839. Arrays can also be synthesised in a combinatorial fashion by delivering monomers to cells of a support by mechanically constrained flowpaths, as described in EP 624,059. Arrays can also be synthesised by spotting reagents on to a support using an ink jet printer (see, for example, EP 728,520).

In the context of the present invention, the terms "substantially a set of probes" "substantially the array of probes" means that the set or the array of probes comprises at least about 50, 60, 70, 80, 90, 95, 96, 97, 98 or 99% of the full or complete set or array of probes. Preferably, the set or the array of probes is a full or complete set of probes (i.e. 100%).

In a preferred embodiment, the array comprises a single unique probe per side of each primary restriction enzyme recognition site that is present in a given genome. If this number of probes exceeds the number of probes that can be contained by a single array, the array may preferably still contain a representation of the complete genome of a given species, but at lower resolution, with for example one out of every 2, 3, 4, 5, 6, 7, 8, 9, 10, $10^2$, $10^3$ or $10^4$ etc. probes as ordered on the linear chromosome template present on the array. Such arrays that cover the complete human, or other, genome at sub-optimal resolution may be preferred over high-resolution arrays that cover part of the same genome, for example in cases where translocation partners are to be found.

Preferably, the representation of the complete genome of a given species at lower resolution is obtained by probes on the array that each represent a single restriction fragment as obtained after digestion with a primary restriction enzyme. Preferably, this is obtained by ignoring every second, third, fourth, fifth, sixth, seventh, eighth, ninth, tenth, twentieth, thirtieth, fortieth, fiftieth, sixtieth, seventieth, eightieth, ninetieth or one hundredth etc. probe that hybridises to the same restriction fragment.

Preferably, the representation of the complete genome of a given species at lower resolution comprises probes that are distributed equally along the linear chromosome templates. Preferably, this is obtained by ignoring one or more probes in those genomic regions that show highest probe density.

Hybridisation

The term "hybridisation" as used herein shall include "the process by which a strand of nucleic acid joins with a complementary strand through base pairing" as well as the process of amplification as carried out in, for example, polymerase chain reaction (PCR) technologies.

Nucleotide sequences capable of selective hybridisation will be generally be at least 75%, preferably at least 85 or 90% and more preferably at least 95% or 98% homologous to the corresponding complementary nucleotide sequence over a region of at least 20, preferably at least 25 or 30, for instance at least 40, 60 or 100 or more contiguous nucleotides.

"Specific hybridisation" refers to the binding, duplexing, or hybridising of a molecule only to a particular nucleotide sequence under stringent conditions (e.g. 65° C. and 0.1×SSC {1×SSC=0.15 M NaCl, 0.015 M Na-citrate pH 7.0}). Stringent conditions are conditions under which a probe will hybridise to its target sequence, but to no other sequences. Stringent conditions are sequence-dependent and are different in different circumstances. Longer sequences hybridise specifically at higher temperatures. Generally, stringent conditions are selected to be about 5° C. lower than the thermal melting point (Tm) for the specific sequence at a defined ionic strength and pH. The Tm is the temperature (under defined ionic strength, pH, and nucleic acid concentration) at which 50% of the probes complementary to a target sequence hybridise to the target sequence at equilibrium. (As the target sequences are generally present in excess, at Tm, 50% of the probes are occupied at equilibrium). Typically, stringent conditions include a salt concentration of at least about 0.01 to 1.0 M Na ion concentration (or other salts) at pH 7.0 to 8.3 and the temperature is at least about 30° C. for short probes. Stringent conditions can also be achieved with the addition of destabilising agents—such as formamide or tetraalkyl ammonium salts.

As will be understood by those of skill in the art, a maximum stringency hybridisation can be used to identify or detect identical nucleotide sequences while an intermediate (or low) stringency hybridization can be used to identify or detect similar or related polynucleotide sequences.

Methods are also described for the hybridisation of arrays of probes to labelled or unlabeled nucleotide sequences. The particular hybridisation reaction conditions can be controlled to alter hybridisation (e.g., increase or decrease probe/target binding stringency). For example, reaction temperature, concentrations of anions and cations, addition of detergents, and the like, can all alter the hybridisation characteristics of array probes and target molecules.

Frequency of Interaction

Quantifying ligation frequencies of restriction fragments gives a measure of their cross-linking frequencies. Suitably, this can be achieved using PCR as used in conventional 3C technology as described by Splinter et al. (2004) (supra). Briefly, the formation of PCR products can be measured by scanning the signal intensities after separation on ethidium bromide stained agarose gels, using a Typhoon 9200 imager (Molecular Dynamics, Sunnyvale, Calif.). Suitably, several controls are used for the correct interpretation of data as also described in Splinter et al. (2004) (supra).

Since the 4C technology described herein provides for the high-throughput analysis of the frequency of interaction of two or more nucleotide sequences in the nuclear space, it is preferred that the ligation frequencies of restriction fragments are quantified using the arrays described herein.

For quantitation, signals obtained for a 4C sample can be normalised to signals obtained for a control sample. 4C sample and control sample(s) will be labelled with different and discernable labels (e.g. dyes) and will be simultaneously hybridised to the array. Control sample(s) will typically contain all DNA fragments (i.e. all potential second nucleotide sequences that have ligated to the first (target) nucleotide sequence) in equimolar amounts and, to exclude a bias in hybridisation efficiency, they should be similar in size to the second nucleotide sequence(s). Thus, control template will typically contain genomic DNA (of the same genetic background as that used to obtain the 4C template), digested with both the primary and the secondary restriction enzyme and labelled by the same method (e.g. random priming) as the 4C template. Such control template makes it possible to correct for probe-to-probe differences in hybridisation efficiency. Normalising 4C array signals to control array signals makes it possible to express results in terms of enrichment over random events.

Labeled 4C template may even be hybridized to an array with or without a differentially labeled control sample and with or without one or more differentially labeled other 4C templates. Other 4C templates can be unrelated to this 4C template, for example it may be obtained from different tissue and/or obtained with a different set of inverse PCR primers. For example, the first 4C template may be patient material and the second 4C template may be obtained from a healthy subject or a control sample.

Given the striking hybridisation patterns that are to be expected for genetic rearrangements it will not always be necessary to compare diseased subjects with healthy subjects. Accordingly, multiple (e.g. two or more) 4C templates, each interrogating a different locus from the same patient or subject may be hybridized to one (e.g. one or more) array.

The 4C templates may be differentially labeled (e.g. with two or multi-color hybridization) and/or may be identically labeled in case such loci normally reside on different chromosomes or on the same chromosome at a distance far enough for minimal overlap between DNA-DNA interaction signals. As an example, material from a subject with T-cell leukemia may be processed to obtain 4C templates for TCRα/δ (labeled in one color, in order to detect translocations), and MLL, TAL1, HOX11 and LMO2 (each labeled in the same second color, in order to detect other genetic rearrangements). These five 4C templates may be hybridized to one array, which will allow the simultaneous analysis at multiple loci for a genomic rearrangement associated with the disease.

For quantification of interaction frequencies, absolute signal intensities or ratios over control sample may also be considered. In addition, signals of probes adjacent on the linear chromosome template may be used to identify interacting chromosomal regions. Such positional information is preferably analyzed by ordering the probes on the linear chromosome template and analysing the absolute signal intensities, or ratios over control template signals, by sliding window approaches, using for example running mean or miming median approaches.

Assay Method

In a further aspect of the present invention, there is a provided an assay method for identifying one or more agents that modulate a DNA-DNA interaction.

As used herein, the term "modulate" refers to preventing, decreasing, suppressing, restorating, elevating, increasing or otherwise affecting the DNA-DNA interaction.

In some cases, it may be desirable to evaluate two or more agents together for use in modulating the DNA-DNA interaction. In these cases, assays may be readily modified by adding such additional agent(s) either simultaneously with, or subsequently to, the first agent.

The method of the present invention may also be a screen, whereby a number of agents are tested for modulating the activity of the DNA-DNA interaction.

It is expected that the assay methods of the present invention will be suitable for both small and large-scale screening of agents as well as in quantitative assays.

Medical uses of such therapeutic agents are within the scope of the present invention as are the drug development programs themselves and pharmaceutical compositions comprising such agents. A drug development program may, for example, involve taking an agent identified or identifiable by the methods described herein, optionally modifying it (e.g. modifying its structure and/or providing a novel composition comprising said moiety) and performing further studies (e.g. toxicity studies and/or studies on activity, structure or function). Trials may be performed on non-human animals and may eventually be performed on humans. Such trials will generally include determining the effects) of different dosage levels. Drug development programs may utilise computers to analyse moieties identified by screening (e.g. to predict structure and/or function, to identify possible agonists or antagonists, to search for other moieties that may have similar structures or functions, etc.).

Diagnostic Testing

Currently, various genomic rearrangements remain difficult to detect by available molecular-cytogenetic techniques. Although the array comparative genomic hybridization technique (array-CGH) is a newly developed technique for the detection of chromosomal amplification and/or deletions with a resolution of 35-300 Kb, this technique is not suitable to detect balanced translocations and chromosomal inversions. On the other hand, spectral karyotyping (SKY) or conventional karyotyping is often performed on patient material for the detection of chromosomal translocations as well as numerical changes, but the resolution to define translocation breakpoints is low, usually 10-50 Mb and 5-10 Mb, respectively. Consequently, results obtained by both methods and especially SKY will lead to time-consuming and labor-intensive validations experiments like fluorescence in situ hybridization (FISH) and molecular breakpoint cloning strategies.

4C technology involves a procedure that can detect any chromosomal rearrangements on the basis of changed interaction frequencies between physically linked DNA sequences. 4C technology is therefore useful for the identification of (recurrent) chromosomal rearrangements for most human malignancies/multiple congenital malformations or mental retardation. An important advantage of 4C technology is that it allows for the very accurate mapping of the breakpoint to a region of only several thousands of basepairs. Another advantage of 4C technology is that no prior knowledge is required on the exact position of the breakpoint, since breakpoints will be detectable even when the 4C-bait sequence is located 1-5 Mb away from the breakpoint. This has also the advantage that the same bait sequence can be used for the detection of specific chromosomal rearrangements covering large breakpoint areas. The accurate mapping of genomic rearrangements by 4C technology will greatly facilitate the identification of aberrantly expressed gene(s) underlying diseases or genetic disorders, which will importantly contribute to a better understanding of the genotype-phenotype correlations, assist in treatment decision-making and add important prognostic information.

In one embodiment of the present invention, in order to provide a basis for the diagnosis or prognosis of disease, normal or standard values from a subject are established. This may be accomplished by testing samples taken from normal subjects—such as animals or humans. The frequency of the DNA-DNA interaction may be quantified by comparing it to a dilution series of positive controls. Then, standard values obtained from normal samples may be compared with values obtained from samples from subjects affected or potentially affected by a disease or a disorder. Deviation between standard and subject values establishes the presence of the disease state.

Such diagnostic assays may be tailored to evaluate the efficacy of a particular therapeutic treatment regime and may be used in animal studies, in clinical trials, or in monitoring the treatment of an individual patient. In order to provide a basis for the diagnosis of disease, a normal or standard profile for the DNA-DNA interaction may be established. Standard values obtained from normal samples may be compared with values obtained from samples from subjects potentially affected by a disorder or disease. Deviation between standard and subject values establishes the presence of the disease state. If disease is established, an existing therapeutic agent may be administered, and treatment profile or values may be generated. Finally, the method may be repeated on a regular basis to evaluate whether the values progress toward or return to the normal or standard pattern. Successive treatment profiles may be used to show the efficacy of treatment over a period of several days or several months.

Figure 2B:
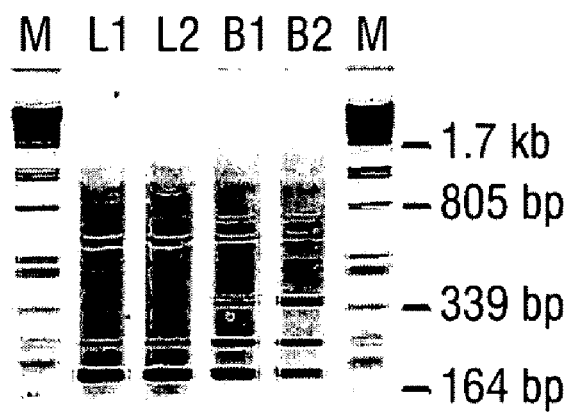
Figure 2C:
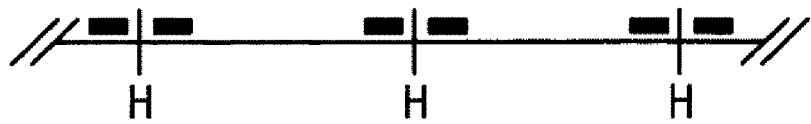
Figure 3:
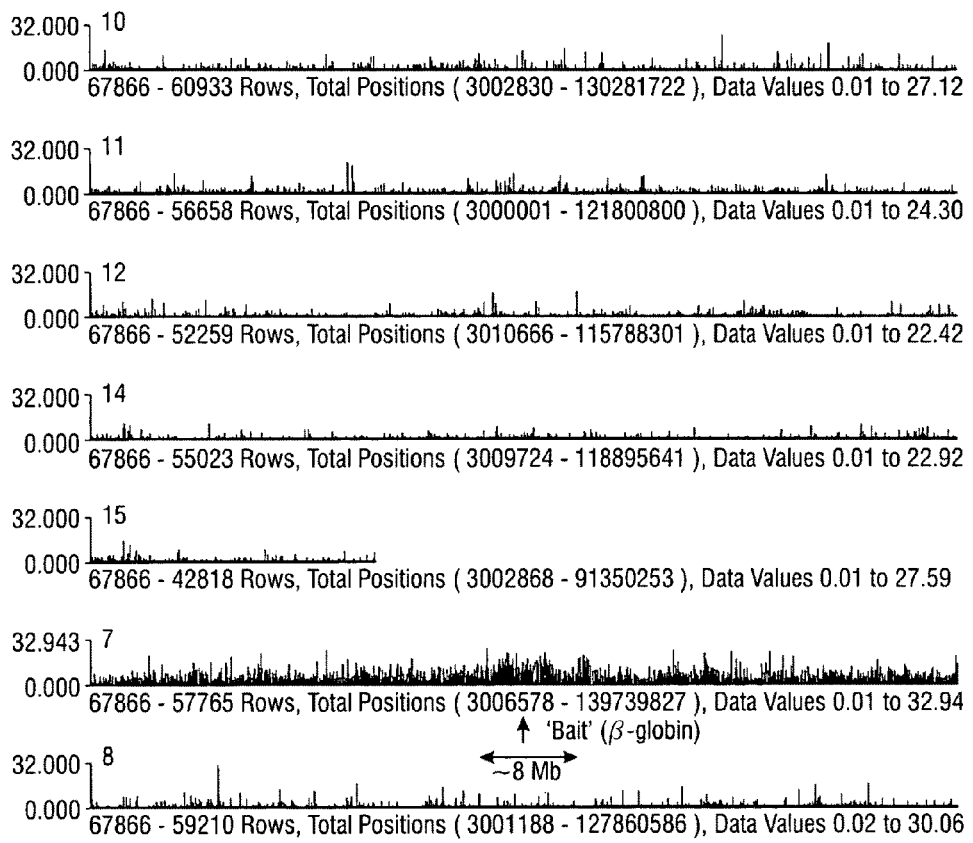
Figure 5:
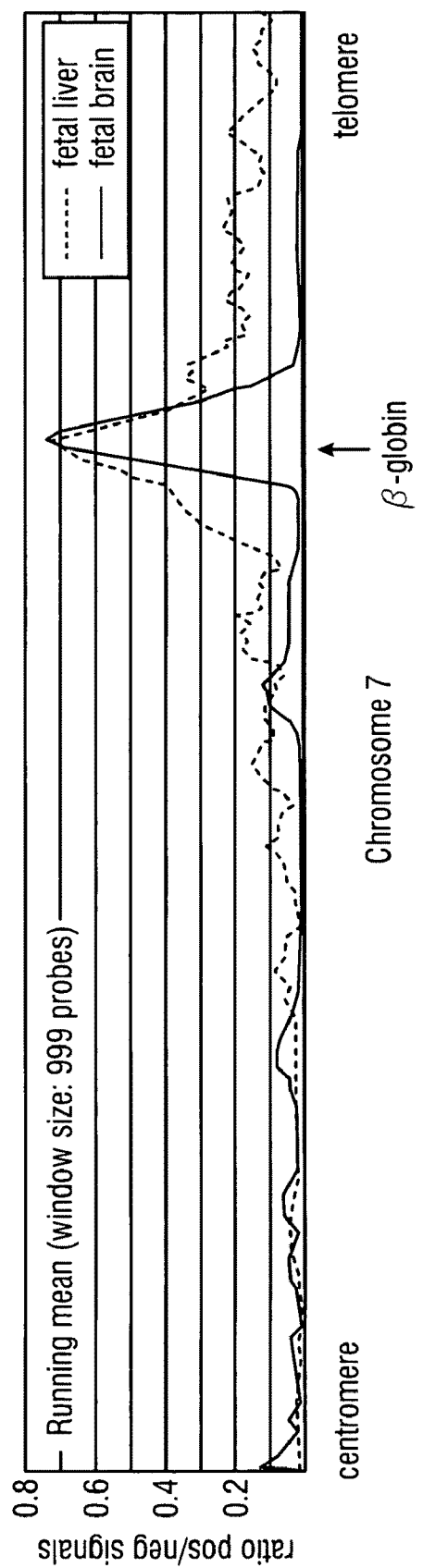
Figure 6:
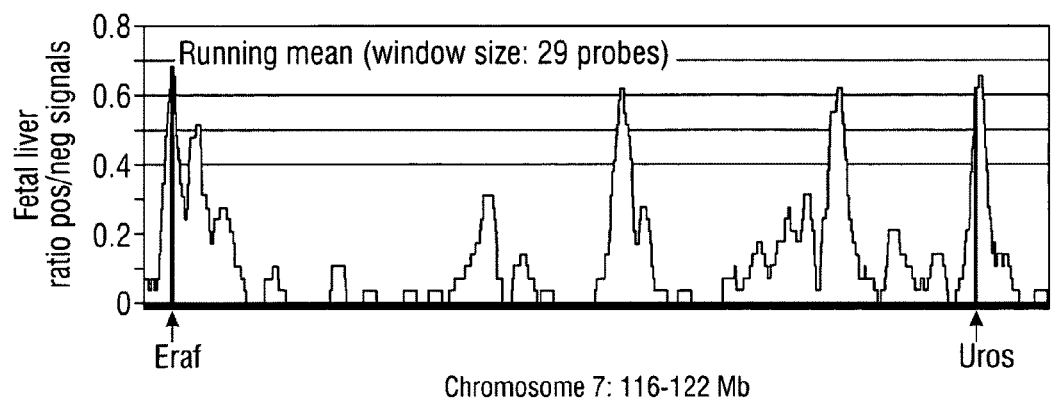
Figure 7:
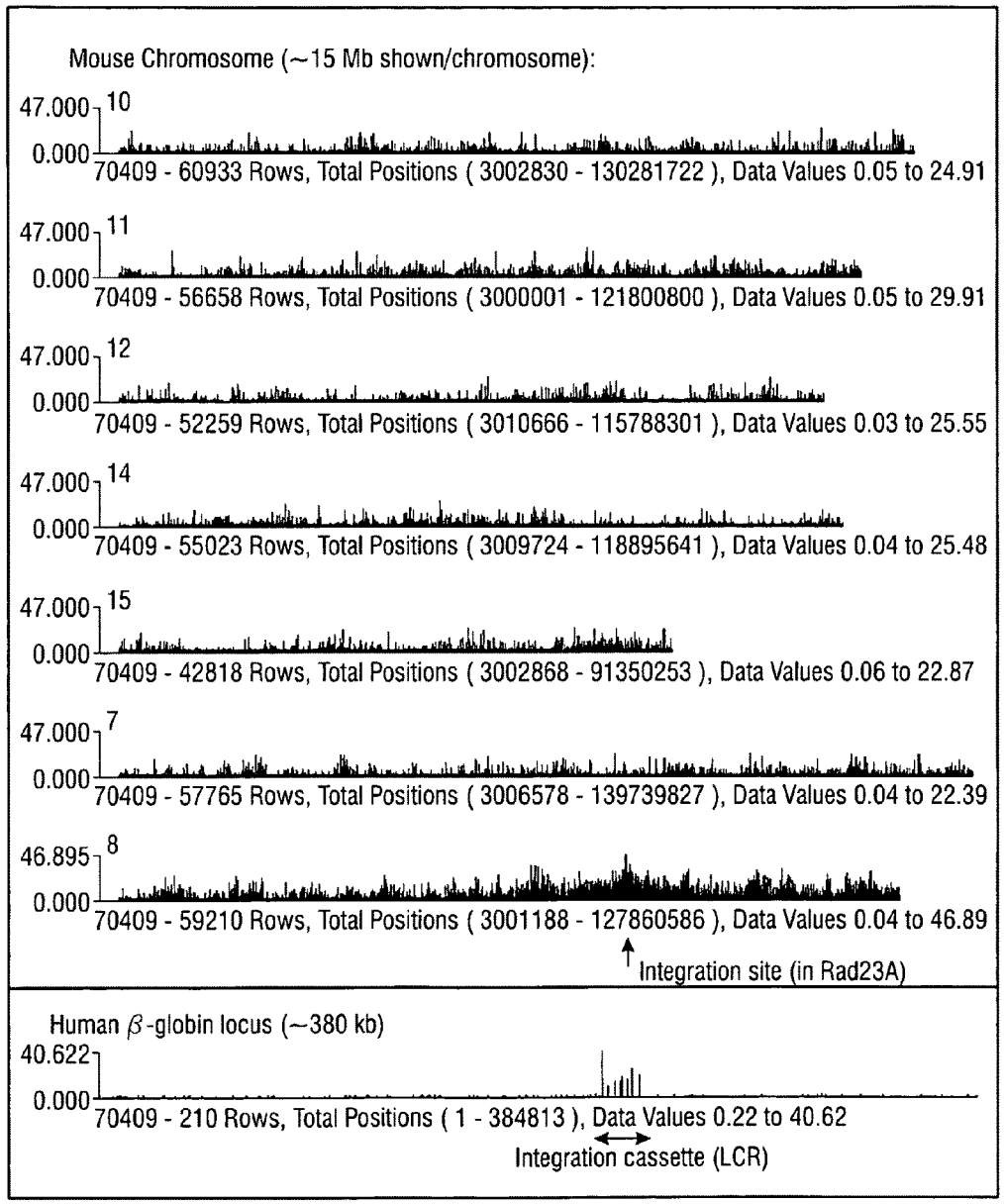
Figure 8:
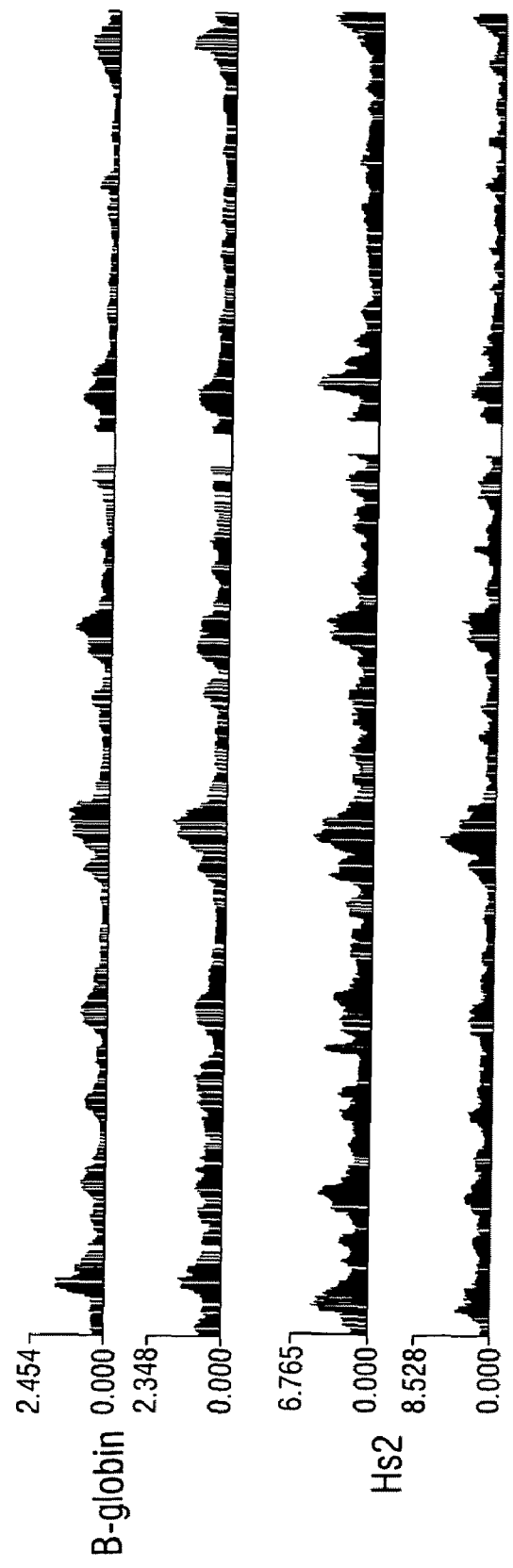

4C technology accurately detects at least 5 Mb of genomic DNA linked in cis to the nucleotide sequence that is analysed (see FIGS. 2-3 and 5). Advantageously, 4C technology may be used to detect any genomic aberration that is accompanied by a change in genomic site separation between rearranged sequences and a 4C sequence (bait) of choice. Such change may be, for example, an increase or decrease in genomic site separation or may be an under-representation (as in deletions) or over-representation (as in duplications) of sequences proximal (e.g. up to or greater than 15 Mb) to the 4C sequence (bait). Typically, such genomic aberrations or rearrangements are a cause of or are associated with diseases—such as cancer (e.g. leukaemia) and other genetic or congenital diseases as described herein.

Genetic aberrations (e.g. genomic or chromosomal aberrations—such as balanced and/or or unbalanced genomic or chromosomal aberrations) include, but are not limited to rearrangements, translocations, inversions, insertions, deletions and other mutations of nucleic acid (e.g. chromosomes) and also losses or gains of part or whole chromosomes. They are a leading cause of genetic disorders or diseases, including congenital disorders and acquired diseases—such as malignancies. In many rearrangements, two different chromosomes are involved. In this way, genes (or fragments of genes) are removed from the normal physiological context of a particular chromosome and are located to a recipient chromosome, adjacent to non-related genes or fragments of genes (often oncogenes or proto-oncogenes).

Malignancies can include acute leukemias, malignant lymphomas and solid tumours. Non-limiting examples of alterations are t(14; 18) which occurs frequently in NHL; t(12; 21) which is frequently found in childhood precursor-B-ALL; and the presence of llq23 (MLL (myeloid-lymphoid leukaemia or mixed-lineage leukaemia) gene) aberrations in acute leukemias.

The MLL gene in chromosome region llq23 is involved in several translocations in both ALL and acute myeloid leukemias (AML). To date, at least ten partner genes have been identified. Some of these translocations,—such as t(4; 11) (q21; q23), t(11; 19) (q23; p13) and t(1; 11) (p32; q23), predominantly occur in ALL, where as others, like t(1; 11) (q21; q23), t(2; 11) (p21; q23), t(6; 11) (q27; q23) and t(9; 11) (p22; q23) are more often observed in AML. Rearrangements involving the llq23 region occur very frequently in infant acute leukemias (around 60-70%), and to a much lesser extent in childhood and adult leukemias (each around 5%).

Rearrangements in lymphoid malignancies often involve Ig or TCR genes. Examples include the three types of translocations (t(8; 14), t(2; 8), and t(8; 22)) that are found in Burkitt's lymphomas, in which the MYC gene is coupled to Ig heavy chain (IGH), Ig kappa (IGK), or Ig lambda (IGL) gene segments, respectively. Another common type of translocation in this category is t(14; 18) (q32; q21) which is observed in about 90% of follicular lymphomas, one of the major NHL types. In this translocation the BCL2 gene is rearranged to regions within the IGH locus within or adjacent to the JH gene segments. The result of this chromosome aberration is the overexpression of the BCL2 protein, which plays a role as a survival factor in growth control by inhibiting programmed cell death.

The BCL2 gene consists of three exons, but these are scattered over a large area. Of these the last exon encodes a large 3' untranslated region (3' UTR). This 3' UTR is one of the two regions in which many t(14; 18) breakpoints are clustered and is called the "major breakpoint region"; the other breakpoint region involved in t(14; 18) translocations, is located 20-30 kb downstream of the BCL2 locus and is called the "minor cluster region". A third BCL2 breakpoint area, the VCR (variant cluster region), is located at the 5' side of the BCL2 locus and is amongst others involved in variant translocations, t(2; 18) and t(18; 22), in which IGK and IGL gene segments are the partner genes.

Thus, by way of example, 4C technology can be applied to the screening of patient material for genetic aberrations near or in loci that were chosen based on their frequent association with a given clinical phenotype. Further non-limiting examples of such loci are AML1, MLL, MYC, BCL, BCR, ABL1, immunoglobulin loci, LYL1, TAL1, TAL2, LMO2, TCRα/δ, TCRβ, HOX and other loci in various lymphoblastic leukemias.

Advantageously, if a genetic aberration is suspected, 4C technology can be applied as the first and only screen to verify and map the presence of the aberration as explained herein.

Detection of Genomic Rearrangements

In a particularly preferred embodiment of the present invention, the methods described herein can be used for the detection of genomic rearrangements.

Currently, genomic rearrangements—such as translocation breakpoints—are very difficult to detect. For example, comparative genomic hybridization (CGH) micro-arrays can detect several types of rearrangements but fail to detect translocations. If translocation is suspected in a patient but chromosome partners are unknown, spectral karyotyping (SKY) may be performed to find translocation partners and obtain an approximate estimate of breakpoint locations. However, the resolution is very poor (usually not better than ~50 Mb) and additional fine-mapping (which is both time consuming and expensive) is usually required. This is normally done using Fluorescence In Situ Hybridization (FISH), which again provides limited resolution. Using FISH, breakpoints can be located to +/−50 kb region at maximum resolution.

DNA-DNA interaction frequencies primarily are a function of the genomic site separation, i.e. DNA-DNA interaction frequencies are inversely proportional to the linear distance cm kilobases) between two DNA loci present on the same physical DNA template (Dekker et al., 2002). Thus, a translocation, which creates one or more new physical DNA templates, is accompanied by altered DNA-DNA interactions near the breakpoints, and this can be measured by 4C technology. Diseases based on translocations are typically caused by aberrant DNA-DNA interactions, as translocation is the result of the physical linkage (interaction) of broken chromosome (DNA) arms.

Accordingly, for the detection of translocations, 4C technology may be used to identify those DNA-DNA interactions that are different between diseased and non-diseased subjects.

By way of example, 4C technology can be applied to the screening of patient material for translocations near loci that were chosen based on their frequent association with a given clinical phenotype as described herein.

If translocation is suspected in a patient but chromosome partners are unknown, an initial mapping may be performed using currently available methods like spectral karyotyping (SKY). This may identify the translocation partners and provide a very rough estimate of breakpoint locations (usually not better than ~50 Mb resolution). 4C technology can then be applied, using 'bait'-sequences in this region located for example at every 2 Mb, 5 Mb, 10 Mb, 20 Mb (or other intervals as described herein) to fine map the breakpoint and identify for example the gene(s) that are mis-expressed as a consequence of the translocation.

Typically a translocation will be identified by way of an abrupt transition from low to high interaction frequencies on a chromosome other than the one containing the 4C-bait sequence, or elsewhere on that same chromosome.

In a preferred embodiment, the sample from the subject is in a pre-malignant state.

In a preferred embodiment, the sample from the subject consists of cultured or uncultured amniocytes obtained by amniocentesis for prenatal diagnosis.

In a preferred array design, probes present on a single array represent the complete genome of a given species at maximum resolution. Thus, arrays to detect translocations and the like by 4C technology contain probes as described herein complementary, to every side of every primary restriction enzyme recognition site in the genome of a given species (e.g. human).

In another preferred design, probes present on a single array represent the complete genome of a given species, but not at maximum resolution. Thus, arrays to detect translocations and the like by 4C technology contain probes as described herein that are complementary to only one side of every primary restriction enzyme recognition site in the genome of a given species (e.g. human).

In another preferred design, probes present on a single array represent the complete genome of a given species; but not at maximum resolution. Thus, arrays to detect translocations, deletions, inversions, duplications and other genomic rearrangements by 4C technology contain probes as described herein that are complementary to one side of every other primary restriction enzyme recognition site as ordered along the linear template of the genome of a given species (e.g. human).

Thus, arrays to detect translocations, deletions, inversions, duplications and other genomic rearrangements by 4C technology contain probes as described herein that each represent a single restriction fragment as obtained after digestion with a primary restriction enzyme. Preferably, this is obtained by ignoring every second, third, fourth, fifth, sixth, seventh, eight, ninth, tenth, twentieth, thirtieth, fortieth, fiftieth, sixtieth, seventieth, eightieth, ninetieth, or one hundredth etc probe that hybridizes to the same restriction fragment. Arrays to detect translocations, deletions, inversions, duplications and other genomic rearrangements by 4C technology may contain probes as described herein that are distributed equally along the linear chromosome templates. Preferably, this is obtained by ignoring one or more probes in those genomic regions that show highest probe density.

In another preferred design, probes present on a single array represent the complete genome of a given species, but not at maximum resolution. Thus, arrays to detect translocations, deletions, inversions, duplications and other genomic rearrangements by 4C technology contain probes as described herein complementary to one side of every third, fourth, fifth, sixth, seventh, eight, ninth, tenth, twentieth, thirtieth, fortieth, fiftieth, sixtieth, seventieth, eightieth, ninetieth, or one hundredth etc primary restriction enzyme recognition site as ordered along the linear template of the genome of a given species (e.g. human). Arrays to detect translocations, deletions, inversions, duplications and other genomic rearrangements by 4C technology may contain probes as described herein, which represent the complete genome, but with a single probe every 100 kilobases. Arrays to detect translocations, deletions, inversions, duplications and other genomic rearrangements by 4C technology may contain probes as described herein which represent every single primary restriction enzyme recognition site in the genome that can be represented by a unique probe sequence.

In another preferred array design, probes as described herein on a single array represent genomic regions of a given size—such as about 50 kb, 100 kb, 200 kb, 300 kb, 400 kb, 500 kb, 1 Mb, 2 Mb, 3 Mb, 4 Mb, 5 Mb, 6 Mb, 7 Mb, 8 Mb, 9 Mb or 10 Mb (e.g. from about 50 kb-10 Mb) around all loci known to be involved in translocations, deletions, inversions, duplications and other genomic rearrangements.

In another preferred array design, probes as described herein on a single array represent genomic regions of a given size—such as about 50 kb, 100 kb, 200 kb, 300 kb, 400 kb, 500 kb, 1 Mb, 2 Mb, 3 Mb, 4 Mb, 5 Mb, 6 Mb, 7 Mb, 8 Mb, 9 Mb or 10 Mb—(e.g. from about 50 kb-10 Mb) around a selection of loci known to be involved in translocations, deletions, inversions, duplications and other genomic rearrangements. Selections can be made on educated criteria, for example they can represent only the loci that are implicated in a given type of disease.

In another preferred array design, probes as described herein on a single array represent a genomic region of interest of, for example, 100 kb, 200 kb, 300 kb, 400 kb, 500 kb, 600 kb, 700 kb, 800 kb, 900 kb, 1 Mb, 2 Mb, 3 Mb, 4 Mb, 5 Mb, 6 Mb, 7 Mb, 8 Mb, 9 Mb, 10 Mb, 20 Mb, 30 Mb, 40 Mb, 50 Mb, 60 Mb, 70 Mb, 80 Mb, 90 Mb, or 100 Mb (e.g. 100 kb-10 Mb) (part of) a chromosome or multiple chromosomes, with each probe being represented multiple (e.g. 10, 100, 1000) times to allow quantitative measurements of hybridisation signal intensities at each probe sequence.

In a preferred experimental design, the 4C sequence (bait) is within about 0 kb, 10 kb, 20 kb, 30 kb, 40 kb, 50 kb, 100 kb, 200 kb, 300 kb, 400 kb, 500 kb, 1 Mb, 2 Mb, 3 Mb, 4 Mb, 5 Mb, 6 Mb, 7 Mb, 8 Mb, 9 Mb 10 Mb, 11 Mb, 12 Mb, 13 Mb, 14 Mb or 15 Mb (e.g. from about 0-15 Mb) or more from the actual rearranged sequence (i.e. breakpoint in case of a translocation).

In a preferred hybridization, two differentially labeled 4C templates obtained with one sequence (4C bait) from a diseased and non-diseased subject are hybridized simultaneously to the same array. Differences in DNA-DNA interactions allow the detection of the breakpoint in cis (on the same chromosome as the 4C-bait) and in trans (on the translocation partner).

In a preferred hybridization, multiple differentially labeled 4C templates obtained with one sequence (4C bait) from diseased and non-diseased subjects are hybridized simultaneously to the same array. Differences in DNA-DNA interactions allow the detection of the breakpoint in cis (on the same chromosome as the 4C-bait) and in trans (on the translocation partner).

Advantageously, multi-color, instead of dual color analysis on micro-arrays may be utilised allowing the simultaneous hybridization of more than two samples to a single array. Accordingly, multi-color hybridization can be used in 4C technology.

In a preferred hybridisation, multiple differentially labeled 4C templates obtained with one sequence (4C bait) from diseased subjects and one differentially labeled 4C template from a non-diseased subject are hybridised simultaneously to the same array. Differences in DNA-DNA interactions allow the detection of the breakpoint in cis (on the same chromosome as the 4C-bait) and in trans (on the translocation partner).

In another preferred hybridisation, two differentially labeled 4C templates from the same non-diseased subject, obtained with two different sequences (4C-baits) that each represent another possible translocation partner, are hybridised simultaneously to the same array. Clusters of strong hybridisation signals observed on the linear template of chromosomes unrelated to the chromosome carrying the sequence of interest (4C-bait) will identify the translocation partner chromosome and the breakpoint on the translocation partner.

In another preferred hybridisation, multiple differentially labeled 4C templates from the same non-diseased subject, obtained with multiple different sequences (4C-baits) that each represent another possible translocation partner, are hybridised simultaneously to the same array. Clusters of strong hybridisation signals observed on the linear template of chromosomes unrelated to the chromosome carrying the sequence of interest (4C-bait) will identify the translocation partner chromosome and its breakpoint for the sequence of interest.

Material used for the detection of translocations, deletions, inversions, duplications and other genomic rearrangements by 4C technology can be obtained by cross-linking (and further processing, as described) of living cells and/or dead cells and/or nuclear lysates and/or isolated chromatin etc. (as described herein) from diseased and/or non-diseased subjects.

Detection of Inversions

Inversions (e.g. balanced inversions) cannot be detected by methods—such as Comparative Genomic Hybridization techniques—but can be detected by 4C technology particularly when the (balanced) inversion is close (e.g. up to about 1-15 Mb or more) to the 4C sequence (bait).

Detection of (balanced) inversions is based on identifying those DNA-DNA interactions that were different between diseased and non-diseased subjects. Inversions will change the relative position (in kilobases) on the physical DNA template of all (but the most centrally located) sequences of the rearranged region as measured against a sequence nearby on the same chromosome that is taken as 4C sequence (bait). Since DNA-DNA interaction frequencies are inversely related to genomic site separation, diseased subjects will give inversed patterns of hybridization intensities for all probes located in the rearranged genomic region, as compared to a non-diseased subject. Thus, 4C technology allows the identification of position and size of (balanced) inversions.

According to this aspect of the present invention, a preferred dedicated array design comprises probes on a single array representing genomic regions of a given size—such as about 50 kb, 100 kb, 200 kb, 300 kb, 400 kb, 500 kb, 1 Mb, 2 Mb, 3 Mb, 4 Mb, 5 Mb, 6 Mb, 6 Mb, 7 Mb, 8 Mb, 9 Mb or 10 Mb) (e.g. 50 kb-10 Mb) around the locus at which the inversion or other rearrangement is suspected.

In another preferred dedicated array design, probes on a single array represent genomic regions of a given size (50 kb, 100 kb, 200 kb, 300 kb, 400 kb, 500 kb, 1 Mb, 2 Mb etc) around the locus at which the inversion or other rearrangement is suspected. For reliable quantitative analysis of signal intensities the amount of probe present on the array is typically in large excess to the amount of cognate fragments that are hybridized to the array. Therefore, it may be necessary to have each probe present multiple times (eg 10, 20, 50, 100, 1000 times etc) on the array. In addition, it may be necessary to titrate the amount of template that is to be hybridized to the array.

Detection of Deletions

Detection of deletions is based on identifying those DNA-DNA interactions that were different between diseased and non-diseased subjects. Deletions will result in the absence of DNA interactions with a 4C sequence (bait) located near (e.g. about 1, 2, 3, 4, 5, 6, 7, 8, 9, 10, 11, 12, 13, 14 or 15 Mb or more) the deleted region. This may result in the complete absence of hybridization signals for all probes located in the rearranged region if the deletion is present on both alleles (homozygous), or a reduction for diseased versus non-diseased subjects of signal intensities if the deletion is present on only one allele (heterozygous). Deletion brings more distal sequences into closer proximity on the physical DNA template to the 4C sequence analyzed (bait), which will result in stronger hybridization signals for probes located directly beyond the deleted region.

Detection of Duplication(s)

Detection of duplication is typically based on identifying those DNA-DNA interactions that are different between diseased and non-diseased subjects. Probes in the duplicated region will show increased hybridization signals with a 4C sequence (bait) located near (e.g. about 1, 2, 3, 4, 5, 6, 7, 8, 9, 10, 11, 12, 13, 14 or 15 Mb or more) the rearranged region, as compared to signals from a control non-diseased subject. Probes beyond the duplicated region are further apart from the 4C sequence and consequently will show decreased hybridization signals as compared to signals from a control non-diseased subject.

Preferably, an increase or a decrease DNA-DNA interaction frequency for the subject sample as compared to the control is indicative of a duplication or insertion.

Preferably, an increase in DNA-DNA interaction frequency for the subject sample as compared to the control and/or a reduction in DNA-DNA interaction frequency for more distant regions is indicative of a duplication or insertion.

Prenatal Diagnosis

Advantageously, 4C technology can also be used in prenatal diagnosis.

Nucleic acid can be obtained from a fetus using various methods that are known in the art. By way of example, amniocentesis can be used to obtain amniotic fluid from which fetal cells in suspension are extracted and cultured for several days (Mercier & Bresson (1995) *Ann. Gnt.*, 38, 151-157). Nucleic acid from the cells can be then extracted. The collection of chorial villi may make it possible to dispense with the culturing step and avoids the collection of amniotic fluid. These techniques may be applied earlier (up to 7 weeks of gestation for the collection of chorial villi and 13-14 weeks for amniocentesis), but with a slightly increased risk of abortion.

A direct collection of fetal blood at the level of the umbilical cord can also be used to obtain nucleic acid, but typically requires a team of clinicians specialised in this technique (Dormer et al. (1996) *Fetal Diagn. Ther.*, 10, 192-199).

Advantageously, genetic aberrations (e.g. genomic or chromosomal aberrations)—such as rearrangements, translocations, inversions, insertions, deletions and other mutations in chromosomes and nucleic acid—may be detected at this stage.

Preferably, genetic aberrations (e.g. genomic or chromosomal aberrations)—such as rearrangements, translocations, inversions, insertions, deletions and other mutations in chromosomes 21, 18, 13, X or Y and also losses or gains of part or whole chromosomes 21, 18, 13, X or Y may be detected since these are the chromosomes in which the majority of aberrations occur in the fetus.

Figure 4:
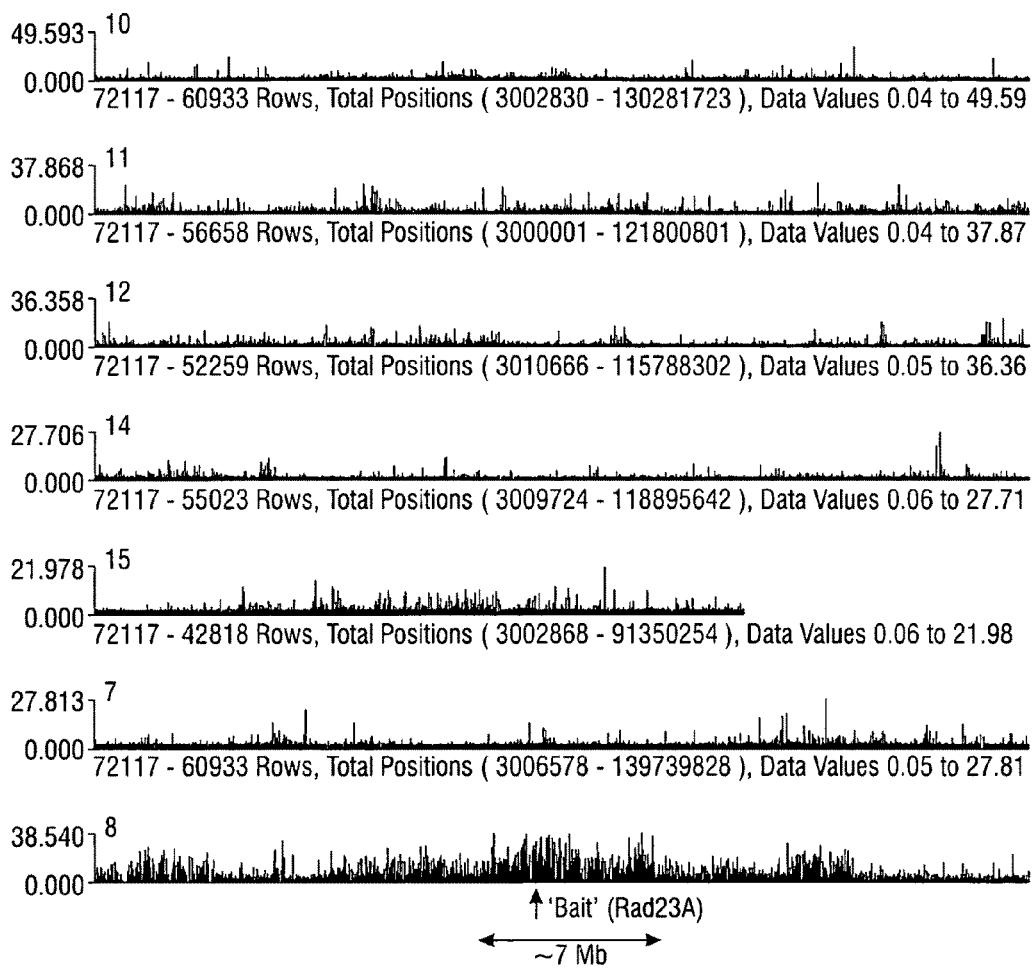

Determination of Genomic Integration Sites 4C technology also allows the determination of genomic integration sites of viruses and transgenes, etc, also when multiple copies are inserted at different positions in the genome (as described in FIG. 4).

Determining Predisposition to Acquiring Certain Translocations

Advantageously, 4C technology can also be applied to non-diseased subjects to measure the genomic environment of loci frequently involved in genetic aberrations. In this way, it is possible to determine the predisposition of the subject to acquire certain genetic aberrations.

Thus, in addition to the medical uses described herein, the present invention can be used in diagnosis.

Subject

The term "subject" includes mammals—such as animals and humans

Agent

The agent may be an organic compound or other chemical. The agent may be a compound, which is obtainable from or produced by any suitable source, whether natural or artificial. The agent may be an amino acid molecule, a polypeptide, or a chemical derivative thereof, or a combination thereof. The agent may even be a polynucleotide molecule—which may be a sense or an anti-sense molecule, or an antibody, for example, a polyclonal antibody, a monoclonal antibody or a monoclonal humanised antibody.

Various strategies have been developed to produce monoclonal antibodies with human character, which bypasses the need for an antibody-producing human cell line. For example, useful mouse monoclonal antibodies have been "humanised" by linking rodent variable regions and human constant regions (Winter, G. and Milstein, C. (1991) *Nature* 349, 293-299). This reduces the human anti-mouse immunogenicity of the antibody but residual immunogenicity is retained by virtue of the foreign V-region framework. Moreover, the antigen-binding specificity is essentially that of the murine donor.

CDR-grafting and framework manipulation (EP 0239400) has improved and refined antibody manipulation to the point where it is possible to produce humanised murine antibodies which are acceptable for therapeutic use in humans. Humanised antibodies may be obtained using other methods well known in the art (for example as described in U.S. Pat. No. 239,400).

The agents may be attached to an entity (e.g. an organic molecule) by a linker which may be a hydrolysable bifunctional linker.

The entity may be designed or obtained from a library of compounds, which may comprise peptides, as well as other compounds, such as small organic molecules.

By way of example, the entity may be a natural substance, a biological macromolecule, or an extract made from biological materials such as bacteria, fungi, or animal (particularly mammalian) cells or tissues, an organic or an inorganic molecule, a synthetic agent, a semi-synthetic agent, a structural or functional mimetic, a peptide, a peptidomimetics, a peptide cleaved from a whole protein, or a peptides synthesised synthetically (such as, by way of example, either using a peptide synthesizer or by recombinant techniques or combinations thereof, a recombinant agent, an antibody, a natural or a non-natural agent, a fusion protein or equivalent thereof and mutants, derivatives or combinations thereof.

Typically, the entity will be an organic compound. For some instances, the organic compounds will comprise two or more hydrocarbyl groups. Here, the term "hydrocarbyl group" means a group comprising at least C and H and may optionally comprise one or more other suitable substituents. Examples of such substituents may include halo-, alkoxy-, nitro-, an alkyl group, a cyclic group etc. In addition to the possibility of the substituents being a cyclic group, a combination of substituents may form a cyclic group. If the hydrocarbyl group comprises more than one C then those carbons need not necessarily be linked to each other. For example, at least two of the carbons may be linked via a suitable element or group. Thus, the hydrocarbyl group may contain hetero atoms. Suitable hetero atoms will be apparent to those skilled in the art and include, for instance, sulphur, nitrogen and oxygen. For some applications, preferably the entity comprises at least one cyclic group. The cyclic group may be a polycyclic group, such as a non-fused polycyclic group. For some applications, the entity comprises at least the one of said cyclic groups linked to another hydrocarbyl group.

The entity may contain halo groups—such as fluoro, chloro, bromo or iodo groups.

The entity may contain one or more of alkyl, alkoxy, alkenyl, alkylene and alkenylene groups—which may be unbranched- or branched-chain Prodrug It will be appreciated by those skilled in the art that the entity may be derived from a prodrug. Examples of prodrugs include certain protected group(s) which may not possess pharmacological activity as such, but may, in certain instances, be administered (such as orally or parenterally) and thereafter metabolised in the body to form an entity that is pharmacologically active.

Suitable pro-drugs may include, but are not limited to, Doxorubicin, Mitomycin, Phenol Mustard, Methotraxate, Antifolates, Chloramphenicol, Camptothecin, 5-Fluorouracil, Cyanide, Quinine, Dipyridamole and Paclitaxel.

It will be further appreciated that certain moieties known as "pro-moieties", for example as described in "Design of Prodrugs" by H. Bundgaard, Elsevier, 1985, may be placed on appropriate functionalities of the agents. Such prodrugs are also included within the scope of the invention.

The agent may be in the form of a pharmaceutically acceptable salt—such as an acid addition salt or a base salt—or a solvate thereof, including a hydrate thereof. For a review on suitable salts see Berge et al, J. Pharm. Sci., 1977, 66, 1-19.

The agent may be capable of displaying other therapeutic properties.

The agent may be used in combination with one or more other pharmaceutically active agents.

If combinations of active agents are administered, then the combinations of active agents may be administered simultaneously, separately or sequentially.

Stereo and Geometric Isomers

The entity may exist as stereoisomers and/or geometric isomers—e.g. the entity may possess one or more asymmetric and/or geometric centres and so may exist in two or more stereoisomeric and/or geometric forms. The present invention contemplates the use of all the individual stereoisomers and geometric isomers of those entities, and mixtures thereof.

Pharmaceutical Salt

The agent may be administered in the form of a pharmaceutically acceptable salt.

Pharmaceutically-acceptable salts are well known to those skilled in the art, and for example, include those mentioned by Berge et al, in J. Pharm. Sci., 66, 1-19 (1977): Suitable acid addition salts are formed from acids which form non-toxic salts and include the hydrochloride, hydrobromide, hydroiodide, nitrate, sulphate, bisulphate, phosphate, hydrogenphosphate, acetate, trifluoroacetate, gluconate, lactate, salicylate, citrate, tartrate, ascorbate, succinate, maleate, fumarate, gluconate, formate, benzoate, methanesulphonate, ethanesulphonate, benzenesulphonate and p-toluenesulphonate salts.

When one or more acidic moieties are present, suitable pharmaceutically acceptable base addition salts can be formed from bases which form non-toxic salts and include the aluminium, calcium, lithium, magnesium, potassium, sodium, zinc, and pharmaceutically-active amines such as diethanolamine, salts.

A pharmaceutically acceptable salt of an agent may be readily prepared by mixing together solutions of the agent and the desired acid or base, as appropriate. The salt may precipitate from solution and be collected by filtration or may be recovered by evaporation of the solvent.

The agent may exist in polymorphic form.

The agent may contain one or more asymmetric carbon atoms and therefore exists in two or more stereoisomeric forms. Where an agent contains an alkenyl or alkenylene group, cis (E) and trans (Z) isomerism may also occur. The present invention includes the individual stereoisomers of the agent and, where appropriate, the individual tautomeric forms thereof, together with mixtures thereof.

Separation of diastereoisomers or cis and trans isomers may be achieved by conventional techniques, e.g. by fractional crystallisation, chromatography or H.P.L.C. of a stereoisomeric mixture of the agent or a suitable salt or derivative thereof. An individual enantiomer of the agent may also be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

The agent may also include all suitable isotopic variations of the agent or a pharmaceutically acceptable salt thereof. An isotopic variation of an agent or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as $^2H$, $^3H$, $^{13}C$, $^{14}C$, $^{15}N$, $^{17}O$, $^{18}O$, $^{31}P$, $^{32}P$, $^{35}S$, $^{18}F$ and $^{36}Cl$, respectively. Certain isotopic variations of the agent and pharmaceutically acceptable salts thereof, for example, those in which a radioactive isotope such as $^3H$ or $^{14}C$ is incorporated, are useful in drug and/or substrate tissue distribution studies. Tritiated, i.e., $^3H$, and carbon-14, i.e., $^{14}C$, isotopes are particularly preferred for their ease of preparation and detectability. Further, substitution with isotopes such as deuterium, i.e., $^2H$, may afford certain therapeutic advantages resulting from greater metabolic stability, for example, increased in vivo half-life or reduced dosage requirements and hence may be preferred in some circumstances. Isotopic variations of the agent and pharmaceutically acceptable salts thereof of this invention can generally be prepared by conventional procedures using appropriate isotopic variations of suitable reagents.

Pharmaceutically Active Salt

The agent may be administered as a pharmaceutically acceptable salt. Typically, a pharmaceutically acceptable salt may be readily prepared by using a desired acid or base, as appropriate. The salt may precipitate from solution and be collected by filtration or may be recovered by evaporation of the solvent.

Chemical Synthesis Methods

The agent may be prepared by chemical synthesis techniques.

It will be apparent to those skilled in the art that sensitive functional groups may need to be protected and deprotected during synthesis of a compound of the invention. This may be achieved by conventional techniques, for example, as described in "Protective Groups in Organic Synthesis" by T W Greene and P G M Wuts, John Wiley and Sons Inc. (1991), and by P. J. Kocienski, in "Protecting Groups", Georg Thieme Verlag (1994).

It is possible during some of the reactions that any stereocentres present could, under certain conditions, be racemised, for example, if a base is used in a reaction with a substrate having an having an optical centre comprising a base-sensitive group. This is possible during e.g. a guanylation step. It should be possible to circumvent potential problems such as this by choice of reaction sequence, conditions, reagents, protection/deprotection regimes, etc. as is well-known in the art.

The compounds and salts may be separated and purified by conventional methods.

Separation of diastereomers may be achieved by conventional techniques, e.g. by fractional crystallisation, chromatography or H.P.L.C. of a stereoisomeric mixture of a compound of formula (I) or a suitable salt or derivative thereof. An individual enantiomer of a compound of formula (I) may also be prepared from a corresponding optically pure intermediate or by resolution, such as by H.P.L.C. of the corresponding racemate using a suitable chiral support or by fractional crystallisation of the diastereomeric salts formed by reaction of the corresponding racemate with a suitably optically active acid or base.

The agent may be produced using chemical methods to synthesise the agent in whole or in part. For example, if the agent comprises a peptide, then the peptide can be synthesised by solid phase techniques, cleaved from the resin, and purified by preparative high performance liquid chromatography (e.g., Creighton (1983) Proteins Structures And Molecular Principles, WH Freeman and Co, New York N.Y.).

The composition of the synthetic peptides may be confirmed by amino acid analysis or sequencing (e.g., the Edman degradation procedure; Creighton, supra).

Synthesis of peptide inhibitor agents (or variants, homologues, derivatives, fragments or mimetics thereof) can be performed using various solid-phase techniques (Roberge JY et al (1995) Science 269: 202-204) and automated synthesis may be achieved, for example, using the ABI 43 1 A Peptide Synthesizer (Perkin Elmer) in accordance with the instructions provided by the manufacturer. Additionally, the amino acid sequences comprising the agent, may be altered during direct synthesis and/or combined using chemical methods with a sequence from other subunits, or any part thereof, to produce a variant agent.

Chemical Derivative

The term "derivative" or "derivatised." as used herein includes chemical modification of an agent. Illustrative of such chemical modifications would be replacement of hydrogen by a halo group, an alkyl group, an acyl group or an amino group.

Chemical Modification

The agent may be a modified agent—such as, but not limited to, a chemically modified agent.

The chemical modification of an agent may either enhance or reduce hydrogen bonding interaction, charge interaction, hydrophobic interaction, Van Der Waals interaction or dipole interaction.

In one aspect, the agent may act as a model (for example, a template) for the development of other compounds.

Pharmaceutical Compositions

In a further aspect, there is provided a pharmaceutical composition comprising an agent identified by the assay method described herein admixed with a pharmaceutically acceptable carrier, diluent, excipient or adjuvant and/or combinations thereof.

In a further aspect, there is provided a vaccine composition comprising an agent.

In a further aspect, there is provided a process of preparing a pharmaceutical composition comprising admixing an agent identified by the assay with a pharmaceutically acceptable diluent, carrier, excipient or adjuvant and/or combinations thereof.

In a further aspect, there is provided a method of preventing and/or treating a disease comprising administering an agent or a pharmaceutical composition or a vaccine to a subject.

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Preservatives, stabilisers, dyes and even flavouring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be administered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be administered by a number of routes.

If the agent is to be administered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions may be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or the pharmaceutical compositions can be injected parenterally, for example, intravenously, intramuscularly or subcutaneously. For parenteral administration, the compositions may be best used in the form of a sterile aqueous solution which may contain other substances, for example, enough salts or monosaccharides to make the solution isotonic with blood. For buccal or sublingual administration the compositions may be administered in the form of tablets or lozenges which can be formulated in a conventional manner.

The agents may be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property or a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

If the agent is a protein, then said protein may be prepared in situ in the subject being treated. In this respect, nucleotide sequences encoding said protein may be delivered by use of non-viral techniques (e.g. by use of liposomes) and/or viral techniques (e.g. by use of retroviral vectors) such that the said protein is expressed from said nucleotide sequence.

The pharmaceutical compositions of the present invention may also be used in combination with conventional treatments.

Administration

The term "administered" includes delivery by viral or non-viral techniques. Viral delivery mechanisms include but are not limited to adenoviral vectors, adeno-associated viral (AAV) vectos, herpes viral vectors, retroviral vectors, lentiviral vectors, and baculoviral vectors. Non-viral delivery mechanisms include lipid mediated transfection, liposomes, immunoliposomes, lipofectin, cationic facial amphiphiles (CFAs) and combinations thereof.

The components may be administered alone but will generally be administered as a pharmaceutical composition—e.g. when the components are is in admixture with a suitable pharmaceutical excipient, diluent or carrier selected with regard to the intended route of administration and standard pharmaceutical practice.

For example, the components can be administered in the form of tablets, capsules, ovules, elixirs, solutions or suspensions, which may contain flavouring or colouring agents, for immediate-, delayed-, modified-, sustained-, pulsed- or controlled-release applications.

If the pharmaceutical is a tablet, then the tablet may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The routes for administration (delivery) may include, but are not limited to, one or more of oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, vaginal, epidural, sublingual.

Dose Levels

Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

Formulation

The component(s) may be formulated into a pharmaceutical composition, such as by mixing with one or more of a suitable carrier, diluent or excipient, by using techniques that are known in the art.

Disease

Aspects of the present invention may be used for the treatment and/or prevention and/or diagnosis and/or prognosis of a disease—such as those listed in WO-A-98/09985.

For ease of reference, part of that list is now provided: macrophage inhibitory and/or T cell inhibitory activity and thus, anti-inflammatory activity; anti-immune activity, i.e. inhibitory effects against a cellular and/or humoral immune response, including a response not associated with inflammation; diseases associated with viruses and/or other intracellular pathogens; inhibit the ability of macrophages and T cells to adhere to extracellular matrix components and fibronectin, as well as up-regulated fas receptor expression in T cells; inhibit unwanted immune reaction and inflammation including arthritis, including rheumatoid arthritis, inflammation associated with hypersensitivity, allergic reactions, asthma, systemic lupus erythematosus, collagen diseases and other autoimmune diseases, inflammation associated with atherosclerosis, arteriosclerosis, atherosclerotic heart disease, reperfusion injury, cardiac arrest, myocardial infarction, vascular inflammatory disorders, respiratory distress syndrome or other cardiopulmonary diseases, inflammation associated with peptic ulcer, ulcerative colitis and other diseases of the gastrointestinal tract, hepatic fibrosis, liver cirrhosis or other hepatic diseases, thyroiditis or other glandular diseases, glomerulonephritis or other renal and urologic diseases, otitis or other oto-rhino-laryngological diseases, dermatitis or other dermal diseases, periodontal diseases or other dental diseases, orchitis or epididimo-orchitis, infertility, orchidal trauma or other immune-related testicular diseases, placental dysfunction, placental insufficiency, habitual abortion, eclampsia, pre-eclampsia and other immune and/or inflammatory-related gynecological diseases, posterior uveitis, intermediate uveitis, anterior uveitis, conjunctivitis, chorioretinitis, uveoretinitis, optic neuritis, intraocular inflammation, e.g. retinitis or cystoid macular oedema, sympathetic ophthalmia, scleritis, retinitis pigmentosa, immune and inflammatory components of degenerative fondus disease, inflammatory components of ocular trauma, ocular inflammation caused by infection, proliferative vitreo-retinopathies, acute ischaemic optic neuropathy, excessive scarring, e.g. following glaucoma filtration operation, immune and/or inflammation reaction against ocular implants and other immune and inflammatory-related ophthalmic diseases, inflammation associated with autoimmune diseases or conditions or disorders where, both in the central nervous system (CNS) or in any other organ, immune and/or inflammation suppression would be beneficial, Parkinson's disease, complication and/or side effects from treatment of Parkinson's disease, AIDS-related dementia complex HIV-related encephalopathy, Devic's disease, Sydenham chorea, Alzheimer's disease and other degenerative diseases, conditions or disorders of the CNS, inflammatory components of stokes, post-polio syndrome, immune and inflammatory components of psychiatric disorders, myelitis, encephalitis, subacute sclerosing pan-encephalitis, encephalomyelitis, acute neuropathy, subacute neuropathy, chronic neuropathy, Guillaim-Barre syndrome, Sydenham chora, myasthenia gravis, pseudo-tumour cerebri, Down's Syndrome, Huntington's disease, amyotrophic lateral sclerosis, inflammatory components of CNS compression or CNS trauma or infections of the CNS, inflammatory components of muscular atrophies and dystrophies, and immune and inflammatory related diseases, conditions or disorders of the central and peripheral nervous systems, post-traumatic inflammation, septic shock, infectious diseases, inflammatory complications or side effects of surgery, bone marrow transplantation or other transplantation complications and/or side effects, inflammatory and/or immune complications and side effects of gene therapy, e.g. due to infection with a viral carrier, or inflammation associated with AIDS, to suppress or inhibit a humoral and/or cellular immune response, to treat or ameliorate monocyte or leukocyte proliferative diseases, e.g. leukaemia, by reducing the amount of monocytes or lymphocytes, for the prevention and/or treatment of graft rejection in cases of transplantation of natural or artificial cells, tissue and organs such as cornea, bone marrow, organs, lenses, pacemakers, natural or artificial skin tissue. Specific cancer related disorders include but not limited to: solid tumours; blood born tumours such as leukemias; tumor metastasis; benign tumours, for example hemangiomas, acoustic neuromas, neurofibromas, trachomas, and pyogenic granulomas; rheumatoid arthritis; psoriasis; ocular angiogenic diseases, for example, diabetic retinopathy, retinopathy of prematurity, macular degeneration, corneal graft rejection, neovascular glaucoma, retrolental fibroplasia, rubeosis; Osler-Webber Syndrome; myocardial angiogenesis; plaque neovascularization; telangiectasia; hemophiliac joints; angiofibroma; wound granulation; coronary collaterals; cerebral collaterals; arteriovenous malformations; ischemic limb angiogenesis; neovascular glaucoma; retrolental fibroplasia; diabetic neovascularization; heliobacter related diseases, fractures, vasculogenesis, hematopoiesis, ovulation, menstruation and placentation.

Preferably, the disease is cancer—such as acute lymphocytic leukemia (ALL), acute myeloid leukemia (AML), adrenocortical cancer, anal cancer, bladder cancer, blood cancer, bone cancer, brain tumor, breast cancer, cancer of the female genital system, cancer of the male genital system, central nervous system lymphoma, cervical cancer, childhood rhabdomyosarcoma, childhood sarcoma, chronic lymphocytic leukemia (CLL), chronic myeloid leukemia (CML), colon and rectal cancer, colon cancer, endometrial cancer, endometrial sarcoma, esophageal cancer, eye cancer, gallbladder cancer, gastric cancer, gastrointestinal tract cancer, hairy cell leukemia, head and neck cancer, hepatocellular cancer, Hodgkin's disease, hypopharyngeal cancer, Kaposi's sarcoma, kidney cancer, laryngeal cancer, leukemia, liver cancer, lung cancer, malignant fibrous histiocytoma, malignant thymoma, melanoma, mesothelioma, multiple myeloma, myeloma, nasal cavity and paranasal sinus cancer, nasopharyngeal cancer, nervous system cancer, neuroblastoma, non-Hodgkin's lymphoma, oral cavity cancer, oropharyngeal cancer, osteosarcoma, ovarian cancer, pancreatic cancer, parathyroid cancer, penile cancer, pharyngeal cancer, pituitary tumor, plasma cell neoplasm, primary-CNS lymphoma, prostate cancer, rectal cancer, respiratory system, retinoblastoma, salivary gland cancer, skin cancer, small intestine cancer, soft tissue sarcoma, stomach cancer, stomach cancer, testicular cancer, thyroid cancer, urinary system cancer, uterine sarcoma, vaginal cancer, vascular system, Waldenstrom's macroglobulinemia and Wilms' tumor.

Kits

The materials for use in the methods of the present invention are ideally suited for preparation of kits.

Such a kit may comprise containers, each with one or more of the various reagents (typically in concentrated form) utilised in the methods described herein, including, for example, a primary restriction enzyme, a secondary restriction enzyme, a cross-linking agent, a ligation enzyme (e.g. a ligase) and an agent to reverse the cross-linking (e.g. proteinase K).

Oligonucleotides may also be provided in containers which can be in any form, e.g., lyophilized, or in solution (e.g., a distilled water or buffered solution), etc.

In a preferred aspect of the present invention, there is provided a kit comprising a set of probes as described herein, an array and optionally one or more labels.

A set of instructions will also typically be included.

Uses

Advantageously, the present invention can be used in order to obtain information about the spatial organisation of nucleotide sequences—such as genomic loci in vitro or in vivo.

By way of example, 4C technology can be used to study the three dimensional organisation of one or more gene loci. In particular, this technology can be used to study the role of one or more transcription factors in the three dimensional organisation of one or more gene loci.

By way of further example, 4C technology can be used to study the role of trans-acting factors and cis-regulatory DNA elements.

By way of further example, 4C technology can be used to study long range gene regulation in vitro or in vivo.

By way of further example, 4C technology can be used to study intra-chromosomal proximity and interaction.

By way of further example, 4C technology can be used to study inter-chromosomal proximity and interaction.

By way of further example, 4C technology can be used to identify nucleotide sequences that function with a promoter, enhancer, silencer, insulator, locus control region, origin of replication, MAR, SAR, centromere, telomere or any other sequence of interest in a regulatory network.

By way of further example, 4C technology can be used to identify genes responsible for a phenotype (disease) in cases where a mutation and/or deletion happens to affect a distant regulatory element and their mapping therefore fails to provide such information.

By way of further example, 4C technology can be used to eventually reconstruct the spatial conformation of gene loci, large genomic regions or even complete chromosomes.

By way of further example, 4C technology can be used to define potential anchor sequences that keep certain chromosomes together in the nuclear space.

By way of further example, 4C technology can be used to eventually reconstruct at high resolution the positioning of chromosomes with respect to each other.

By way of further example, 4C technology can be used in diagnosis (e.g. prenatal diagnosis) to detect or identify genomic rearrangements and/or aberrations—such as translocations, deletions, inversions, duplications.

General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. I. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA Methods in Enzymology*, Academic Press. Each of these general texts is herein incorporated by reference.

The invention will now be further described by way of Example, which are meant to serve to assist one of ordinary skill in the art in carrying out the invention and are not intended in any way to limit the scope of the invention.

Example 1

Materials & Methods

4C Technology

The initial steps of the 3C technology procedure were performed as described previously (Splinter et al. (2004). *Methods Enzymol* 375, 493-507 (2004), yielding ligation products between HindIII fragments. This HindIII ligated 3C template (~50 µg) was digested overnight at 100 ng/µl with 50 U of a secondary, frequent cutting, restriction enzyme, being either DpnII (HS2, Rad23A) or NlaIII (β-major). To avoid constraints in DNA circle formation (Rippe et al. (1995) *Trends Biochem Sci* 20, 500-6), care was taken to choose a secondary restriction enzyme that did not cut within about 350-400 bp from the HindIII restriction site that demarcates the restriction fragment of interest (i.e. the 'bait'). After secondary restriction enzyme digestion, DNA was phenol extracted, ethanol precipitated and subsequently ligated at low concentration (50 µg sample in 14 ml using 200 U ligase (Roche), 4 hours at 16° C.) to promote DpnII- or DpnII-circle formation. Ligation products were phenol extracted and ethanol precipitated, using glycogen (Roche) as a carrier (20 µg/ml). The circles of interest were linearised by digesting overnight with a 50 U of a tertiary restriction enzyme that cuts the bait in between the primary and secondary restriction enzyme recognition sites, using the following restriction enzymes: SpeI (HS2), PstI (Rad23A) and PflmI (β-major). This linearisation step was performed to facilitate subsequent primer hybridization during the first rounds of PCR amplification. Digested products were purified using a QIAquick nucleotide removal (250) column (Qiagen).

PCR reactions were performed using the Expand Long Template PCR system (Roche), using conditions carefully optimized to assure linear amplification of fragments sized up to 1.2 kb (80% of 4C-PCR fragments are smaller than 600 bp). PCR conditions were as follows: 94° C. for 2 minutes, 30 cycles of 94° C. for 15 seconds, 55° C. for 1 minute and 68° C. for 3 minutes, followed by a final step of 68° C. for 7 minutes. The maximum amount of template that still shows linear range of amplification was determined. For this, serial dilutions of template were added to PCR reactions, amplified DNA material was run out on an agarose gel and PCR products were quantified using ImageQuant software. Typically, 100-200 ng of template per 50 µl PCR reaction gave products in the linear range of amplification. 16 to 32 PCR reactions were pooled and purified this 4C template using the QIAquick nucleotide removal (250) system (Qiagen). Purified 4C template was labeled and hybridized to arrays according to standard ChIP-chip protocols (Nimblegen Systems of Iceland, LLC). Differentially labeled genomic DNA, which was digested with the primary and secondary enzyme used in the 4C procedure, served as a control template to correct for differences in hybridisation efficiencies. For each experiment two independently processed samples were labeled with alternate dye orientations.

4C-Primer-Sequences Used:

| HS2: | 5'-ACTTCCTACACATTAACGAGCC-3', |
|---|---|
| | 5'-GCTGTTATCCCTTTCTCTTCTAC-3' |
| Rad23A: | 5'-TCACACGCGAAGTAGGCC-3', |
| | 5'-CCTTCCTCCACCATGATGA-3' |
| β-major: | 5'-AACGCATTTGCTCAATCAACTACTG-3', |
| | 5'-GTTGCTCCTCACATTTGCTTCTGAC-3' |

4C Arrays

Arrays and analysis were based on NCBI build m34. Probes (60-mers) were selected from the sequences 100 bp up and downstream of HindIII sites. The CG-content was optimized towards 50%, for uniform hybridization signals. To prevent cross-hybridization, probes that had any similarity with highly abundant repeats (RepBase 10.09)[3] were removed from the probe set. In addition, probes that gave more than two BLAST hits in the genome were also removed from the probe set. Sequence alignments were performed using MegaBLAST (Thang et al. (2000) *J Comput Biol* 7, 203-14) using the standard settings. A hit was defined as an alignment of 30 nt or longer.

4C Data Analysis

The signal ratio 4C-sample/genomic DNA was calculated for each probe and the data was visualized with SignalMap software provided by Nimblegen Systems. Data were analyzed using the R package (http://www.r-project.org), Spotfire and Excel. Unprocessed hybridization ratios showed clusters of 20-50 positive 4C-signals along the chromosome template. To define these clusters, a running mean was applied. Various window sizes were used, ranging from 9-39 probes, which all identified the same clusters. Results shown were based on a window size of 29 probes (on average 60 kb) and were compared to the running mean performed across randomized data. This was done for each array separately. Consequently, all measurements were appreciated relative to the amplitude and noise of that specific array. The False Discovery Rate (FDR), defined as (no. false positives)/(no. of false positives+no. of true positives) was determined as follows: (number of positives in the randomised set)/(number of positives in the data). The threshold level was determined using a top down approach to establish the minimal value for which: FDR<0.05.

Next, biological duplicate experiments were compared. Windows that met the threshold in both duplicates were considered positive. When comparing randomized data, no windows were above threshold in both duplicates. Positive windows directly adjacent on the chromosome template were joined (no gaps allowed), creating positive areas.

Expression Analysis

For each tissue, three independent microarrays were performed according to Affymetrix protocol (mouse 430_2 arrays). Data were normalized using RMA ca-tools; www.bioconductor.org) and for each probe-set the measurements of the three microarrays were averaged. In addition, when multiple probe-sets represented the same gene, they were also averaged. Mas5calls (Ally library: www.bioconductor.org) was used to establish "present", "absent" and "marginal" calls. Genes with a "present" call in all three arrays and an expression value bigger than 50 were called expressed. 'Fetal liver-specific genes' were classified as genes that met our criteria of being expressed in fetal liver and had more than five times higher expression values compared to fetal-brain. To provide a measure of overall transcriptional activity around each gene, a running sum was applied. For this, we used log-transformed expression values. For each gene we calculated the sum of the expression of all genes found in a window 100 kb upstream of the start and 100 kb downstream of the end of the gene, including the gene itself. Resulting values for active genes found inside positive 4C regions (n=124, 123 and 208 respectively for HS2 in liver, Rad23A in brain and Rad23A in liver) were compared to the values obtained for active genes outside positive 4C areas (n=153, 301 and 186, respectively, where n=153 corresponds to the number of active, non-interacting, genes present between the most centromeric interacting region and the telomere of chromosome 7); the two groups were compared using a one tailed Wilcoxon rank sum test.

FISH Probes

The following BAC clones (BACPAC Resources Centre) were used; RP23-370E12 for Hbb-1, RP23-317H16 for chr.7 at 80.1 Mb (OR gene cluster), RP23-334E9 for Uros, RP23-32C19 for chr.7 at 118.3 Mb, RP23-143F10 for chr.7 at 130.1 Mb, RP23-470N5 for chr.7 at 73.1 Mb, RP23-247L11 for chr.7 at 135.0 Mb (OR gene cluster), RP23-136A15 for Rad23A, RP23-307P24 for chr.8 at 21.8 Mb and RP23-460F21 for chr.8 at 122.4 Mb. For a chromosome 7 centromere specific probe we used P1 clone 5279 (Genome Systems Inc.) that anneals to DNA segment D7Mit21. Random prime labeled probes were prepared using BioPrime Array CGH Genomic Labeling System (Invitrogen). Prior to labeling, DNA was digested with DpnII and purified with a DNA clean and concentrator-5 kit (Zymo research). Digested DNA (300 ng) was labeled with SpectrumGreen dUTP (Vysis) or Alexa fluor 594 dUTP (Molecular probes) and purified through a GFX PCR DNA and Gel Band Purification kit (Amersham Biosciences) to remove unincorporated nucleotides. Specificity of labeled probes was tested on metaphase spreads prepared from marine ES cells.

Cryo-FISH

Cryo-FISH was performed as described before[5]. Briefly, E14.5 liver and brain were fixed for 20 min in 4% paraformaldehyde/250 mM HEPES, pH 7.5 and cut into small tissue blocks, followed by another fixation step of 2 hrs in 8% paraformaldehyde at 4° C. Fixed tissue blocks were immersed in 23 M sucrose for 20 min at room temperature, mounted on a specimen holder and snap-frozen in liquid nitrogen. Tissue blocks were stored in liquid nitrogen until sectioning. Ultrathin cryosections of approximately 200 nm were cut using an Reichert Ultramicrotome E equipped with cryo-attachment (Leica). Using a loop filled with sucrose, sections were transferred to coverslips and stored at −20° C. For hybridization, sections were washed with PBS to remove sucrose, treated with 250 ng/ml RNase in 2×SSC for 1 hr at 37° C., incubated for 10 min in 0.1 M HCL, dehydrated in a series of ethanol and denatured for 8 min at 80° C. in 70% formamide/2×SSC, pH 7.5. Sections were again dehydrated directly prior to probe hybridization. 500 ng labeled probe was co-precipitated with 5 μg of mouse Cot1 DNA (Invitrogen) and dissolved in hybmix (50% formamide, 10% dextran sulfate, 2×SSC, 50 mM phosphate buffer, pH 7.5). Probes were denatured for 5 min at 95° C., reannealed for 30 min at 37° C. and hybridized for at least 40 hrs at 37° C. After posthybridization washes, nuclei were counterstained with 20 ng/ml DAPI (Sigma) in PBS/0.05% Tween-20 and mounted in Prolong Gold antifade reagent (Molecular Probes).

Images were collected with a Zeiss Axio Imager Z1 epifluorescence microscope (×100 plan apochromat, 1.4 oil objective), equipped with a CCD camera and Isis FISH Imaging System software (Metasystems). A minimum of 250 β-globin or Rad23A alleles was analyzed and scored as overlapping or non-overlapping with BACs located elsewhere in the genome, by a person not knowing the probe combination applied to the sections. Replicated goodness-of-fit tests (G-statistic)[6] were performed to assess significance of differences between values measured for 4C-positive versus 4C negative regions. Overview of the results is provided in Table 2.

Although we found statistically significant differences between background (0.4-3.9%) and true (5-20.4%) interaction frequencies, it may be clear that frequencies measured by cryo-FISH are lower than those measured by others using different FISH protocols. Sectioning may separate some interacting loci and cryo-FISH measurements will therefore slightly underestimate true interaction frequencies. On the other hand, current 2D- and 3D FISH procedures will overestimate these percentages due to limited resolution in the z-direction. In the future, improved microscopy techniques in combination with more specific FISH probes will better reveal true interaction frequencies.

Example 2

The 3C procedure (i.e. formaldehyde fixation, (primary) restriction enzyme digestion, re-ligation of cross-linked DNA fragments and DNA purification) is carried out essentially as described (Splinter et al., (2004) *Methods Enzymol.* 375: 493-507), yielding a DNA mixture ('3C template') containing restriction fragments that are ligated because they were originally close in the nuclear space.

Inverse PCR is performed to amplify all fragments ligated to a given restriction fragment ('bait'; chosen because it contains a promoter, enhancer, insulator, matrix attachment region, origin of replication or any other first (target) nucleotide sequence).

For this, DNA circles are created by digesting the 3C template with a secondary restriction enzyme (preferably a frequent cutter recognizing tetra- or penta-nucleotide sequences), followed by ligation under dilute conditions such that intra-molecular interactions are favoured. To minimise a bias in circle formation due to topological constraints (Rippe et al, (2001) Trends in Biochem. Sciences 26, 733-40), a secondary restriction enzyme should be chosen that preferably cuts the bait at >350-400 bp from the primary restriction site. To increase inverse PCR amplification efficiency and reproducibility, circles are best linearised before PCR amplification by a restriction enzyme (e.g. a 6 or more by critter) that cuts the bait between the diagnostic primary and secondary restriction site.

Digestion of the 3C template with the secondary restriction enzyme, circularisation through ligation under diluted conditions and linearisation of bait-containing circles are performed under conditions standard for such DNA manipulations to yield a DNA template for inverse PCR amplification ('4C template').

Accordingly, 10 μg of 3C template is digested in 100 μl with 20 U of the secondary restriction enzyme (overnight), followed by heat-inactivation of the enzyme and DNA purification. Ligation is performed in 10 ml (1 ng/μl DNA) with 50 U T4 ligase (4 hrs at 16° C., 30 min at RT), followed by DNA purification. Finally, linearisation of the circles of interest is done in 100 μl with 20 U of restriction enzyme (overnight), followed again by DNA purification.

For inverse PCR, two bait-specific primers are designed, each as close as possible to the primary and directly neighbouring secondary restriction enzyme recognition site, respectively, and each with its 3' end facing outwards so that extension proceeds immediately across the restriction sites into a fragment ligated to the bait. Inverse PCR with these primers is preferably carried out on 100-400 ng DNA of 4C template (per 50 μl PCR reaction mix), to include a maximum number of ligation events per PCR reaction. We perform inverse PCR applying the Expand Long Template PCR System (Roche), using buffer 1 according to manufacturer's procedures.

The following PCR cycles are performed:
1. 2 min 94° C.
2. 15 sec 94° C.
3. 1 min 55° C.
4. 3 min 68° C.
5. repeat step 2-4 29× (or anything between 25-40×)
6. 7 min 68° C.
7. end Gel electrophoresis is performed to analyse reproducibility between individual PCR reactions. Typically, identical product patterns should be obtained.

In order to obtain sufficient material for labelling by random priming and array hybridisation, multiple PCR reactions (each obtained after 30 cycles of PCR) can be pooled, (instead of increasing the number of PCR cycles per reaction). As an alternative for random primed labelling, labelled nucleotides can be incorporated in the last cycles of PCR (e.g. 30 cycles (no label)+10 cycles (label)).

Example 3

Figure 9:
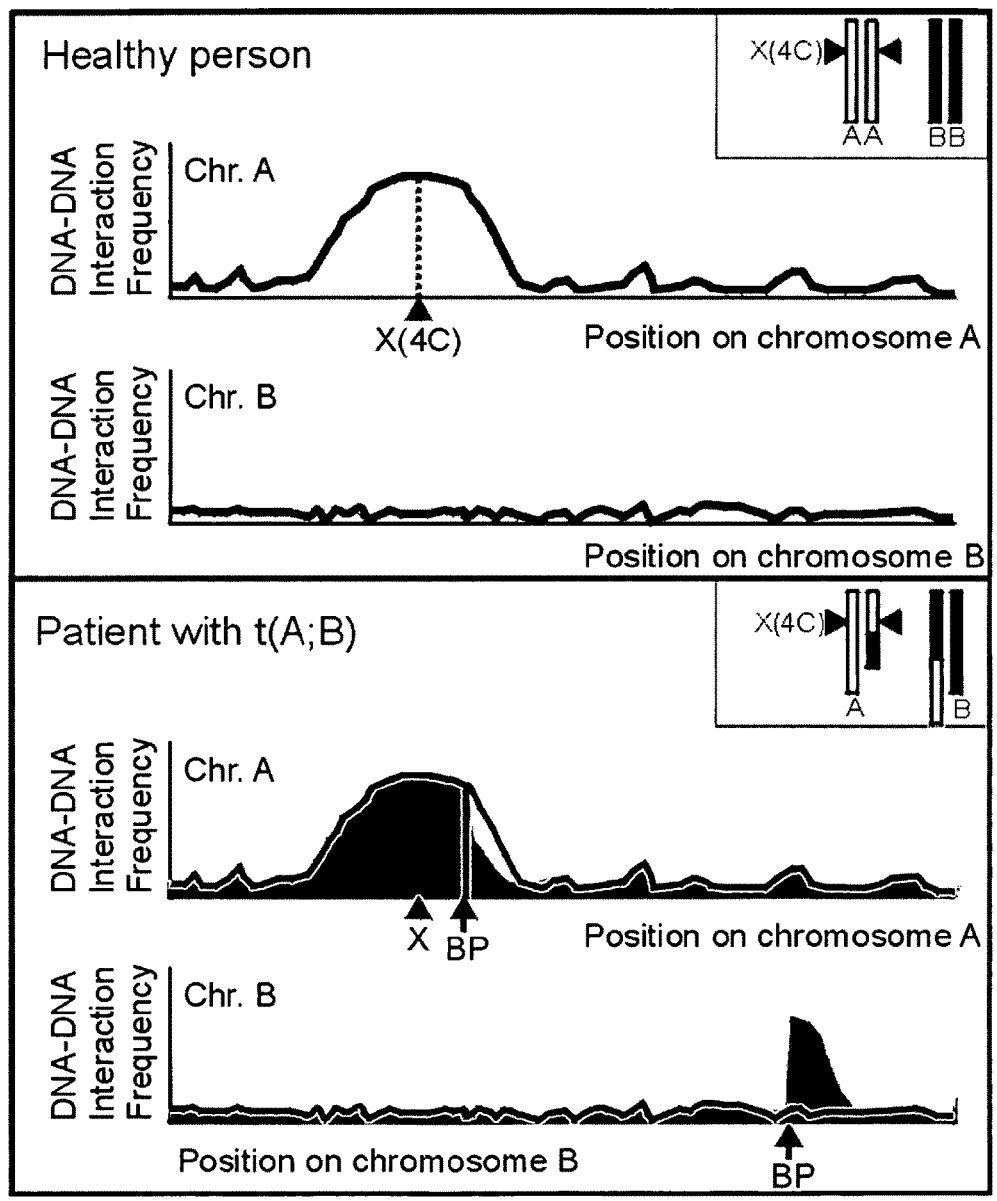
Figure 10:
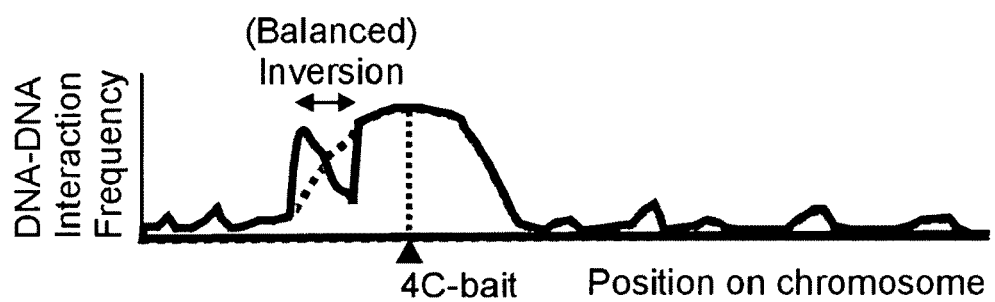
Figure 11:
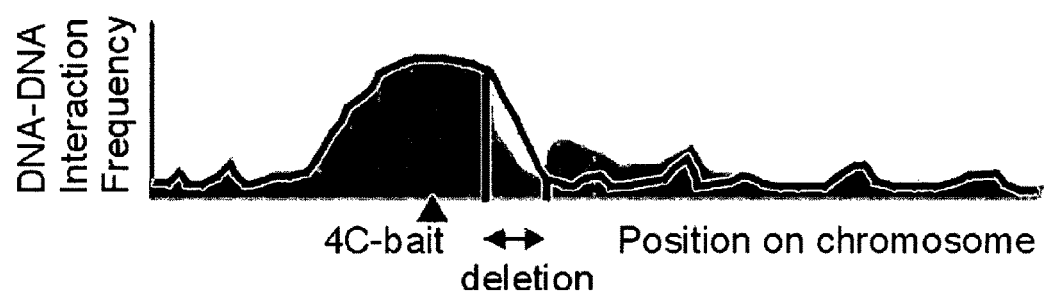
Figure 12:
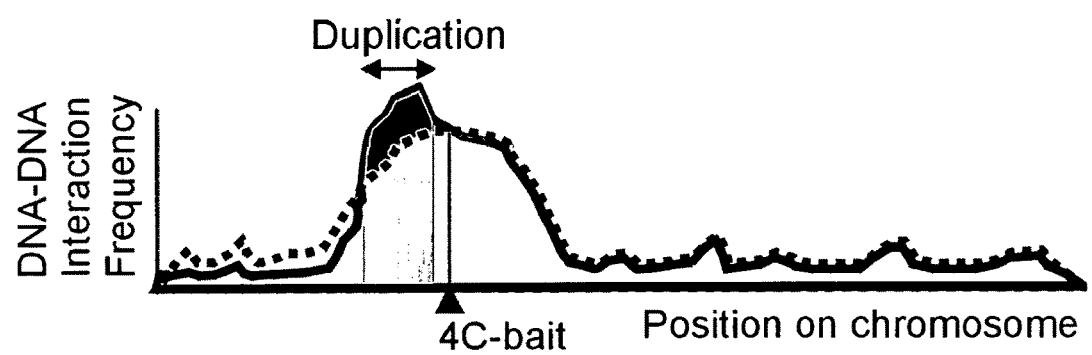

Detection of Translocation Using 4C Technology 4C technology is used to measure the interaction frequencies for a given sequence X present on a given chromosome A in cells from a healthy subject and in cells from a patient carrying a single, reciprocal, translocation between chromosome A and B with the breakpoint being close to sequence X (as shown in FIG. 9).

In normal cells this analysis reveals elevated hybridization signals (i.e. frequent interactions with X) for (almost) every probe located within 0.2-10 Mb of sequence X on chromosome A (the actual size of the chromosomal region showing strong cross-linking signals depends mostly on the complexity of the sample that was hybridized to the array). Elsewhere on the same chromosome A, as well as on other chromosomes, no such large region (on the linear DNA template) of probes with elevated hybridization signals is observed.

In patient cells however, hybridization signals with all chromosome A probes located on the other side of the breakpoint are reduced by ~50% (one copy of chromosome A is still intact and will produce normal signals), while a unique (i.e. not present in normal cells) concentration of elevated hybridization signals is observed for probes bordering the breakpoint on chromosome B. In fact, the abrupt transition between probes showing no versus strong hybridization signals on chromosome B reveals the location of the breakpoint on chromosome B.

Example 4

Figure 13A:
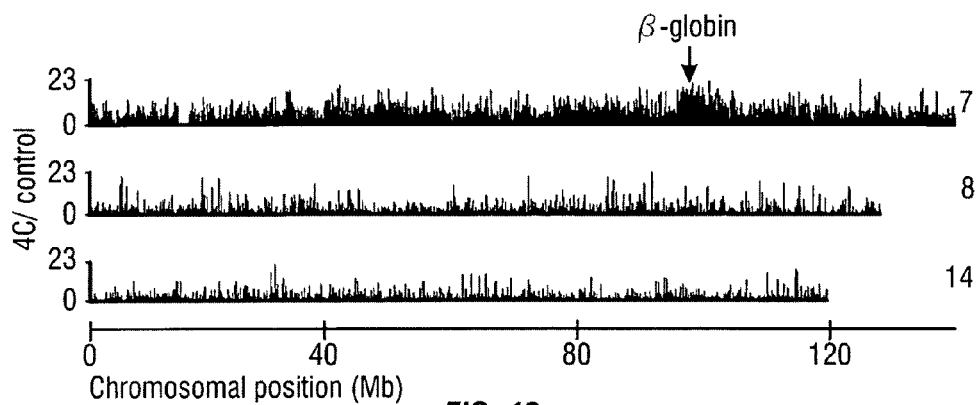

Analysis of 4C Technology Results 4C technology was used to characterise the genomic environment of the mouse β-globin locus control region (LCR), focusing on a restriction fragment containing its hypersensitive site 2 (HS2). The LCR is a strong erythroid-specific transcription regulatory element required for high levels of β-globin gene expression. The β-globin locus is present on chromosome 7 at position 97 Mb, where it resides in a large, 2.9 Mb, cluster of olfactory receptor genes that are transcribed only in olfactory neurons. Interactions were analysed in two tissues: E14.5 fetal liver, where the LCR is active and the β-globin genes are transcribed highly, and E14.5 fetal brain, where the LCR is inactive and the globin genes are silent. In both tissues, the great majority of interactions were found with sequences on chromosome 7 and very few LCR interactions were detected with six unrelated chromosomes (8, 10, 11, 12, 13, 14) (FIG. 13a). The strongest signals on chromosome 7 were found within a 5-10 Mb region centered around the chromosomal position of β-globin, in agreement with the idea that interaction frequencies are inversely proportional to the distance (in basepairs) between physically linked DNA sequences. It was not possible to interpret the interactions in this region quantitatively. We reasoned that these nearby sequences were together with β-globin so frequently that their large overrepresentation in our hybridisation samples saturated the corresponding probes. This was confirmed when we performed hybridizations with samples diluted 1:10 and 1:100 and found that signal intensity was reduced at probes outside and at the edge, but not inside this region (data not shown).

Figure 13B:
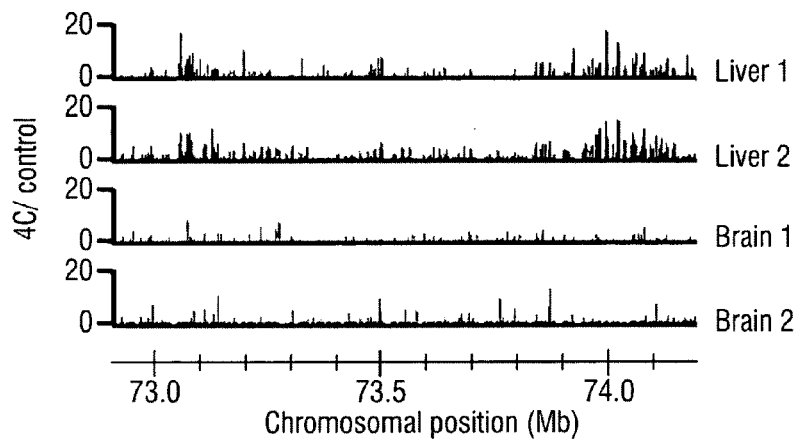
Figure 13C:
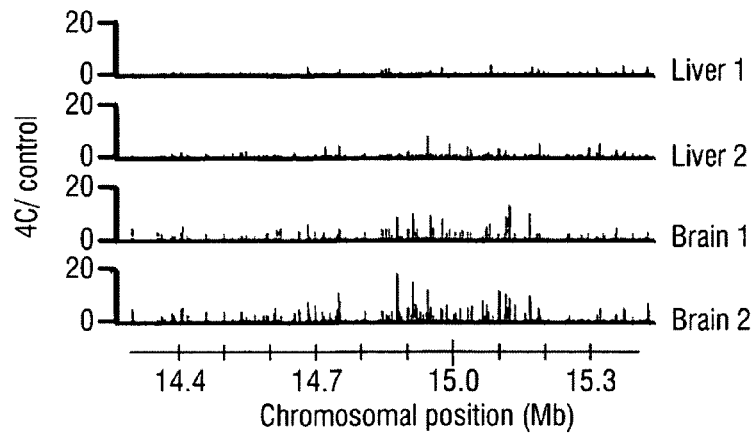

The 4C procedure yielded highly reproducible data. FIG. 2b-c shows unprocessed ratios of 4C-signals over control hybridisation signals for two 1.5 Mb regions on chromosome 7, roughly 25 Mb and 80 Mb away from the J-globin gene. At this level of resolution the results from independently processed samples were almost identical. Both in fetal liver and in brain, clusters of positive signals were identified on chromosome 7, often at chromosomal locations tens of megabases away from β-globin. These clusters typically consisted of minimally 20-50 probes with increased signal ratios juxtaposed on the chromosome template (FIG. 13b-c). Each probe on the array analyses an independent ligation event. Moreover, only two copies of the HS2 restriction fragment are present per cell, each of which can only ligate to one other restriction fragment. Therefore, the detection of independent ligation events with 20 or more neighbouring restriction fragments strongly indicates that the corresponding locus contacts the β-globin LCR in multiple cells.

Figure 13D:
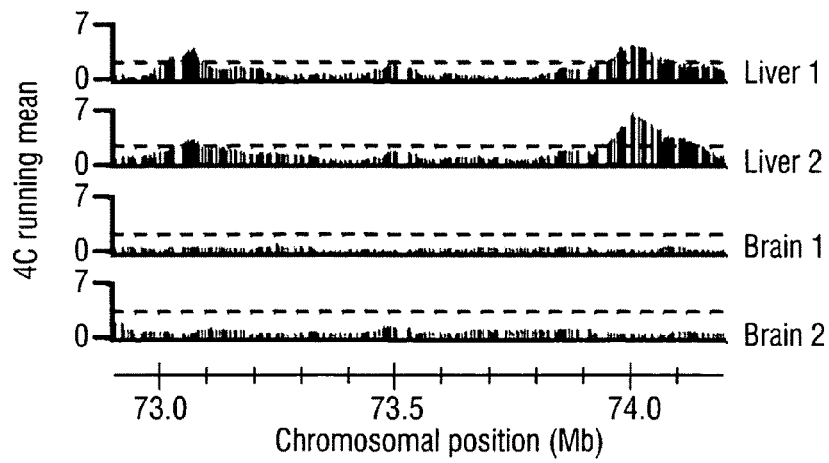
Figure 13E:
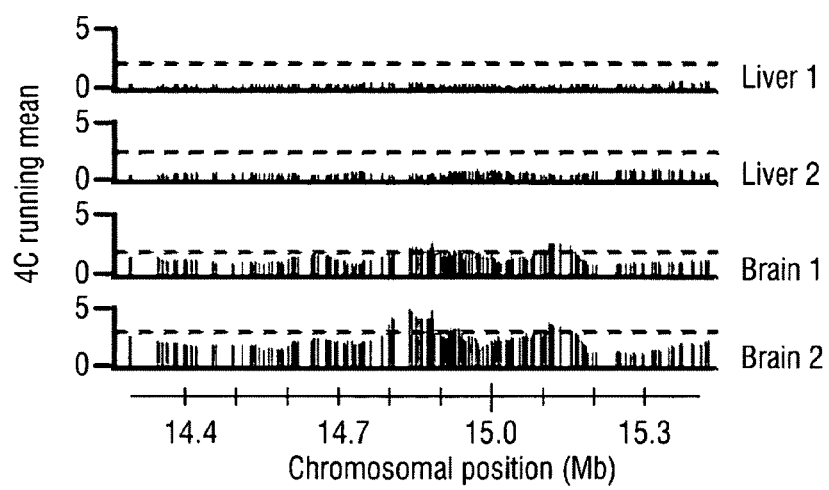
Figure 13F:
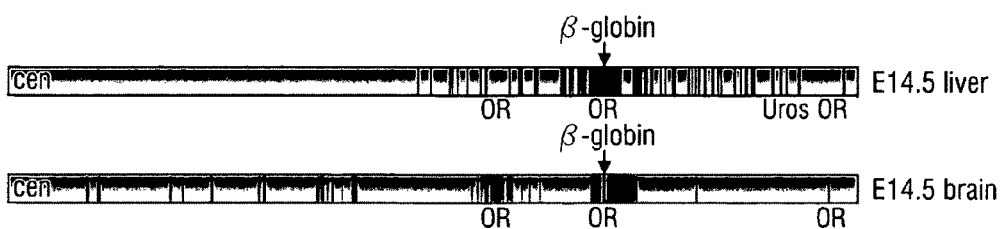
Figure 14A:
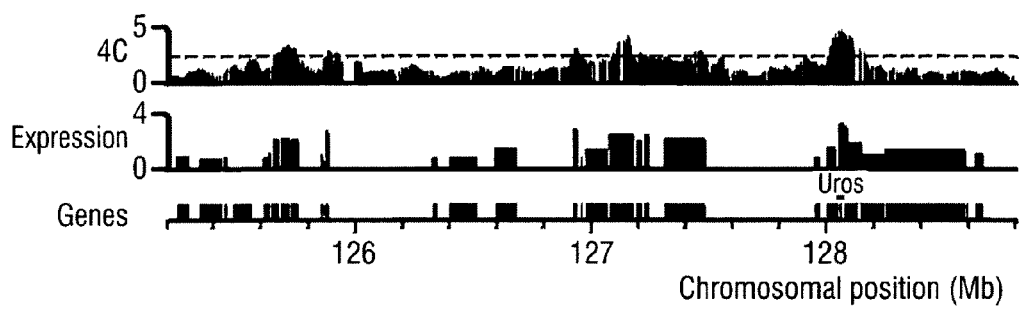
Figure 14B:
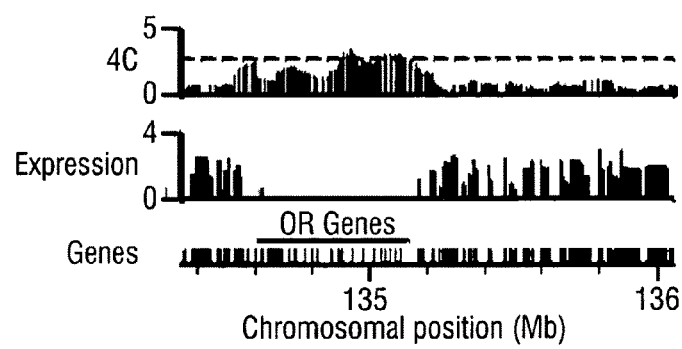
Figure 14C:
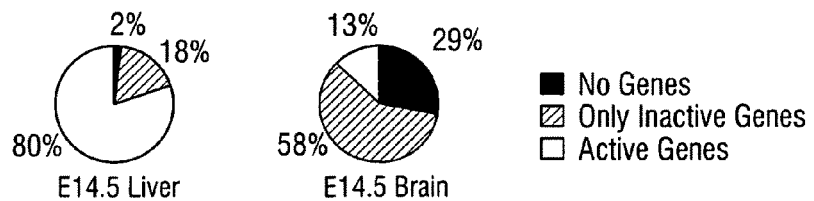

To determine the statistical significance of these clusters, data of individual experiments were ordered on chromosomal maps and analysed using a running mean algorithm with a window size of approximately 60 kb. The running mean distribution of randomly shuffled data was used to set a threshold value, allowing a false discovery rate of 5%. This analysis identified 66 clusters in foetal liver and 45 in brain that reproducibly were found in duplicate experiments (FIG. 13d-f). Indeed, high resolution FISH confirmed that such clusters truly represent loci that interact frequently (see below).

Thus, 4C technology identifies long-range interacting loci by the detection of independent ligation events with multiple restriction fragments clustered at a chromosomal position.

Figure 17A:
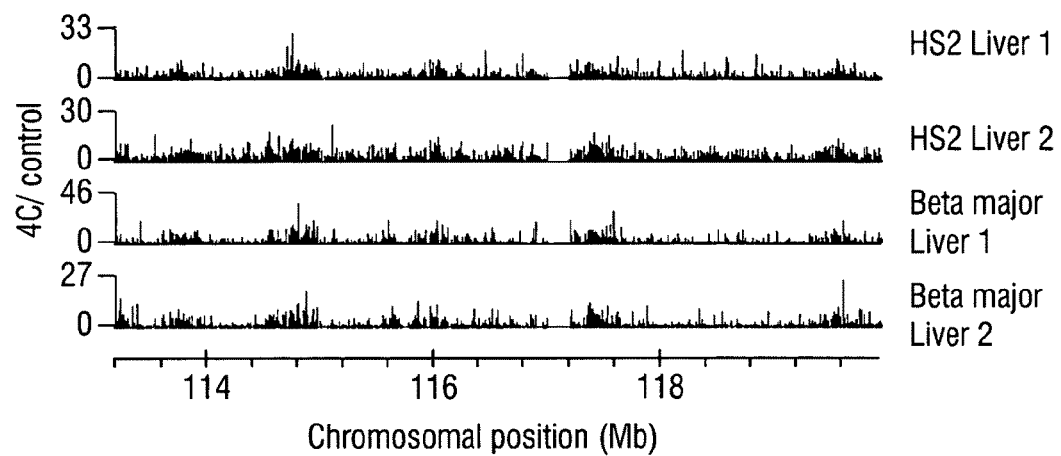
Figure 17B:
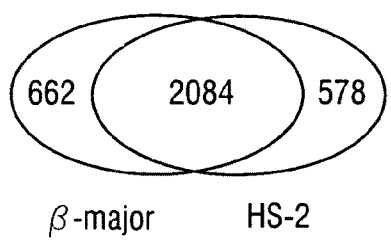
Figure 18A:
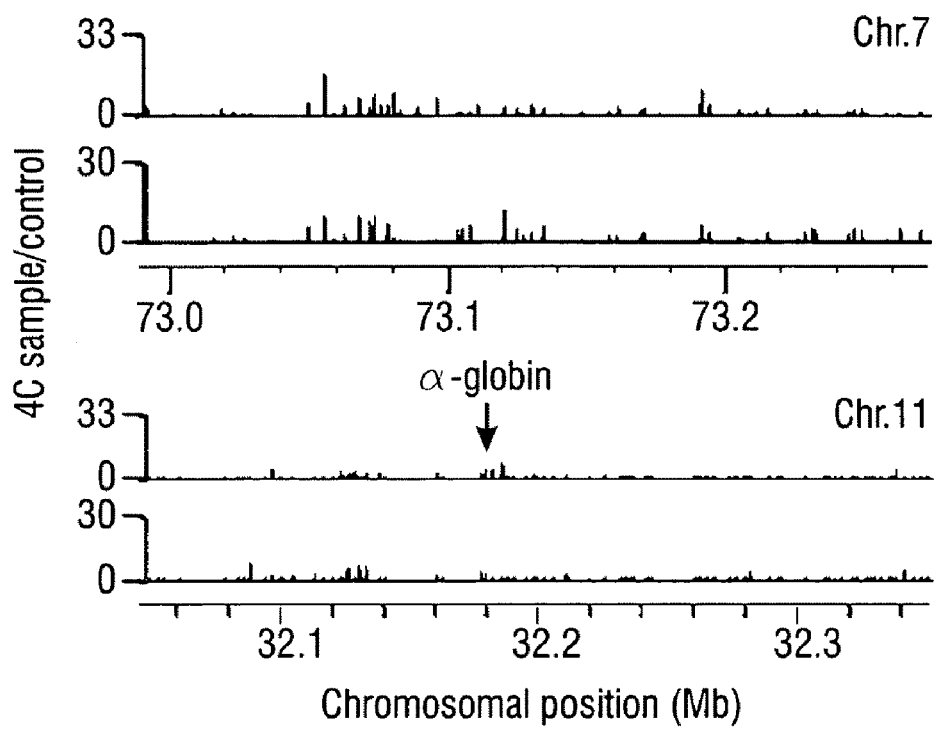
Figure 18B:
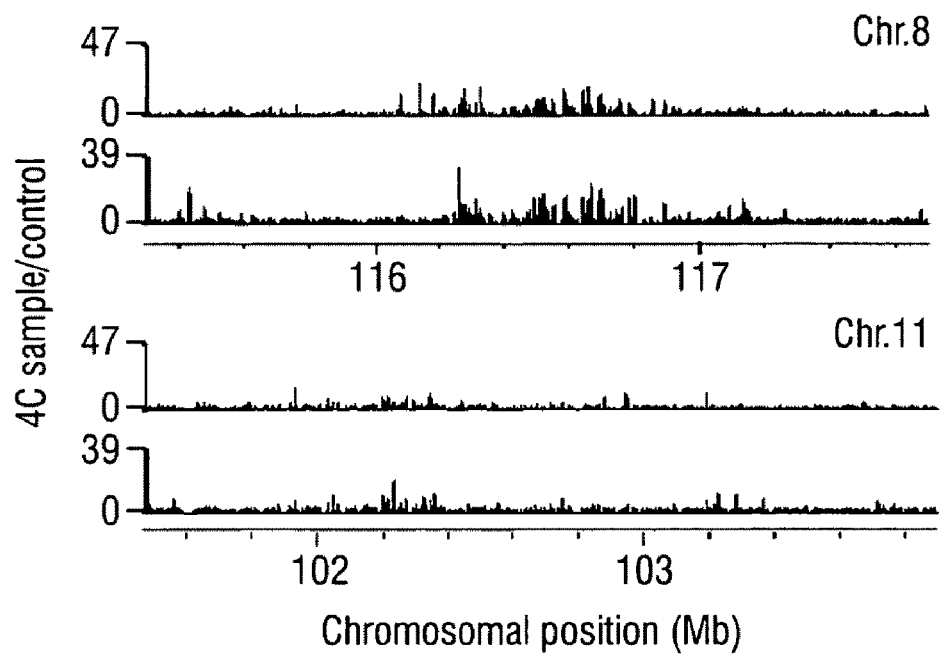

A completely independent series of 4C experiments was performed with a different inverse PCR primerset that investigated the genomic environment of the β major gene, located ~50 kb downstream of HS2. In foetal liver, the β major gene is highly transcribed and frequently contacted by the Almost identical clusters of long-range interactions with β major as with HS2 were found, both in foetal liver and in brain, further substantiating that these loci frequently contact the β-globin locus (FIG. 17).

Example 5

The Active and Inactive β-Globin Locus Occupy Distinct Genomic Environments

A comparison between the two tissues revealed that the actively transcribed β-globin is locus in foetal liver interacts with a completely different set of loci than its transcriptionally silent counterpart in brain ($\tau=-0.03$; Spearman's Rank correlation) (FIG. 13f). This excluded that results were influenced by the sequence composition of the probes. In foetal liver, the interacting DNA segments were located within a 70 Mb region centred around the β-globin locus, with the majority (40/66) located towards the telomere of chromosome 7. In foetal brain, interacting loci were found at similar or even larger distances from β-globin compared to foetal liver and with the great majority of interactions (43/45) located towards the centromere of chromosome 7. These data demonstrated that the active and inactive β-globin locus contact different parts of chromosome 7.

Figure 19:
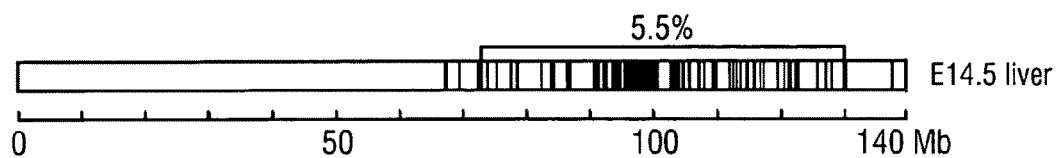

Six other chromosomes (8, 10, 11, 12, 13 and 14) were represented on the micro-arrays. Strong hybridisation signals on these chromosomes were rare, typically appeared isolated on the linear DNA template and often were absent from duplicate experiments. Also, running mean levels across these chromosomes never reproducibly came close to the levels scored for chromosome 7 (FIG. 19). Thus, our data showed that the β-globin locus mostly contacted loci elsewhere on the same chromosome, in agreement with the preferred location of this locus inside its own chromosome territory. We note that the α-globin locus was also present on the array (chromosome 11) and did not score positive for interaction with β-globin, in agreement with the recent demonstration by FISH that mouse α- and β-globin do not frequently meet in the nuclear space (Brown, J. M. et al. (2006) J Cell Biol 172, 177-87).

In order to better understand the relevance of the observed long-range interactions on chromosome 7, we compared the interacting loci to the chromosomal positions of genes. In addition, Affymetrix expression array analysis was performed to determine transcription activity at these positions in the two tissues. Although the average size of interacting areas in foetal liver and brain was comparable (183 kb and 159 kb, respectively), dramatic differences were observed in their gene content and activity. In foetal liver, 80% of the β-globin interacting loci contained one or more actively transcribed genes, while in foetal brain the great majority (87%) showed no detectable gene activity (FIG. 15). Thus, the β-globin locus is embedded in a very different genomic environment in the two tissues. In brain, where the locus is not active, it primarily contacts transcriptional silent loci located towards the centromere of chromosome 7. In foetal liver, where the locus is highly active, it interacts preferentially with actively transcribed regions located more prominently towards the telomeric side of chromosome 7. Importantly, 4C technology identified both Uros and Eraf, (~30 Mb away from β-globin) as genes interacting with the active β-globin locus in fetal liver, in agreement with previous observations made by FISH (Osborne, C. S. et al. (2004) Nat Genet 36, 1065-71 (2004)). Interestingly, in brain contacts were observed with the two other olfactory receptor gene clusters present on chromosome 7 that were located at each side of, and 17 and 37 Mb away from, β-globin.

Not all transcribed regions on chromosome 7 interact with the active β-globin locus in foetal liver. Therefore, we searched for a denominator shared exclusively by the interacting loci but not by other active regions in fetal liver. The β-globin genes, Uros and Eraf are all erythroid-specific genes that may be regulated by the same set of transcription factors, and it is an attractive idea that these factors co-ordinate the expression of their target genes in the nuclear space. We compared Affymetrix expression array data from E14.5 foetal liver with that of foetal brain to identify genes expressed preferentially (>5-fold more) in foetal liver. As such, 28% of the active genes on chromosome 7 were classified as "foetal liver-specific", of which 25% were found in a co-localising area. Thus, we found no enrichment of "foetal liver-specific" genes in the co-localising areas. More importantly, 49 out of 66 (74%) interacting regions did not contain a "foetal liver-specific" and it is therefore concluded that our data showed no evidence for co-ordinate expression of tissue-specific genes in the nuclear space. The β-globin genes are transcribed at exceptional high rates and it was next asked whether the locus preferentially interacted with other regions of high transcriptional activity, being either highly expressed genes or areas with a high density of active genes. Using Affymetrix counts as a measure for gene activity, we performed a running sum algorithm to measure overall transcriptional activity within 200 kb regions around actively transcribed genes. This analysis revealed that transcriptional activity around interacting genes was not higher than around non-interacting active genes on chromosome 7 (p=0.9867; Wilcoxon Rank sum).

Example 6

Figure 15A:
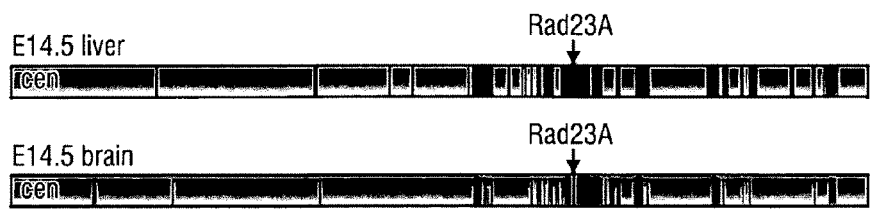
Figure 15B:
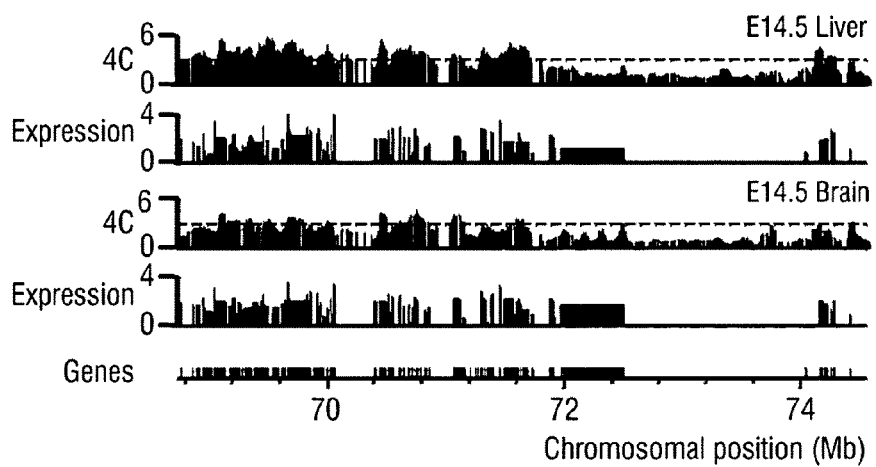
Figure 15C:
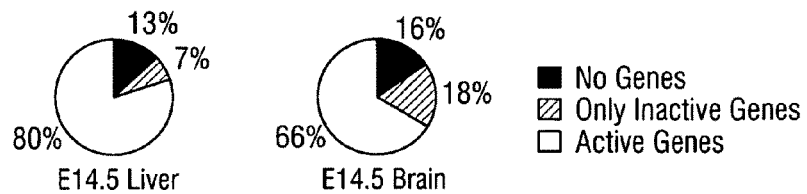
Figure 16:
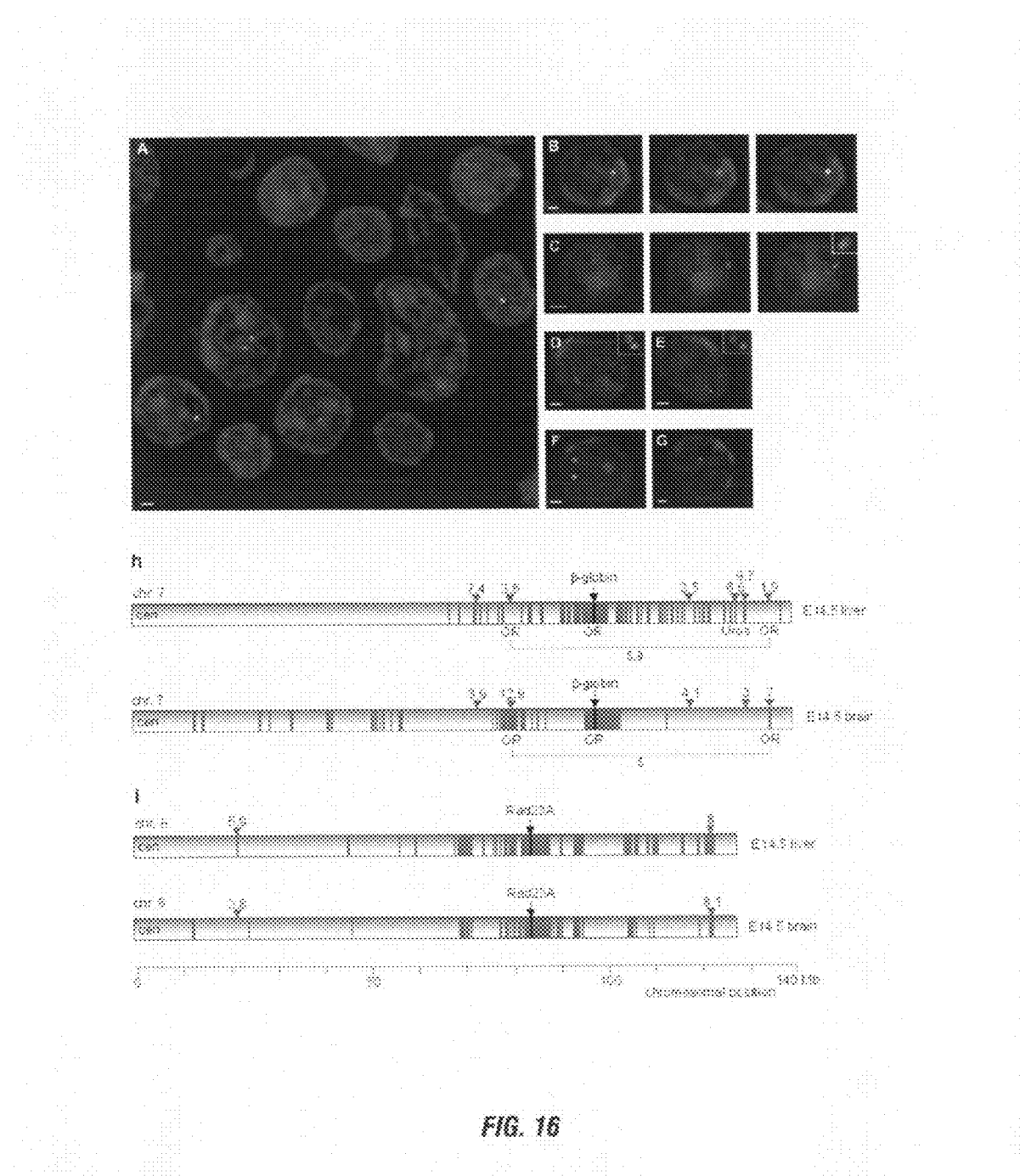

The Genomic Environment of a Housekeeping Gene is Largely Conserved Between the Tissues It was next investigated whether a gene that is expressed similarly in both tissues also switches its genomic environment. Rad23A is a ubiquitously expressed gene that resides in a gene-dense cluster of mostly housekeeping genes on chromosome 8. Both in E14.5 foetal liver and in brain, this gene and many of its direct neighbours are active. 4C analysis was performed and identified many long-range interactions with loci up to 70 Mb away from Rad23A. Importantly, interactions with Rad23A were highly correlated between foetal liver and brain ($\tau$=0.73; Spearman's Rank correlation) (FIG. 15a). A shared hallmark of these loci was again that they contained actively transcribed genes. Thus, in both tissues roughly 70% contained at least one active gene (FIG. 15b-c). Regions around interacting genes displayed statistically significant higher levels of gene activity compared to active genes elsewhere on the chromosome, as determined by a running sum algorithm (p<0.001 for both tissues). Thus, unlike the $\beta$-globin locus, the Rad23A gene that is located in a gene-rich region preferentially interacts over distance with other chromosomal regions of increased transcriptional activity. It was observed by FISH that the chromosomal area containing Rad23A resides mostly at the edge of (90%) or outside (10%) its chromosome territory (unpublished, D. Noordermeer, M. Branco, A. Pombo and W. de Laat). However, the 4C analysis only revealed intra-chromosomal interactions and no area on chromosome 7, 10, 11, 12, 13 or 14 reproducibly met our stringent criteria for interaction. Thus, Rad23A is mostly involved in intra-chromosomal interactions that are similar in two very different tissues. If Rad23A has preferred neighbouring loci on these unrelated chromosomes, they do not interact frequently enough to be detected under the conditions used here for 4C technology.

Example 7

Validation of 4C Technology by High-Resolution Microscopy

To validate the results obtained by 4C technology, cryo-FISH experiments were performed. Cryo-FISH is a recently developed microscopy technique, which has the advantage over current 3D-FISH protocols that it better preserves the nuclear ultra-structure while offering improved resolution in the z-axis by the preparation of ultra-thin cryo-sections (Branco, M. R. & Pombo, A (2006). *PLoS Biol* 4, e138). 4C data were verified by measuring how frequent $\beta$-globin or Rad23A alleles (always n>250) co-localised with more than 15 selected chromosomal regions in 200 nm ultra-thin sections prepared from E14.5 liver and brain. Importantly, all interaction frequencies measured by cryo-FISH were in perfect agreement with the 4C results (FIG. 17). For example, distant regions that were identified to interact with $\beta$-globin by 4C technology co-localised more frequently than intervening areas not detected by 4C (7.4% and 9.7%, versus 3.6% and 3.5%, respectively). Also, the two distant olfactory receptor gene clusters identified by 4C technology to interact with $\beta$-globin in foetal brain but not liver scored co-localisation frequencies respectively of 12.9% and 7% in brain, versus 3.6% and 1.9% in liver sections. In summary, co-localisation frequencies measured for loci positively identified by 4C technology were all significantly higher than frequencies measured for background loci (p<0.05; G-test). We concluded that 4C technology faithfully identified interacting DNA loci. Finally, we used cryo-FISH to demonstrate that loci identified to interact with $\beta$-globin also frequently contacted each other. This was true for two active regions separated over large chromosomal distance in foetal liver (FIG. 19) as well as for two inactive OR gene clusters far apart on the chromosome in brain (FIG. 17). Interestingly, frequent contacts between these two distant OR gene clusters were also found in foetal liver, where they did not interact with the OR gene cluster that contained the actively transcribed $\beta$-globin locus. These data indicated that nuclear interactions between distinct OR gene clusters were not a peculiarity of the foetal brain tissue analysed. It is tempting to speculate that such spatial contacts facilitate the communication between the many OR genes required to ensure that only a single allele is transcribed per olfactory neuron (Shykind, B. (2005) *Hum Mol Genet* 14 Spec No 1, R33-9.

Example 8

Nuclear Organisation of Active and Inactive Chromatin Domains

The observations described herein demonstrate that not only active, but also inactive genomic regions form distinct regions in the nuclear space that involve many long-range contacts, strongly suggesting that each DNA segment has its own preferred set of interactions. Our data suggest that when the $\beta$-globin locus is switched on, it leaves a transcriptional silent genomic environment and enters a nuclear area where interactions with active domains are favoured. It is anticipated that such a dramatic repositioning upon transcriptional activation may well be a hallmark only of tissue-specific genes that reach a certain expression level and, more importantly, lie isolated from other active genes on the linear chromosome template, as is the case for $\beta$-globin. It is proposed that the extensive network of long-range interactions that are identified both between inactive and between active genomic loci, reflects cell-to-cell differences in chromosome conformations more than being a consequence of dynamic movements during interphase (Chakalova et al. (2005) *Nat Rev Genet* 6, 669-77 (2005). Presumably, different degrees of de-condensation after cell division drive the active genomic regions away from inactive chromatin (Gilbert, N. et al. (2004) *Cell* 118, 555-66 (2004)) and contacts between distant loci of similar chromatin composition are stabilised mostly through affinities between chromatin-bound proteins. Spatial juxtaposition between distant loci may be functional, but may also simply be the consequence of the unfolding patterns of a chromosome. While individual loci can move within a restricted nuclear volume, the general conformation of a chromosome would largely be maintained throughout the cell cycle and requiring cell division for resetting. This idea is in agreement with life cell imaging studies showing restricted motion of tagged DNA loci in the nuclear interior (Chubb et al. (2002) *Curr Biol* 12, 439-45 (2002)) and fits well with studies showing that nuclear chromatin position information is frequently propagated during the cell division without being conserved in the population of cells (Essers, J. et al. *Mol Biol Cell* 16, 769-75 (2005); Gerlich, D. et al. *Cell* 112, 751-64 (2003)).

Further Aspects 1

Further aspects of the present invention are set forth below in the numbered paragraphs.

1. A set of probes complementary to every side of every primary restriction enzyme recognition site in the genome of a given species (e.g. human).

2. A set of probes complementary to only one side of every primary restriction enzyme recognition site in the genome of a given species (e.g. human).

3. A set of probes complementary to one side of every other primary restriction enzyme recognition site as ordered along the linear template of the genome of a given species (e.g. human).

4. A set of probes complementary to one side of every third, fourth, fifth, sixth, seventh, eight, ninth, tenth, twentieth, thirtieth, fortieth, fiftieth, sixtieth, seventieth eightieth, ninetieth or one hundredth primary restriction enzyme recognition site as ordered along the linear template of the genome of a given species (e.g. human).

5. A set of probes representing genomic regions of a given size (e.g. about 50 kb, 100 kb, 200 kb, 300 kb, 400 kb, 500 kb, 1 Mb, 2 Mb, 3 Mb, 4 Mb, 5 Mb, 6 Mb, 6 Mb, 7 Mb, 8 Mb, 9 Mb or 10 Mb) (e.g. 50 kb-10 Mb) around all loci known to be involved in translocations, deletions, inversions, duplications and other genomic rearrangements.

6. A set of probes representing genomic regions of a given size (e.g. about 50 kb, 100 kb, 200 kb, 300 kb, 400 kb, 500 kb, 1 Mb, 2 Mb, 3 Mb, 4 Mb, 5 Mb, 6 Mb, 6 Mb, 7 Mb, 8 Mb, 9 Mb or 10 Mb) (e.g. 50 kb-10 Mb) around a selection of loci known to be involved in translocations, deletions, inversions, duplications and other genomic rearrangements.

7. Preferably, the 4C sequence (bait) is within about 50 kb, 100 kb, 200 kb, 300 kb, 400 kb, 500 kb, 1 Mb, 2 Mb, 3 Mb, 4 Mb, 5 Mb, 6 Mb, 6 Mb, 7 Mb, 8 Mb, 9 Mb, 10 Mb, 11 Mb, 12 Mb, 13 Mb, 14 Mb or 15 Mb or more from the actual rearranged sequence (i.e. breakpoint in case of a translocation).

8. A set of probes representing the complete genome of a given species, with each probe representing a single restriction fragment as obtained or obtainable after digestion with a primary restriction enzyme.

9. A set of probes representing the complete genome of a given species, with probes equally distributed along the linear chromosome templates.

10. An array comprising the set of probes according to any of paragraphs 1-10.

11. A method for analysing the frequency of interaction of a target nucleotide sequence with one or more nucleotide sequences (e.g. one or more genomic loci) comprising the use of a nucleotide sequence or an array of probes or a set of probes or an array as described herein.

12. A method for identifying one or more DNA-DNA interactions that are indicative of a particular disease state comprising the use of a nucleotide sequence or an array of probes or a set of probes or an array as described herein.

13. A method of diagnosis or prognosis of a disease or syndrome caused by or associated with a change in a DNA-DNA comprising the use of a nucleotide sequence or an array of probes or a set of probes or an array as described herein.

14. An assay method for identifying one or more agents that modulate a DNA-DNA interaction comprising the use of a nucleotide sequence or an array of probes or a set of probes or an array as described herein.

15. A method for detecting the location of a breakpoint (e.g. a translocation) comprising the use of a nucleotide sequence or an array of probes or a set of probes or an array as described herein.

16. A method for detecting the location of an inversion comprising the use of a nucleotide sequence or an array of probes or a set of probes or an array as described herein.

17. A method for detecting the location of a deletion comprising the use of a nucleotide sequence or an array of probes or a set of probes or an array as described herein.

18. A method for detecting the location of a duplication comprising the use of a nucleotide sequence or an array of probes or a set of probes or an array as described herein.

19. The use of microarrays in 4C technology to identify (all) DNA segments that are in close spatial proximity to a DNA segment of choice.

20. A microarray containing probes homologous to DNA sequences directly adjacent to the primary restriction enzyme recognition sites present in the genomic region that is included in the analysis (which can be the complete genome or part of the genome): each probe locates preferably within 100 bp from, or maximally within 300 bp from, a unique primary restriction enzyme recognition site, or alternatively is designed between each primary restriction enzyme recognition site and its closest secondary restriction enzyme recognition site.

21. An array as described herein comprising probes complementary to sequences of selected loci, wherein said array is representative of the complete genome of a given species.

22. An array according to paragraph 21, wherein the loci are loci associated with one or more diseases.

23. An array according to paragraph 21 or paragraph 22, wherein the sequences of selected loci included sequences that are up to 20 Mb away from said loci.

24. A method for analysing the frequency of interaction of a target nucleotide sequence with one or more nucleotide sequences of interest (e.g. one or more genomic loci) comprising the steps of:
(a) providing a sample of cross-linked DNA;
(b) digesting the cross-linked DNA with a primary restriction enzyme;
(c) ligating the cross-linked nucleotide sequences;
(d) reversing the cross linking;
(e) digesting the nucleotide sequences with a secondary restriction enzyme;
(f) ligating the nucleotide sequences;
(g) amplifying the one or more nucleotide sequences of interest that are ligated to the target nucleotide sequence using at least two oligonucleotide primers, wherein each primer hybridises to a known DNA sequence that flanks the nucleotide sequences of interest;
(h) hybridising the amplified sequence(s) to an array; and
(i) determining the frequency of interaction between the DNA sequences.

Further Aspects 2

Still further aspects of the present invention are set forth below in the numbered paragraphs.

1. A circularised nucleotide sequence comprising a first and a second nucleotide sequence separated by a primary and a secondary restriction enzyme recognition site, wherein said first nucleotide sequence is a target nucleotide sequence and said second nucleotide sequence is obtainable by cross-linking genomic DNA.

2. The circularised nucleotide sequence according to paragraph 1, wherein the target nucleotide sequence is selected from the group consisting of a promoter, an enhancer, a silencer, an insulator, a matrix attachment region, a locus control region, a transcription unit, an origin of replication, a recombination hotspot, a translocation breakpoint, a centromere, a telomere, a gene-dense region, a gene-poor region, a repetitive element and a (viral) integration site.

3. The circularised nucleotide sequence according to paragraph 1, wherein the target nucleotide sequence is a nucleotide sequence that is associated with or causes a disease, or is located less then 15 Mb on a linear DNA template from a locus that is associated with or causes a disease.

4. The circularised nucleotide sequence according to any of paragraphs 1-3, wherein the target nucleotide sequence is selected from the group consisting of: AML1, MLL, MYC, BCL, BCR, ABL1, IGH, LYL1, TAL1, TAL2, LMO2, TCRα/δ, TCRβ and HOX or other loci associated with disease as described in "Catalogue of Unbalanced Chromosome Aberrations in Man" 2nd edition. Albert Schinzel. Berlin: Walter de Gruyter, 2001. ISBN 3-11-011607-3.

5. The circularised nucleotide sequence according to any of paragraphs 1-4, wherein the primary restriction enzyme recognition site is a 6-8 bp recognition site, preferably selected from the group consisting of BglII, HindIII, EcoRI, BamHI, SpeI, PstI and NdeI.

6. The circularised nucleotide sequence according to any of the preceding paragraphs, wherein the secondary restriction enzyme recognition site is a 4 or 5 bp nucleotide sequence recognition site.

7. The circularised nucleotide sequence according to any of the preceding paragraphs, wherein the secondary restriction enzyme recognition site is located at greater than about 350 bp from the primary restriction site.

8. The circularised nucleotide sequence according to any of the preceding paragraphs, wherein the nucleotide sequence is labelled.

9. A nucleotide sequence comprising a first and a second nucleotide sequence separated by a primary and a secondary restriction enzyme recognition site, wherein said first nucleotide sequence is a target nucleotide sequence, the second nucleotide sequence is obtainable by cross-linking genomic DNA and wherein said second nucleotide sequence intersects the target nucleotide sequence.

10. A method for preparing a circularised nucleotide sequence comprising the steps of:
(a) providing a sample of cross-linked DNA;
(b) digesting the cross-linked DNA with a primary restriction enzyme;
(c) ligating the cross-linked nucleotide sequences;
(d) reversing the cross linking;
(e) digesting the nucleotide sequences with a secondary restriction enzyme; and
(f) circularising the nucleotide sequences.

11. A method for preparing a nucleotide sequence comprising the steps of:
(a) providing a sample of cross-linked DNA;
(b) digesting the cross-linked DNA with a primary restriction enzyme;
(c) ligating the cross-linked nucleotide sequences;
(d) reversing the cross linking;
(e) digesting the nucleotide sequences with a secondary restriction enzyme;
(f) circularising the nucleotide sequences; and
(g) amplifying the one or more nucleotide sequences ligated to the target nucleotide sequence.

12. A method according to paragraph 11, wherein the circularised target nucleotide sequence is linearised before amplification.

13. A method according to paragraph 12, wherein the circularised target nucleotide sequence is linearised using a restriction enzyme that recognises a 6 bp or more recognition site.

14. A method according to any of paragraphs 10-13, wherein the cross-linked nucleotide sequence is amplified using PCR.

15. A method according to paragraph 14, wherein the cross-linked nucleotide sequence is amplified using inverse PCR.

16. A method according to paragraph 14 or paragraph 15, wherein the Expand Long Template PCR System (Roche) is used.

17. A method for analysing the frequency of interaction of a target nucleotide sequence with one or more nucleotide sequences (e.g. one or more genomic loci) comprising the use of a nucleotide sequence according to any of paragraphs 1-9.

18. An array of probes immobilised on a support comprising one or more probes that hybridise or are capable of hybridising to a nucleotide sequence according to any of paragraphs 1-9.

19. A set of probes complementary in sequence to the nucleic acid sequence adjacent to each one of the primary restriction enzyme recognition sites of a primary restriction enzyme in genomic DNA.

20. A set of probes according to paragraph 19, wherein the probes are complementary in sequence to the nucleic acid sequence adjacent each side of each one of the primary restriction enzyme recognition sites of a primary restriction enzyme in genomic DNA.

21. A set of probes according to paragraph 19 or paragraph 20, wherein said probes are complementary in sequence to the nucleic acid sequence that is less than 300 base pairs from each one of the primary restriction enzyme recognition sites of a primary restriction enzyme in genomic DNA.

22. A set of probes according to any of paragraphs 19-21, wherein the probes are complementary to the sequence that is less then 300 bp from each one of the primary restriction enzyme recognition sites of a primary restriction enzyme in genomic DNA.

23. A set of probes according to any of paragraphs 19-22, wherein the probes are complementary to the sequence that is between 200 and 300 bp from each one of the primary restriction enzyme recognition sites of a primary restriction enzyme in genomic DNA.

24. A set of probes according to any of paragraphs 19-23, wherein the probes are complementary to the sequence that is between 100 and 200 bp from each one of the primary restriction enzyme recognition sites of a primary restriction enzyme in genomic DNA.

25. A set of probes according to any of paragraphs 19-24, wherein two or more probes are designed that are capable of hybridising to the sequence adjacent each primary restriction enzyme recognition site of a primary restriction enzyme in the genomic DNA.

26. A set of probes according to paragraph 25, wherein the probes overlap or partially overlap.

27. A set of probes to paragraph 26, wherein the overlap is less than 10 nucleotides.

28. A set of probes according to any of paragraphs 19-27, wherein the probe sequence corresponds to all or part of the sequence between each one of the primary restriction enzyme recognition sites of a primary restriction enzyme and each one of the first neighbouring secondary restriction enzyme recognition sites of a secondary restriction enzyme.

29. A set of probes according to any of paragraphs 19-28, wherein each probe is at a least a 25 mer.

30. A set of probes according to any of paragraphs 19-29, wherein each probes is a 25-60 mer.

31. A process for preparing a set of probes comprising the steps of:
(a) identifying each one of the primary restriction enzyme recognition sites for a primary restriction enzyme in genomic DNA;
(b) designing probes that are capable of hybridising to the sequence adjacent each one of the primary restriction enzyme recognition sites in the genomic DNA;
(c) synthesising the probes; and
(d) combining the probes together to form a set of probes or substantially a set of probes.

32. A process according to paragraph 31, wherein the probes are PCR amplification products.

33. A set of probes or substantially a set of probes obtained or obtainable by the process according to paragraph 31 or paragraph 32.

34. An array comprising the array of probes according to paragraph 18 or substantially the set of probes according to any of paragraphs 19-30 or 33.

35. An array comprising the set of probes according to any of paragraphs 19-30 or 33.

36. An array according to paragraph 34 or paragraph 35, wherein the array comprises about 300,000-400,000 probes.

37. An array according to any of paragraphs 34-36, wherein the array comprises about 385,000 or more probes, preferably, about 750,000 probes, more preferably, 6×750,000 probes.

38. An array according to any of paragraphs 34-37, wherein if the number of probes exceeds the number of probes that can be contained in a single array, then the array comprises or consists of a representation of the complete genome of a given species at lower resolution.

39. An array according to paragraph 38, wherein one out of every 2, 3, 4, 5, 6, 7, 8, 9 or 10 probes as ordered on a linear chromosome template is contained in the array.

40. A process for preparing an array comprising the step of immobilising on a solid support substantially the array of probes according to paragraph 18 or substantially the set of probes according to any of paragraphs. 19-30 or 33.

41. A process for preparing an array comprising the step of immobilising on a solid support the array of probes according to paragraph 18 or the set of probes according to any of paragraphs 19-30 or 33.

42. An array obtained or obtainable by the method according to paragraph 40 or paragraph 41.

43. A method for analysing the frequency of interaction of a target nucleotide sequence with one or more nucleotide sequences (e.g. one or more genomic loci) comprising the steps of:
(a) providing a sample of cross-linked DNA;
(b) digesting the cross-linked DNA with a primary restriction enzyme;
(c) ligating the cross-linked nucleotide sequences;
(d) reversing the cross linking;
(e) digesting the nucleotide sequences with a secondary restriction enzyme;
(f) circularising the nucleotide sequences;
(g) amplifying the one or more nucleotide sequences that are ligated to the target nucleotide sequence;
(h) optionally hybridising the amplified sequences to an array; and
(i) determining the frequency of interaction between the DNA sequences.

44. A method for identifying one or more DNA-DNA interactions that are indicative of a particular disease state comprising the steps of
(a) providing a sample of cross-linked DNA from a diseased and a non-diseased cell;
(b) digesting the cross-linked DNA in each of the samples with a primary restriction enzyme;
(c) ligating the cross-linked nucleotide sequences;
(d) reversing the cross linking;
(e) digesting the nucleotide sequences with a secondary restriction enzyme;
(f) circularising the nucleotide sequences;
(g) amplifying the one or more sequences that are ligated to the target nucleotide sequence;
(h) optionally hybridising the amplified nucleotide sequences to an array; and
(i) determining the frequency of interaction between the DNA sequences,
wherein a difference between the frequency of interaction between the DNA sequences from the diseased and non-diseased cells indicates that the DNA-DNA interaction is indicative of a particular disease state.

45. A method of diagnosis or prognosis of a disease or syndrome caused by or associated with a change in a DNA-DNA interaction comprising the steps of
(a) providing a sample of cross-linked DNA from a subject;
(b) digesting the cross-linked DNA with a primary restriction enzyme;
(c) ligating the cross-linked nucleotide sequences;
(d) reversing the cross linking;
(e) digesting the nucleotide sequences with a secondary restriction enzyme;
(f) circularising the nucleotide sequences;
(g) amplifying the one or more sequences that are ligated to the target nucleotide sequence;
(h) optionally hybridising the amplified nucleotide sequences to an array;
(i) determining the frequency of interaction between the DNA sequences; and
(j) comparing the frequency of interaction between the DNA sequences with that of an unaffected control;
wherein a difference between the value obtained from the control and the value obtained from the subject is indicative that the subject is suffering from the disease or syndrome or is indicative that the subject will suffer from the disease or syndrome.

46. A method according to paragraph 45, wherein a transition from low to high interaction frequencies is indicative of the location of a breakpoint.

47. A method according to paragraph 45 wherein an inversed pattern of DNA-DNA interaction frequencies for the subject sample as compared to the control is indicative of an inversion.

48. A method according to paragraph 45 wherein a reduction in the DNA-DNA interaction frequency for the subject sample as compared to the control, in combination with an increase in DNA-DNA interaction frequency for more distant regions, is indicative of deletion.

49. A method according to paragraph 45, wherein an increase or a decrease in DNA-DNA interaction frequency for the subject sample as compared to the control is indicative of a duplication or insertion.

50. A method according to any of paragraphs 45-49, wherein spectral karyotyping and/or FISH is used prior to performing said method.

51. A method according to any of paragraphs 45-50, wherein the disease is a genetic disease.

52. A method according to any of paragraphs 45-51, wherein the disease is cancer.

53. A method of diagnosis or prognosis of a disease or syndrome caused by or associated with a change in a DNA-DNA interaction comprising the steps of
(a) providing a sample of cross-linked DNA from a subject;
(b) digesting the cross-linked DNA with a primary restriction enzyme;
(c) ligating the cross-linked nucleotide sequences;
(d) reversing the cross linking;
(e) digesting the nucleotide sequences with a secondary restriction enzyme;
(f) circularising the nucleotide sequences;
(g) amplifying two or more sequences that are ligated to the target nucleotide sequence(s);
(h) labelling the two or more amplified sequences;
(i) hybridising the nucleotide sequences to an array;
(j) determining the frequency of interaction between the DNA sequences; and
(j) identifying one or more loci that have undergone a genomic rearrangement that is associated with a disease.

54. A method according to paragraph 53, wherein the two or more amplified sequences are differentially labelled.

55. A method according to paragraph 54, wherein the two or more amplified sequences are identically labelled when the sequences reside on different chromosomes.

56. A method according to paragraph 53, wherein the two or more amplified sequences are identically labelled when the sequences reside on the same chromosome at a distance that is far enough for minimal overlap between DNA-DNA interaction signals.

57. An assay method for identifying one or more agents that modulate a DNA-DNA interaction comprising the steps of
(a) contacting a sample with one or more agents;
(b) providing cross-linked DNA from the sample;
(c) digesting the cross-linked DNA with a primary restriction enzyme;
(d) ligating the cross-linked nucleotide sequences;
(e) reversing the cross linking;
(f) digesting the nucleotide sequences with a secondary restriction enzyme;
(g) circularising the nucleotide sequences;
(h) amplifying the one or more nucleotide sequences that are ligated to the target nucleotide sequence;
(i) optionally hybridising the amplified nucleotide sequences to an array; and
(j) determining the frequency of interaction between the DNA sequences,
wherein a difference between (i) the frequency of interaction between the DNA sequences in the presence of the agent and (ii) the frequency of interaction between the DNA sequences in the absence of the agent is indicative of an agent that modulates the DNA-DNA interaction.

58. A method for detecting the location of a breakpoint (e.g. a translocation) comprising the steps of:
(a) providing a sample of cross-linked DNA;
(b) digesting the cross-linked DNA with a primary restriction enzyme;
(c) ligating the cross-linked nucleotide sequences;
(d) reversing the cross linking;
(e) digesting the nucleotide sequences with a secondary restriction enzyme;
(f) circularising the nucleotide sequences;
(g) amplifying the one or more sequences that are ligated to the target nucleotide sequence;
(h) optionally hybridising the amplified nucleotide sequences to an array;
(i) determining the frequency of interaction between the DNA sequences; and
(j) comparing the frequency of interaction between the DNA sequences with that of a control;
wherein a transition from low to high DNA-DNA interaction frequency in the sample as compared to the control is indicative of the location of a breakpoint.

59. A method for detecting the location of an inversion comprising the steps of:
(a) providing a sample of cross-linked DNA;
(b) digesting the cross-linked DNA with a primary restriction enzyme;
(c) ligating the cross-linked nucleotide sequences;
(d) reversing the cross linking;
(e) digesting the nucleotide sequences with a secondary restriction enzyme;
(f) circularising the nucleotide sequences;
(g) amplifying the one or more sequences that are ligated, to the target nucleotide sequence;
(h) optionally hybridising the amplified nucleotide sequences to an array;
(i) determining the frequency of interaction between the DNA sequences; and
(j) comparing the frequency of interaction between the DNA sequences with that of a control;
wherein an inversed pattern of DNA-DNA interaction frequencies for the sample as compared to the control is indicative of an inversion.

60. A method for detecting the location of a deletion comprising the steps of:
(a) providing a sample of cross-linked DNA;
(b) digesting the cross-linked DNA with a primary restriction enzyme;
(c) ligating the cross-linked nucleotide sequences;
(d) reversing the cross linking;
(e) digesting the nucleotide sequences with a secondary restriction enzyme;
(f) circularising the nucleotide sequences;
(g) amplifying the one or more sequences that are ligated to the target nucleotide sequence;
(h) optionally hybridising the amplified nucleotide sequences to an array;
(i) determining the frequency of interaction between the DNA sequences; and
(j) comparing the frequency of interaction between the DNA sequences with that of a control;
wherein a reduction in the DNA-DNA interaction frequency for the sample as compared to the control is indicative of deletion.

61. A method for detecting the location of a duplication comprising the steps of:
(a) providing a sample of cross-linked DNA;
(b) digesting the cross-linked DNA with a primary restriction enzyme;
(c) ligating the cross-linked nucleotide sequences;
(d) reversing the cross linking;
(e) digesting the nucleotide sequences with a secondary restriction enzyme;
(f) circularising the nucleotide sequences;
(g) amplifying the one or more sequences that are ligated to the target nucleotide sequence;
(h) optionally hybridising the amplified nucleotide sequences to an array;
(i) determining the frequency of interaction between the DNA sequences; and (j) comparing the frequency of interaction between the DNA sequences with that of a control;

wherein an increase or a decrease in DNA-DNA interaction frequency for the subject sample as compared to the control is indicative of a duplication or insertion.

75. An assay method substantially as described herein and with reference to any of the Examples or Figures.

76. An agent substantially as described herein and with reference to any of the Examples or Figures.

77. A use substantially as described herein and with reference to any of the Examples or Figures.

TABLE 2

| Interaction | in 4C | N | % overlapping | in Cryo-FISH | P value |
|---|---|---|---|---|---|
| B-globin - Chr.7 73.1 Mb | + | 258 | 7.4 | + | P < 0.001 |
| B-globin - Chr.7 80.1 Mb (OR) | − | 254 | 3.6 | − | |
| B-globin - Chr.7 118.3 Mb | − | 255 | 3.5 | | |
| B-globin - Chr.7 127.9 Mb (Uros) | + | 259 | 6.6 | + | P < 0.001 |
| B-globin - Chr.7 130.1 Mb | + | 413 | 9.7 | + | P < 0.001 |
| B-globin - Chr.7 135.0 Mb (OR) | − | 261 | 1.9 | − | |
| B-globin - D7Mit21 | × | 258 | 0.4 | − | |
| Chr.7 80.1 Mb - Chr.7 135.0 Mb | × | 253 | 5.9 | + | P < 0.05 |
| Chr.7 73.1 Mb - Chr.7 130.1 Mb | × | 254 | 5.5 | + | P < 0.05 |
| Rad23A - Chr.8 21.8 Mb | + | 255 | 5.9 | + | P < 0.05 |
| Rad23A - Chr.8 122.4 Mb | + | 261 | 8 | + | P < 0.001 |
| B-globin - Chr.7 73.1 Mb | − | 256 | 3.9 | − | |
| B-globin - Chr.7 80.1 Mb (OR) | + | 256 | 12.9 | + | P < 0.001 |
| B-globin - Chr.7 118.3 Mb | − | 242 | 4.1 | − | |
| B-globin - Chr.7 130.1 Mb | − | 263 | 3 | − | |
| B-globin - Chr.7 135.0 Mb (OR) | + | 256 | 7 | + | P < 0.05 |
| B-globin - D7Mit21 | | 258 | 6.2 | + | P < 0.05 |
| Chr.7 80.1 Mb - Chr.7 135 Mb | | 261 | 5 | + | P < 0.1 |
| Rad23A - Chr.8 21.8 Mb | − | 260 | 3.8 | − | |
| Rad23A - Chr.8 122.3 Mb | + | 258 | 8.1 | + | P < 0.001 |

62. An agent obtained or obtainable by the assay method according to paragraph 57.

63. Use of a nucleotide sequence according to any of paragraphs 1-9 for identifying one or more DNA-DNA interactions in a sample.

64. Use of a nucleotide sequence according to any of paragraphs 1-9 for the diagnosis or prognosis of a disease or syndrome caused by or associated with a change in a DNA-DNA interaction.

65. Use of an array of probes according to paragraph 18 or the set of probes according to any of paragraphs 19-30 or 33 for identifying one or more DNA-DNA interactions in a sample.

66. Use of an array of probes according to paragraph 18 or the set of probes according to any of paragraphs 19-30 or 33 for the diagnosis or prognosis of a disease or syndrome caused by or associated with a change in a DNA-DNA interaction.

67. Use of an array according to any of paragraphs 34-39 or 42 for identifying one or more DNA-DNA interactions in a sample.

68. Use of an array according to any of paragraphs 34-39 or 42 for the diagnosis or prognosis of a disease or syndrome caused by or associated with a change in a DNA-DNA interaction.

69. Use according to any of paragraphs 64, 66 or 68, wherein the diagnosis or prognosis is prenatal diagnosis or prognosis.

70. A method substantially as described herein and with reference to any of the Examples or Figures.

71. An array of probes substantially as described herein and with reference to any of the Examples or Figures.

72. A set of probes substantially as described herein and with reference to any of the Examples or Figures.

73. A process substantially as described herein and with reference to any of the Examples or Figures.

74. An array substantially as described herein and with reference to any of the Examples or Figures.

REFERENCES

Blanton J, Gaszner M, Schedl P. 2003. Protein:protein interactions and the pairing of boundary elements in vivo. Genes Dev 17:664-75.

Dekker, J., Rippe, K., Dekker, M., and Kleckner, N. 2002. Capturing chromosome conformation. Science 295: 1306-11.

Drissen R, Palstra R J, Gillemans N, Splinter E, Grosveld F, Philipsen S, de Laat W. 2004. The active spatial organization of the beta-globin locus requires the transcription factor EKLF. Genes Dev 18:2485-90.

Horike S, Cai S, Miyano M, Cheng J F, Kohwi-Shigematsu T. 2005. Loss of silent-chromatin looping and impaired imprinting of DLX5 in Rett syndrome. Nat Genet. 37:31-40.

Murrell A, Heeson S, Rea W. 2004. Interaction between differentially methylated regions partitions the imprinted genes Igf2 and H19 into parent-specific chromatin loops. Nat Genet 36:889-93.

Palstra, R. J., Tolhuis, B., Splinter, E., Nijmeijer, R., Grosveld, F., and de Laat, W. 2003. The beta-globin nuclear compartment in development and erythroid differentiation. Nat Genet 35: 190-4.

Patrinos, G. P., de Krom, M., de Boer, E., Langeveld, A., Imam, A. M. A, Strouboulis, J., de Laat, W., and Grosveld, F. G. (2004). Multiple interactions between regulatory regions are required to stabilize an active chromatin hub. Genes & Dev. 18: 1495-1509.

Spilianakis C G, Flavell R A. 2004. Long-range intrachromosomal interactions in the T helper type 2 cytokine locus. Nat Immunol 5:1017-27.

Tolhuis, B., Palstra, R. J., Splinter; E., Grosveld, F., and de Laat, W. 2002. Looping and interaction between hypersensitive sites in the active beta-globin locus. Molecular Cell 10: 1453-65.

Vakoc C R, Letting D L, Gheldof N, Sawado T, Bender M A, Groudine M, Weiss M J, Dekker J, Blobel G A. 2005. Proximity among distant regulatory elements at the beta-globin locus requires GATA-1 and FOG-1. Mol Cell. 17:453-62

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method for analyzing the frequency of interaction of a target nucleotide sequence with one or more nucleotide sequences of interest comprising the steps of:
 (a) providing a sample of cross-linked DNA;
 (b) digesting the cross-linked DNA with a primary restriction enzyme;
 (c) ligating the cross-linked nucleotide sequences;
 (d) reversing the cross linking;
 (e) digesting the nucleotide sequences with a secondary restriction enzyme;
 (f) ligating one or more DNA sequences of known nucleotide composition to the available secondary restriction enzyme digestion site(s) that flank the one or more nucleotide sequences of interest;
(g) amplifying the one or more nucleotide sequences of interest using at least two oligonucleotide primers, wherein each primer hybridizes to the DNA sequences that flank the nucleotide sequences of interest;
(h) hybridizing the amplified sequence(s) to an array; and
(i) determining the frequency of interaction between the DNA sequences.

2. The method according to claim 1, wherein the ligation reaction in step (f) results in the formation of DNA circles.

3. The method according to claim 1, wherein the target nucleotide sequence is selected from the group consisting of a genomic rearrangement, promoter, an enhancer, a silencer, an insulator, a matrix attachment region, a locus control region, a transcription unit, an origin of replication, a recombination hotspot, a translocation breakpoint, a centromere, a telomere, a gene-dense region, a gene-poor region, a repetitive element and a viral integration site.

4. The method according to any of the preceding claims, wherein the target nucleotide sequence is a nucleotide sequence that is associated with or causes a disease, or is located up to or greater than 15 Mb on a linear DNA template from a locus that is associated with or causes a disease.

5. The method according to claim 1, wherein the target nucleotide sequence is selected from the group consisting of AML1, MLL, MYC, BCL, BCR, ABL1, IGH, LYL1, TAL1, TAL2, LMO2, TCRαδ, TCRβ and HOX or other loci associated with disease.

6. The method according to claim 1, wherein the primary restriction enzyme is a restriction enzyme that recognizes a 6-8 bp recognition site.

7. The method according to claim 6, wherein the primary restriction enzyme is selected from the group consisting of BglII, HindIII, EcoRI, BamHI, SpeI, PstI, and NdeI.

8. The method according claim 1, wherein the secondary restriction enzyme is a restriction enzyme that recognizes a 4 or 5 bp nucleotide sequence recognition site.

9. The method according to claim 1, wherein the secondary restriction enzyme recognition site is located at greater than 350 bp from the primary restriction site in the target nucleotide sequence.

10. The method according to claim 1, wherein the nucleotide sequence is labeled.

11. A method for analyzing the frequency of interaction of a target nucleotide sequence with one or more nucleotide sequences comprising the steps of:
(a) providing a sample of cross-linked DNA;
(b) digesting the cross-linked DNA with a primary restriction enzyme;
(c) ligating the cross-linked nucleotide sequences;
(d) reversing the cross linking;
(e) digesting the nucleotide sequences with a secondary restriction enzyme;
(f) circularizing the nucleotide sequences;
(g) amplifying the one or more nucleotide sequences that are ligated to the target nucleotide sequence;
(h) optionally hybridizing the amplified sequences to an array; and
(i) determining the frequency of interaction between the DNA sequences.

12. A method for preparing a circularized nucleotide sequence comprising the steps of:
(a) providing a sample of cross-linked DNA;
(b) digesting the cross-linked DNA with a primary restriction enzyme;
(c) ligating the cross-linked nucleotide sequences;
(d) reversing the cross linking;
(e) digesting the nucleotide sequences with a secondary restriction enzyme; and
(f) circularizing the nucleotide sequences.

13. A method for identifying one or more DNA-DNA interactions that are indicative of a particular disease state comprising the step of performing steps (a)-(i) of claim 1 wherein in step (a) a sample of cross-linked DNA is provided from a diseased and a non-diseased cell, and wherein a difference between the frequency of interaction between the DNA sequences from the diseased and non-diseased cells indicates that the DNA-DNA interaction is indicative of a particular disease state.

14. A method of diagnosis or prognosis of a disease or syndrome caused by or associated with a change in a DNA-DNA interaction comprising the step of performing steps (a)-(i) of claim 1, wherein step (a) comprises providing a sample of cross-linked DNA from a subject; and wherein step (i) comprises comparing the frequency of interaction between the DNA sequences with that of an unaffected control; wherein a difference between the value obtained from the control and the value obtained from the subject is indicative that the subject is suffering from the disease or syndrome or is indicative that the subject will suffer from the disease or syndrome.

15. The method according to claim 14, wherein a transition from low to high interaction frequencies is indicative of the location of a balanced and/or unbalanced breakpoint.

16. The method according to 14, wherein an inversed pattern of DNA-DNA interaction frequencies for the subject sample as compared to the control is indicative of an balanced and/or unbalanced inversion.

17. The method according to claim 14, wherein a reduction in the DNA-DNA interaction frequency for the subject sample as compared to the control, in combination with an increase in DNA-DNA interaction frequency for more distant regions, is indicative of a balanced and/or unbalanced deletion.

18. The method according to claim 14, wherein an increase or a decrease in DNA-DNA interaction frequency for the subject sample as compared to the control is indicative of a balanced and/or unbalanced duplication or insertion.

19. A method according to claim 14, wherein spectral karyotyping and/or FISH is used prior to performing said method.

20. The method according to claim 14, wherein the disease is a genetic disease.

21. The method according to claim 14, wherein the disease is cancer.

22. A method of diagnosis or prognosis of a disease or syndrome caused by or associated with a change in a DNA-DNA interaction comprising the step of:
performing steps (a)-(i) of claim 1, wherein step (a) comprises providing a sample of cross-linked DNA from a subject; and wherein said method comprises the additional step of:
(j) identifying one or more loci that have undergone a genomic rearrangement that is associated with a disease.

23. The method according to claim 22, wherein the two or more amplified sequences are differentially labeled.

24. The method according to claim 22, wherein the two or more amplified sequences are identically labeled when the sequences reside on different chromosomes.

25. The method according to claim 22, wherein the two or more amplified sequences are identically labeled when the sequences reside on the same chromosome at a distance that is far enough for minimal overlap between DNA-DNA interaction signals.

26. An assay method for identifying one or more agents that modulate a DNA-DNA interaction comprising the steps of:
   (a) contacting a sample with one or more agents; and
   (b) performing steps (a) to (i) of claim 1, wherein step (a) comprises providing cross-linked DNA from the sample;
   wherein a difference between (i) the frequency of interaction between the DNA sequences in the presence of the agent and (ii) the frequency of interaction between the DNA sequences in the absence of the agent is indicative of an agent that modulates the DNA-DNA interaction.

27. A method for detecting the location of a balanced and/or unbalanced breakpoint (a translocation) comprising the step of:
   (a) performing steps (a) to (i) of any of claim 1; and
   (b) comparing the frequency of interaction between the DNA sequences with that of a control;
   wherein a transition from low to high DNA-DNA interaction frequency in the sample as compared to the control is indicative of the location of a breakpoint.

28. A method for detecting the location of a balanced and/or unbalanced inversion comprising the steps of:
   (a) performing steps (a) to (i) of claim 1; and
   (b) comparing the frequency of interaction between the DNA sequences with that of a control;
   wherein an inversed pattern of DNA-DNA interaction frequencies for the sample as compared to the control is indicative of an inversion.

29. A method for detecting the location of a deletion comprising the steps of:
   (a) performing steps (a) to (i) of claim 1; and
   (b) comparing the frequency of interaction between the DNA sequences with that of a control;
   wherein a reduction in the DNA-DNA interaction frequency for the sample as compared to the control is indicative of deletion.

30. A method for detecting the location of a duplication comprising the steps of:
   (a) performing steps (a) to (i) of claim 1; and
   (b) comparing the frequency of interaction between the DNA sequences with that of a control;
   wherein an increase or a decrease in DNA-DNA interaction frequency for the subject sample as compared to the control is indicative of a duplication or insertion.

* * * * *

```
                        SEQUENCE LISTING

<160> NUMBER OF SEQ ID NOS: 32

<210> SEQ ID NO 1
<211> LENGTH: 22
<212> TYPE: DNA
<213> ORGANISM: Artificial
<220> FEATURE:
<223> OTHER INFORMATION: Oligonucleotide primer

<400> SEQUENCE: 1
acttcctaca cattaacgag cc                                              22

<210> SEQ ID NO 2
<211> LENGTH: 23
<212> TYPE: DNA
<213> ORGANISM: Artificial
<220> FEATURE:
<223> OTHER INFORMATION: Oligonucleotide primer

<400> SEQUENCE: 2
gctgttatcc ctttctcttc tac                                             23

<210> SEQ ID NO 3
<211> LENGTH: 18
<212> TYPE: DNA
<213> ORGANISM: Artificial
<220> FEATURE:
<223> OTHER INFORMATION: Oligonucleotide primer

<400> SEQUENCE: 3
tcacacgcga agtaggcc                                                   18

<210> SEQ ID NO 4
<211> LENGTH: 19
<212> TYPE: DNA
<213> ORGANISM: Artificial
<220> FEATURE:
<223> OTHER INFORMATION: Oligonucleotide primer

<400> SEQUENCE: 4
ccttcctcca ccatgatga                                                  19

<210> SEQ ID NO 5
<211> LENGTH: 25
<212> TYPE: DNA
<213> ORGANISM: Artificial
<220> FEATURE:
<223> OTHER INFORMATION: Oligonucleotide primer

<400> SEQUENCE: 5
aacgcatttg ctcaatcaac tactg                                           25

<210> SEQ ID NO 6
<211> LENGTH: 25
<212> TYPE: DNA
<213> ORGANISM: Artificial
<220> FEATURE:
<223> OTHER INFORMATION: Oligonucleotide primer
```

-continued

<400> SEQUENCE: 6
gttgctcctc acatttgctt ctgac                                    25

<210> SEQ ID NO 7
<211> LENGTH: 41
<212> TYPE: DNA
<213> ORGANISM: Artificial
<220> FEATURE:
<223> OTHER INFORMATION: Oligonucleotide primer

<400> SEQUENCE: 7
catgaagaaa cgagcacccc cttgatgttt ctccctttac c                  41

<210> SEQ ID NO 8
<211> LENGTH: 40
<212> TYPE: DNA
<213> ORGANISM: Artificial
<220> FEATURE:
<223> OTHER INFORMATION: Oligonucleotide primer

<400> SEQUENCE: 8
tgtcaggctc ttctcctaca cgtcgtccag aacactcacc                    40

<210> SEQ ID NO 9
<211> LENGTH: 37
<212> TYPE: DNA
<213> ORGANISM: Artificial
<220> FEATURE:
<223> OTHER INFORMATION: Oligonucleotide primer

<400> SEQUENCE: 9
aatccagggc tacttccagc cgtgatgcta tctgcca                       37

<210> SEQ ID NO 10
<211> LENGTH: 38
<212> TYPE: DNA
<213> ORGANISM: Artificial
<220> FEATURE:
<223> OTHER INFORMATION: Oligonucleotide primer

<400> SEQUENCE: 10
tgttggaaga ccaggtgaag tgtcgtggaa agcgagtg                      38

<210> SEQ ID NO 11
<211> LENGTH: 45
<212> TYPE: DNA
<213> ORGANISM: Artificial
<220> FEATURE:
<223> OTHER INFORMATION: Oligonucleotide primer

<400> SEQUENCE: 11
caatcccaga tacattcctc atacaaatac tttccaagac tggac              45

<210> SEQ ID NO 12
<211> LENGTH: 39
<212> TYPE: DNA
<213> ORGANISM: Artificial
<220> FEATURE:
<223> OTHER INFORMATION: Oligonucleotide primer

<400> SEQUENCE: 12
gaatatgtta tgcttgatcc ttccatgaga gaagtctag                     39

<210> SEQ ID NO 13
<211> LENGTH: 18
<212> TYPE: DNA

```
<213> ORGANISM: Artificial
<220> FEATURE:
<223> OTHER INFORMATION: Oligonucleotide primer

<400> SEQUENCE: 13
atgtgactcc tctagatc                                                      18

<210> SEQ ID NO 14
<211> LENGTH: 71
<212> TYPE: DNA
<213> ORGANISM: Artificial
<220> FEATURE:
<223> OTHER INFORMATION: Oligonucleotide primer

<400> SEQUENCE: 14
aatgatacgg cgaccaccga acactctttc cctacacgac gctcttccga tctatgtgac        60
tcctctagat c                                                             71

<210> SEQ ID NO 15
<211> LENGTH: 19
<212> TYPE: DNA
<213> ORGANISM: Artificial
<220> FEATURE:
<223> OTHER INFORMATION: Oligonucleotide primer

<400> SEQUENCE: 15
ccctgaacct cttgaagct                                                     19

<210> SEQ ID NO 16
<211> LENGTH: 40
<212> TYPE: DNA
<213> ORGANISM: Artificial
<220> FEATURE:
<223> OTHER INFORMATION: Oligonucleotide primer

<400> SEQUENCE: 16
caagcagaag acggcatacg accctgaacc tcttgaagct                              40

<210> SEQ ID NO 17
<211> LENGTH: 18
<212> TYPE: DNA
<213> ORGANISM: Artificial
<220> FEATURE:
<223> OTHER INFORMATION: Oligonucleotide primer

<400> SEQUENCE: 17
cggcctccaa ttgtgatc                                                      18

<210> SEQ ID NO 18
<211> LENGTH: 71
<212> TYPE: DNA
<213> ORGANISM: Artificial
<220> FEATURE:
<223> OTHER INFORMATION: Oligonucleotide primer

<400> SEQUENCE: 18
aatgatacgg cgaccaccga acactctttc cctacacgac gctcttccga tctcggcctc        60
caattgtgat c                                                             71

<210> SEQ ID NO 19
<211> LENGTH: 20
<212> TYPE: DNA
<213> ORGANISM: Artificial
<220> FEATURE:
<223> OTHER INFORMATION: Oligonucleotide primer
```

```
<400> SEQUENCE: 19
gaattgcttt tggtaagctt                                                   20

<210> SEQ ID NO 20
<211> LENGTH: 41
<212> TYPE: DNA
<213> ORGANISM: Artificial
<220> FEATURE:
<223> OTHER INFORMATION: Oligonucleotide primer

<400> SEQUENCE: 20
caagcagaag acggcatacg agaattgctt ttggtaagct t                           41

<210> SEQ ID NO 21
<211> LENGTH: 18
<212> TYPE: DNA
<213> ORGANISM: Artificial
<220> FEATURE:
<223> OTHER INFORMATION: Oligonucleotide primer

<400> SEQUENCE: 21
ttttagccct gacagatc                                                     18

<210> SEQ ID NO 22
<211> LENGTH: 71
<212> TYPE: DNA
<213> ORGANISM: Artificial
<220> FEATURE:
<223> OTHER INFORMATION: Oligonucleotide primer

<400> SEQUENCE: 22
aatgatacgg cgaccaccga acactctttc cctacacgac gctcttccga tcttttagc        60 cctgacagat c                                                            71

<210> SEQ ID NO 23
<211> LENGTH: 20
<212> TYPE: DNA
<213> ORGANISM: Artificial
<220> FEATURE:
<223> OTHER INFORMATION: Oligonucleotide primer

<400> SEQUENCE: 23
agtcaaacat aagcctaagc                                                   20

<210> SEQ ID NO 24
<211> LENGTH: 41
<212> TYPE: DNA
<213> ORGANISM: Artificial
<220> FEATURE:
<223> OTHER INFORMATION: Oligonucleotide primer

<400> SEQUENCE: 24
caagcagaag acggcatacg aagtcaaaca taagcctaag c                           41

<210> SEQ ID NO 25
<211> LENGTH: 157
<212> TYPE: DNA
<213> ORGANISM: Homo sapiens

<400> SEQUENCE: 25
aaggaaaccc catgcccata agacgtcact aatttctgaa ctcttgtttt tttttttttt       60
ttttcaagta gttctcatct aagtagttgt tttttgtcat gagaaaatca gatatgttgc      120
taaaaattca aactattgc aagaaaaaat aaaagac                                 157
```

```
<210> SEQ ID NO 26
<211> LENGTH: 100
<212> TYPE: DNA
<213> ORGANISM: Homo sapiens

<400> SEQUENCE: 26
ctccaatgta actgtggatt acacctaaaa gagccagaaa acacagactc tctgtggaac      60
catgacacaa cagtgcttgg tattattttt tcctagttag                           100

<210> SEQ ID NO 27
<211> LENGTH: 60
<212> TYPE: DNA
<213> ORGANISM: Homo sapiens

<400> SEQUENCE: 27
aagagccaga aaacacagac tctctgtgga accatgacac aacagtgctt ggtattattt      60

<210> SEQ ID NO 28
<211> LENGTH: 50
<212> TYPE: DNA
<213> ORGANISM: Homo sapiens

<400> SEQUENCE: 28 aaacccatg cccataagac gtcactaatt tctgaactct tgttttttt                   50

<210> SEQ ID NO 29
<211> LENGTH: 45
<212> TYPE: DNA
<213> ORGANISM: Homo sapiens

<400> SEQUENCE: 29
cgaagaactg ctcattgtag gtcaagtttc aaggtcttga accac                      45

<210> SEQ ID NO 30
<211> LENGTH: 52
<212> TYPE: DNA
<213> ORGANISM: Homo sapiens

<400> SEQUENCE: 30
tctgtgccag cagcttgtgc cgcgagccgg ccgatactct gcctaggact cc              52

<210> SEQ ID NO 31
<211> LENGTH: 30
<212> TYPE: DNA
<213> ORGANISM: Homo sapiens

<400> SEQUENCE: 31
gaccagggca ttggatttat ttcagagatc                                       30

<210> SEQ ID NO 32
<211> LENGTH: 26
<212> TYPE: DNA
<213> ORGANISM: Homo sapiens

<400> SEQUENCE: 32
gatcctgaca ccttagagct aagctt                                           26
```